US009434771B2

(12) United States Patent
Li et al.

(10) Patent No.: US 9,434,771 B2
(45) Date of Patent: Sep. 6, 2016

(54) COMPOSITIONS AND METHODS FOR DIAGNOSING AND TREATING INFLAMMATORY BOWEL DISEASE AND RELATED DISORDERS

(75) Inventors: Xuhang Li, Baltimore, MD (US); Heng Zhu, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 513 days.

(21) Appl. No.: 13/140,702

(22) PCT Filed: Dec. 17, 2009

(86) PCT No.: PCT/US2009/006647
§ 371 (c)(1),
(2), (4) Date: Jun. 17, 2011

(87) PCT Pub. No.: WO2010/077323
PCT Pub. Date: Jul. 8, 2010

(65) Prior Publication Data
US 2011/0251100 A1  Oct. 13, 2011

Related U.S. Application Data

(60) Provisional application No. 61/138,309, filed on Dec. 17, 2008.

(51) Int. Cl.
*G01N 33/68* (2006.01)
*C07K 14/245* (2006.01)
(52) U.S. Cl.
CPC ......... *C07K 14/245* (2013.01); *G01N 33/6854* (2013.01); *G01N 2333/245* (2013.01); *G01N 2800/065* (2013.01)

(58) Field of Classification Search
None
See application file for complete search history.

(56) References Cited

U.S. PATENT DOCUMENTS

2010/0004213 A1* 1/2010 Abbas et al. ................ 514/166
2011/0111458 A1* 5/2011 Masuda et al. ............ 435/69.1

OTHER PUBLICATIONS

Velayos et al. (2007) "Positioning biologic therapy for Crohn's disease and ulcerative colitis" Current Gastroenterology Reports 9(6):521-527.*
Chen et al., "A proteome chip approach reveals new DNA damage recognition activities in *Escherichia coli*", Nature Methods, vol. 5, No. 1, pp. 69-74 (2008).
Ruan et al., "Immunobiosensor Chips for Detection of *Escherichia coli* O157:H7 Using Electochemical Impedence Spectroscopy", Anal. Chem., vol. 74, pp. 4814-4820 (2002).
Stokes et al., "Detection of *E. coli* using a microfluidics-based antibody biochip detection system", Fresenius J Anal Chem, vol. 369, pp. 295-301 (2001).
Davies et al., "Profiling the humoral immune response to infection by using proteome microarrays: High-Throughput vaccine and diagnostic antigen discovery", PNAS, vol. 102, No. 3, pp. 547-552 (2005).

* cited by examiner

*Primary Examiner* — Karen S Weiler
(74) *Attorney, Agent, or Firm* — Mintz Levin Cohn Ferris Glovsky and Popeo, P.C.; Peter F. Corless; Christopher R. Cowles

(57) ABSTRACT

The present invention features biomarkers capable of diagnosing inflammatory bowel disease and methods of using such biomarkers to diagnose and selecting treatments for inflammatory bowel diseases.

11 Claims, 9 Drawing Sheets frvX 
CD 58989    UC 59001 yidX

A. ompC ratio plot

B. fliC ratio plot

SEQUENCE LISTING

<160> NUMBER OF SEQ ID NOS: 6

<210> SEQ ID NO 1
<211> LENGTH: 301
<212> TYPE: PRT
<213> ORGANISM: Escherichia coli

<400> SEQUENCE: 1

Met Ser Ile Asp Lys Ser Tyr Cys Gly Phe Ile Ala Ile Val Gly Arg
1               5                   10                  15

Pro Asn Val Gly Lys Ser Thr Leu Leu Asn Lys Leu Leu Gly Gln Lys
            20                  25                  30

```
Ile Ser Ile Thr Ser Arg Lys Ala Gln Thr Thr Arg His Arg Ile Val
            35                  40                  45

Gly Ile His Thr Glu Gly Ala Tyr Gln Ala Ile Tyr Val Asp Thr Pro
 50                  55                  60

Gly Leu His Met Glu Glu Lys Arg Ala Ile Asn Arg Leu Met Asn Lys
 65                  70                  75                  80

Ala Ala Ser Ser Ser Ile Gly Asp Val Glu Leu Val Ile Phe Val Val
                85                  90                  95

Glu Gly Thr Arg Trp Thr Pro Asp Asp Glu Met Val Leu Asn Lys Leu
            100                 105                 110

Arg Glu Gly Lys Ala Pro Val Ile Leu Ala Val Asn Lys Val Asp Asn
            115                 120                 125

Val Gln Glu Lys Ala Asp Leu Leu Pro His Leu Gln Phe Leu Ala Ser
        130                 135                 140

Gln Met Asn Phe Leu Asp Ile Val Pro Ile Ser Ala Glu Thr Gly Leu
145                 150                 155                 160

Asn Val Asp Thr Ile Ala Ala Ile Val Arg Lys His Leu Pro Glu Ala
                165                 170                 175

Thr His His Phe Pro Glu Asp Tyr Ile Thr Asp Arg Ser Gln Arg Phe
            180                 185                 190

Met Ala Ser Glu Ile Ile Arg Glu Lys Leu Met Arg Phe Leu Gly Ala
            195                 200                 205

Glu Leu Pro Tyr Ser Val Thr Val Glu Ile Glu Arg Phe Val Ser Asn
        210                 215                 220

Glu Arg Gly Gly Tyr Asp Ile Asn Gly Leu Ile Leu Val Glu Arg Glu
225                 230                 235                 240

Gly Gln Lys Lys Met Val Ile Gly Asn Lys Gly Ala Lys Ile Lys Thr
                245                 250                 255

Ile Gly Ile Glu Ala Arg Lys Asp Met Gln Glu Met Phe Glu Ala Pro
            260                 265                 270

Val His Leu Glu Leu Trp Val Lys Val Lys Ser Gly Trp Ala Asp Asp
        275                 280                 285

Glu Arg Ala Leu Arg Ser Leu Gly Tyr Val Asp Asp Leu
        290                 295                 300

<210> SEQ ID NO 2
<211> LENGTH: 125
<212> TYPE: PRT
<213> ORGANISM: Escherichia coli

<400> SEQUENCE: 2

Met Gln Arg Ile Ile Leu Ile Ile Gly Trp Leu Ala Val Val Leu
1               5                   10                  15

Gly Thr Leu Gly Val Val Leu Pro Val Leu Pro Thr Thr Pro Phe Ile
            20                  25                  30

Leu Leu Ala Ala Trp Cys Phe Ala Arg Ser Ser Pro Arg Phe His Ala
        35                  40                  45

Trp Leu Leu Tyr Arg Ser Trp Phe Gly Ser Tyr Leu Arg Phe Trp Gln
    50                  55                  60

Lys His His Ala Met Pro Arg Gly Val Lys Pro Arg Ala Ile Leu Leu
65                  70                  75                  80

Ile Leu Leu Thr Phe Ala Ile Ser Leu Trp Phe Val Gln Met Pro Trp
                85                  90                  95

Val Arg Ile Met Leu Leu Val Ile Leu Ala Cys Leu Leu Phe Tyr Met
```

```
                    100                 105                 110

Trp Arg Ile Pro Val Ile Asp Glu Lys Gln Glu Lys His
        115                 120                 125

<210> SEQ ID NO 3
<211> LENGTH: 197
<212> TYPE: PRT
<213> ORGANISM: Escherichia coli

<400> SEQUENCE: 3

Met Asn Glu Ile Ile Ser Ala Ala Val Leu Leu Ile Leu Ile Met Asp
1               5                   10                  15

Pro Leu Gly Asn Leu Pro Ile Phe Met Ser Val Leu Lys His Thr Glu
            20                  25                  30

Pro Lys Arg Arg Arg Ala Ile Met Val Arg Glu Leu Leu Ile Ala Leu
        35                  40                  45

Leu Val Met Leu Val Phe Leu Phe Ala Gly Lys Ile Leu Ala Phe
    50                  55                  60

Leu Ser Leu Arg Ala Glu Thr Val Ser Ile Ser Gly Gly Ile Ile Leu
65              70                  75                  80

Phe Leu Ile Ala Ile Lys Met Ile Phe Pro Ser Ala Ser Gly Asn Ser
                85                  90                  95

Ser Gly Leu Pro Ala Gly Glu Glu Pro Phe Ile Val Pro Leu Ala Ile
            100                 105                 110

Pro Leu Val Ala Gly Pro Thr Ile Leu Ala Thr Leu Met Leu Leu Ser
        115                 120                 125

His Gln Tyr Pro Asn Gln Met Gly His Leu Val Ile Ala Leu Leu Leu
    130                 135                 140

Ala Trp Gly Gly Thr Phe Val Ile Leu Leu Gln Ser Ser Leu Phe Leu
145                 150                 155                 160

Arg Leu Leu Gly Glu Lys Gly Val Asn Ala Leu Glu Arg Leu Met Gly
                165                 170                 175

Leu Ile Leu Val Met Met Ala Thr Gln Met Phe Leu Asp Gly Ile Arg
            180                 185                 190

Met Trp Met Lys Gly
        195

<210> SEQ ID NO 4
<211> LENGTH: 285
<212> TYPE: PRT
<213> ORGANISM: Escherichia coli

<400> SEQUENCE: 4

Met Lys Ala Asp Asn Pro Phe Asp Leu Leu Leu Pro Ala Ala Met Ala
1               5                   10                  15

Lys Val Ala Glu Glu Ala Gly Val Tyr Lys Ala Thr Lys His Pro Leu
            20                  25                  30

Lys Thr Phe Tyr Leu Ala Ile Thr Ala Gly Val Phe Ile Ser Ile Ala
        35                  40                  45

Phe Val Phe Tyr Ile Thr Ala Thr Thr Gly Thr Gly Thr Met Pro Phe
    50                  55                  60

Gly Met Ala Lys Leu Val Gly Gly Ile Cys Phe Ser Leu Gly Leu Ile
65              70                  75                  80

Leu Cys Val Val Cys Gly Ala Asp Leu Phe Thr Ser Thr Val Leu Ile
                85                  90                  95

Val Val Ala Lys Ala Ser Gly Arg Ile Thr Trp Gly Gln Leu Ala Lys
```

```
                100             105             110
Asn Trp Leu Asn Val Tyr Phe Gly Asn Leu Val Gly Ala Leu Leu Phe
            115                 120                 125

Val Leu Leu Met Trp Leu Ser Gly Glu Tyr Met Thr Ala Asn Gly Gln
    130                 135                 140

Trp Gly Leu Asn Val Leu Gln Thr Ala Asp His Lys Val His His Thr
145                 150                 155                 160

Phe Ile Glu Ala Val Cys Leu Gly Ile Leu Ala Asn Leu Met Val Cys
                165                 170                 175

Leu Ala Val Trp Met Ser Tyr Ser Gly Arg Ser Leu Met Asp Lys Ala
            180                 185                 190

Phe Ile Met Val Leu Pro Val Ala Met Phe Val Ala Ser Gly Phe Glu
            195                 200                 205

His Ser Ile Ala Asn Met Phe Met Ile Pro Met Gly Ile Val Ile Arg
    210                 215                 220

Asp Phe Ala Ser Pro Glu Phe Trp Thr Ala Val Gly Ser Ala Pro Glu
225                 230                 235                 240

Asn Phe Ser His Leu Thr Val Met Asn Phe Ile Thr Asp Asn Leu Ile
                245                 250                 255

Pro Val Thr Ile Gly Asn Ile Ile Gly Gly Leu Leu Val Gly Leu
            260                 265                 270

Thr Tyr Trp Val Ile Tyr Leu Arg Glu Asn Asp His His
            275                 280                 285

<210> SEQ ID NO 5
<211> LENGTH: 426
<212> TYPE: PRT
<213> ORGANISM: Escherichia coli

<400> SEQUENCE: 5

Met Asn Ser Asn Lys Glu Leu Met Gln Arg Arg Ser Gln Ala Ile Pro
1               5                   10                  15

Arg Gly Val Gly Gln Ile His Pro Ile Phe Ala Asp Arg Ala Glu Asn
            20                  25                  30

Cys Arg Val Trp Asp Val Glu Gly Arg Glu Tyr Leu Asp Phe Ala Gly
        35                  40                  45

Gly Ile Ala Val Leu Asn Thr Gly His Leu His Pro Lys Val Val Ala
    50                  55                  60

Ala Val Glu Ala Gln Leu Lys Lys Leu Ser His Thr Cys Phe Gln Val
65                  70                  75                  80

Leu Ala Tyr Glu Pro Tyr Leu Glu Leu Cys Glu Ile Met Asn Gln Lys
                85                  90                  95

Val Pro Gly Asp Phe Ala Lys Lys Thr Leu Leu Val Thr Thr Gly Ser
            100                 105                 110

Glu Ala Val Glu Asn Ala Val Lys Ile Ala Arg Ala Ala Thr Lys Arg
            115                 120                 125

Ser Gly Thr Ile Ala Phe Ser Gly Ala Tyr His Gly Arg Thr His Tyr
    130                 135                 140

Thr Leu Ala Leu Thr Gly Lys Val Asn Pro Tyr Ser Ala Gly Met Gly
145                 150                 155                 160

Leu Met Pro Gly His Val Tyr Arg Ala Leu Tyr Pro Cys Pro Leu His
                165                 170                 175

Gly Ile Ser Glu Asp Asp Ala Ile Ala Ser Ile His Arg Ile Phe Lys
            180                 185                 190
```

```
Asn Asp Ala Ala Pro Glu Asp Ile Ala Ala Ile Val Ile Glu Pro Val
            195                 200                 205
Gln Gly Glu Gly Gly Phe Tyr Ala Ser Ser Pro Ala Phe Met Gln Arg
    210                 215                 220
Leu Arg Ala Leu Cys Asp Glu His Gly Ile Met Leu Ile Ala Asp Glu
225                 230                 235                 240
Val Gln Ser Gly Ala Gly Arg Thr Gly Thr Leu Phe Ala Met Glu Gln
                245                 250                 255
Met Gly Val Ala Pro Asp Leu Thr Thr Phe Ala Lys Ser Ile Ala Gly
            260                 265                 270
Gly Phe Pro Leu Ala Gly Val Thr Gly Arg Ala Glu Val Met Asp Ala
        275                 280                 285
Val Ala Pro Gly Gly Leu Gly Gly Thr Tyr Ala Gly Asn Pro Ile Ala
    290                 295                 300
Cys Val Ala Ala Leu Glu Val Leu Lys Val Phe Glu Gln Glu Asn Leu
305                 310                 315                 320
Leu Gln Lys Ala Asn Asp Leu Gly Gln Lys Leu Lys Asp Gly Leu Leu
                325                 330                 335
Ala Ile Ala Glu Lys His Pro Glu Ile Gly Asp Val Arg Gly Leu Gly
            340                 345                 350
Ala Met Ile Ala Ile Glu Leu Phe Glu Asp Gly Asp His Asn Lys Pro
        355                 360                 365
Asp Ala Lys Leu Thr Ala Glu Ile Val Ala Arg Ala Arg Asp Lys Gly
    370                 375                 380
Leu Ile Leu Leu Ser Cys Gly Pro Tyr Tyr Asn Val Leu Arg Ile Leu
385                 390                 395                 400
Val Pro Leu Thr Ile Glu Asp Ala Gln Ile Arg Gln Gly Leu Glu Ile
                405                 410                 415
Ile Ser Gln Cys Phe Asp Glu Ala Lys Gln
            420                 425

<210> SEQ ID NO 6
<211> LENGTH: 442
<212> TYPE: PRT
<213> ORGANISM: Escherichia coli

<400> SEQUENCE: 6

Met Ala Met Phe Gly Phe Pro His Trp Gln Leu Lys Ser Thr Ser Thr
1               5                   10                  15
Glu Ser Gly Val Val Ala Pro Asp Glu Arg Leu Pro Phe Ala Gln Thr
            20                  25                  30
Ala Val Met Gly Val Gln His Ala Val Ala Met Phe Gly Ala Thr Val
        35                  40                  45
Leu Met Pro Ile Leu Met Gly Leu Asp Pro Asn Leu Ser Ile Leu Met
    50                  55                  60
Ser Gly Ile Gly Thr Leu Leu Phe Phe Ile Thr Gly Gly Arg Val
65                  70                  75                  80
Pro Ser Tyr Leu Gly Ser Ser Ala Ala Phe Val Gly Val Val Ile Ala
                85                  90                  95
Ala Thr Gly Phe Asn Gly Gln Gly Ile Asn Pro Asn Ile Ser Ile Ala
            100                 105                 110
Leu Gly Gly Ile Ile Ala Cys Gly Leu Val Tyr Thr Val Ile Gly Leu
        115                 120                 125
Val Val Met Lys Ile Gly Thr Arg Trp Ile Glu Arg Leu Met Pro Pro
    130                 135                 140
```

```
Val Val Thr Gly Ala Val Val Met Ala Ile Gly Leu Asn Leu Ala Pro
145                 150                 155                 160

Ile Ala Val Lys Ser Val Ser Ala Ser Ala Phe Asp Ser Trp Met Ala
                165                 170                 175

Val Met Thr Val Leu Cys Ile Gly Leu Val Ala Val Phe Thr Arg Gly
            180                 185                 190

Met Ile Gln Arg Leu Leu Ile Leu Val Gly Leu Ile Val Ala Cys Leu
        195                 200                 205

Leu Tyr Gly Val Met Thr Asn Val Leu Gly Leu Gly Lys Ala Val Asp
    210                 215                 220

Phe Thr Leu Val Ser His Ala Ala Trp Phe Gly Leu Pro His Phe Ser
225                 230                 235                 240

Thr Pro Ala Phe Asn Gly Gln Ala Met Met Leu Ile Ala Pro Val Ala
                245                 250                 255

Val Ile Leu Val Ala Glu Asn Leu Gly His Leu Lys Ala Val Ala Gly
            260                 265                 270

Met Thr Gly Arg Asn Met Asp Pro Tyr Met Gly Arg Ala Phe Val Gly
        275                 280                 285

Asp Gly Leu Ala Thr Met Leu Ser Gly Ser Val Gly Gly Ser Gly Val
    290                 295                 300

Thr Thr Tyr Ala Glu Asn Ile Gly Val Met Ala Val Thr Lys Val Tyr
305                 310                 315                 320

Ser Thr Leu Val Phe Val Ala Ala Val Ile Ala Met Leu Leu Gly
                325                 330                 335

Phe Ser Pro Lys Phe Gly Ala Leu Ile His Thr Ile Pro Ala Ala Val
            340                 345                 350

Ile Gly Gly Ala Ser Ile Val Val Phe Gly Leu Ile Ala Val Ala Gly
        355                 360                 365

Ala Arg Ile Trp Val Gln Asn Arg Val Asp Leu Ser Gln Asn Gly Asn
370                 375                 380

Leu Ile Met Val Ala Val Thr Leu Val Leu Gly Ala Gly Asp Phe Ala
385                 390                 395                 400

Leu Thr Leu Gly Gly Phe Thr Leu Gly Gly Ile Gly Thr Ala Thr Phe
            405                 410                 415

Gly Ala Ile Leu Leu Asn Ala Leu Leu Ser Arg Lys Leu Val Asp Val
        420                 425                 430

Pro Pro Pro Glu Val Val His Gln Glu Pro
        435                 440
```

COMPOSITIONS AND METHODS FOR DIAGNOSING AND TREATING INFLAMMATORY BOWEL DISEASE AND RELATED DISORDERS

CROSS-REFERENCE TO RELATED APPLICATIONS

This application is a 35 U.S.C. §371 U.S. national entry of International Application PCT/US2009/006647 (WO 2010/077323) having an International filing date of Dec. 17, 2009 which claims the benefit of the following U.S. Provisional Application No. 61/138,309, filed Dec. 17, 2008, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Nov. 12, 2013, is named 85315(71699)_SL.txt and is 15,906 bytes in size.

STATEMENT OF RIGHTS TO INVENTIONS MADE UNDER FEDERALLY SPONSORED RESEARCH

This work was supported by the following grants from the National Institutes of Health, Grant No: NIH 1R21DK077064. The government has certain rights in the invention.

BACKGROUND OF THE INVENTION

Crohn's disease (CD) and ulcerative colitis (UC) are chronic, idiopathic and clinically heterogeneous intestinal disorders collectively known as inflammatory bowel disease (IBD). At present, a combination of clinical, endoscopic and radiological criteria is used to differentiate CD from US. Because the symptoms of Crohn's disease are similar to other intestinal disorders, such as ulcerative colitis, it can be difficult to diagnose. Ulcerative colitis causes inflammation and ulcers in the top layer of the lining of the large intestine. In Crohn's disease, all layers of the intestine may be involved, and normal healthy bowel can be found between sections of diseased bowel. Complications of Crohn's disease include intestinal blockages, which may require surgery, as well as fistulas and fissues. To avoid such complications, it is important to get an accurate diagnosis early in the course of the illness to ensure that appropriate therapies are selected. Current diagnostic methods for inflammatory bowel disease are invasive and patients typically find these tests unpleasant. To improve patient compliance, diagnostic accuracy, and early and appropriate treatment selection, new methods for distinguishing among inflammatory bowel diseases are required.

SUMMARY OF THE INVENTION

As described below, the present invention features biomarkers capable of diagnosing a subject as having inflammatory bowel disease and methods of using such biomarkers to diagnose, monitor and select appropriate treatments for said subject.

In one aspect, the invention provides a microchip containing at least about 85, 90, 95 or 100% of the *E. coli* proteome.

In another aspect, the invention features a microchip containing a set of biomarkers for characterizing an inflammatory bowel disease (IBD) in a subject, where the set is selected from any one or more of *E. coli* polypeptides delineated herein, pairs and sets of polypeptides features in Tables 2-5, 7, and FIG. 5, or any of (yhcP), (yhhT), (yhiW), 16-3B0, 214#3, 233#6, 273#6, 280#1, 316#4, 321#3, 323#1, 331#2, 356#7, 406#7, 409#5, 411#1, 420#7, 452#13, 610#6.1, aceF, allP, ansP, aqpZ, atoE, brnQ, celD, cobU, codB, cybB, cydB, cydC, dgt, dnaQ, ebgA, emrB, emrD, exuR, fabH, fabZ, fadA, fepD, flhD, glnQ, glpF, gppA, greA, hemY, JW0438, JW1949, lipA, lpxC, malX, malZ, menG, mrdB, murG, mutT, narU, nfrB, nfrE, ompC, oppC, oppF, pbuX, pheP, phsE, pnuC, potC, pssR, ptsH, putP, queA, rfaL, rffG, rocE, rplO, sdhD, secB, sfsA, slyX, sucB, sucD, tauB, thiL, trkH, udk, uidB, virK, yaaH, yabK, yadQ, yaeG, yagG, yagM, yaiV, yajR, ybaN, ybdS, ybfB, ybfC, ybgE, ybhA, ybhL, ybhM, ybhN, ybhR, ycaD, yccY, ycdG, yciQ, yciR, yciS, ydcD, yddH, ydeF, ydeZ, ydfO, ydjS, ydjZ, yeaS, yehK, yehY, yejF, yfjY, ygeD, ygfF, yggH, yghK, yghT, ygjQ, yhaH, yhaO, yhbX, yhcO, yhdM, yhdT, yheG, yheU, yhfU, yhhL, yhhS, yhiP, yhiQ, yhjX, yiaL, yiaQ, yibL, yibQ, yicO, yidY, yifE, yigF, yihG, yjeM, yjfF, yjfP, yjfY, yjhB, ymdD, ynaJ, yneC, yneG, ynjC, yoaA, yohG, yphA, yphG, yqcE, yzgL, rpsK, rpsL, sixA, ycfF, yhdN, yjhA, (gntU), (phnE), (rcsC), (thiS), (ycfA), (yfjV), 221#15, 267#6, 304#1, 319#17, 336#6, 348#4, 405#2, 411#4, 416#1, 430#8, 445#15, 448#2, 633#5, aceB, agaZ, aidA, argB, argC, aroF, aroK, aspA, atpB, baiF, basS, cedA, citB, citG, clpX, cysD, cysJ, cysM, cysW, dgxA, dicC, dinD, ecnB, eno, fadB, fba, fdhE, fecB, fecR, fimB, fimC, fliA, fliS, flxA, folP, frvX, ftn, fumB, gabD, galR, gcpE, glvB, grxA, grxC, gst, hemX, hflX, hisS, hofH, hoxK, hsdM, hycA, hycF, hypC, ibpB, infC, ivbL, lasT, LDR-ABC, LDR-D, lldR, mcrD, metB, metJ, mltB, mviN, narY, nuoE, phbA, phnB, phnG, phnM, ppdB, ptpS, ptsN, purM, radC, rbfA, rbsB, recN, rffD, rpiB, rplP, rplQ, rplT, rpmJ, rpsG, rpsR, selD, slyA, slyD, ssi6, sugE, tdcB, thiF, torA, trmD, ubiG, umuD, vacJ, wcaA, ybbA, ybbQ, ycbF, ycdB, yceD, ycgN, ydfA, ydfD, ydfR, ydhL, ydiL, yedF, yehR, yejG, yejO, yfeC, yfhD, yfiC, yfiD, yfjI, yfjQ, ygbA, ygbD, ygbO, ygcQ, ygeW, ygfY, yhaA, yhaC, yhaN, yhcI, yhcJ, yhfR, yhfV, yhgH, yhgI, yicC, yieF, yieJ, yigK, yihA, yihD, yihK, yiiF, yijD, yijF, yjaI, yjbI, yjbL, yjbQ, yjbR, yjcS, yjeB, yjeJ, yjgF, yjhC, yjhE, yjhF, yjhO, yjiA, yliG, ymfE, yohL, yphC, yrbB, (rtn), cadA, lueO, mesJ, mhpF, modC, murA, nrfF, prpE, purK, tpiA, yciD, yejA, ygcE, ygfQ, yhjC, yjfH, yjiJ, (yeeF), 211#11, 23-12A0, 279#6, 427#1, dgkA, dinI, emrY, focA, folK, fsr, ginD, kch, maoC, msbA, nac, nagE, narI, ppx, prtC, rfaB, secF, secY/prlA, trkG, yafJ, yaiM, ybbC, ycbM, ydaA, ydbD, ydhV, yefI, yeiO, ygjR, yhiN, yjgT, yojI, and/or yphD, or fragments thereof.

In another aspect, the invention features a microchip containing a set of biomarkers for characterizing Chrohn's disease in a subject, where the set is any one or more of *E. coli* polypeptides rpsK, rpsL, sixA, ycfF, yhdN, yjhA, (gntU), (phnE), (rcsC), (thiS), (ycfA), (yfjV), 221#15, 267#6, 304#1, 319#17, 336#6, 348#4, 405#2, 411#4, 416#1, 430#8, 445#15, 448#2, 633#5, aceB, agaZ, aidA, argB, argC, aroF, aroK, aspA, atpB, baiF, basS, cedA, citB, citG, clpX, cysD, cysJ, cysM, cysW, dgxA, dicC, dinD, ecnB, eno, fadB, fba, fdhE, fecB, fecR, fimB, fimC, fliA, fliS, flxA, folP, frvX, ftn, fumB, gabD, galR, gcpE, glvB, grxA, grxC, gst, hemX, hflX, hisS, hofH, hoxK, hsdM, hycA, hycF, hypC, ibpB, infC, ivbL, lasT, LDR-ABC, LDR-D, lldR, mcrD, metB, metJ, mltB, mviN, narY, nuoE, phbA, phnB, phnG, phnM, ppdB, ptpS, ptsN, purM, radC, rbfA, rbsB, recN, rffD, rpiB, rplP, rplQ, rplT, rpmJ, rpsG, rpsR, selD, slyA, slyD, ssi6, sugE, tdcB, thiF, torA, timD, ubiG, umuD, vacJ, wcaA, ybbA, ybbQ, ycbF, ycdB, yceD, ycgN, ydfA, ydfD, ydfR, ydhL, ydiL, yedF, yehR, yejG, yejO, yfeC, yfhD, yfiC, yfiD, yfjI, yfjQ, ygbA, ygbD, ygbO, ygcQ, ygeW, ygfY, yhaA, yhaC, yhaN, yhcI, yhcJ, yhfR, yhfV, yhgH, yhgI, yicC, yieF, yieJ, yigK, yihA, yihD, yihK, yiiF, yijD, yijF, yjaI, yjbI, yjbL, yjbQ, yjbR, yjcS, yjeB, yjeJ, yjgF, yjhC, yjhE, yjhF, yjhO, yjiA, yliG, ymfE, yohL, yphC, yrbB, (yhcP), (yhhT), (yhiW), 16-3B0, 214#3, 233#6, 273#6, 280#1, 316#4, 321#3, 323#1, 331#2, 356#7, 406#7, 409#5, 411#1, 420#7, 452#13, 610#6.1, aceF, allP, ansP, aqpZ, atoE, brnQ, celD, cobU, codB, cybB, cydB, cydC, dgt, dnaQ, ebgA, emrB, emrD, exuR, fabH, fabZ, fadA, fepD, flhD, glnQ, glpF, gppA, greA, hemY, JW0438, JW1949, lipA, lpxC, malX, malZ, menG, mrdB, murG, mutT, narU, nfrB, nrfE, ompC, oppC, oppF, pbuX, pheP, phsE, pnuC, potC, pssR, ptsH, putP, queA, rfaL, rffG, rocE, rplO, sdhD, secB, sfsA, slyX, sucB, sucD, tauB, thiL, trkH, udk, uidB, virK, yaaH, yabK, yadQ, yaeG, yagG, yagM, yaiV, yajR, ybaN, ybdS, ybfB, ybfC, ybgE, ybhA, ybhL, ybhM, ybhN, ybhR, ycaD, yccY, ycdG, yciQ, yciR, yciS, ydcD, yddH, ydeF, ydeZ, ydfO, ydjS, ydjZ, yeaS, yehK, yehY, yejF, yfjY, ygeD, ygfF, yggH, yghK, yghT, ygjQ, yhaH, yhaO, yhbX, yhcO, yhdM, yhdT, yheG, yheU, yhfU, yhhL, yhhS, yhiP, yhiQ, yhjX, yiaL, yiaQ, yibL, yibQ, yicO, yidY, yifE, yigF, yihG, yjeM, yjfF, yjfP, yjfY, yjhB, ymdD, ynaJ, yneC, yneG, ynjC, yoaA, yohG, yphA, yphG, yqcE, and/or yzgL, or fragments thereof.

In one embodiment of the above aspect, the set is any one or more of E. coli polypeptides rpsK, rpsL, sixA, ycfF, yhdN, yjhA, (gntU), (phnE), (rcsC), (thiS), (ycfA), (yfjV), 221#15, 267#6, 304#1, 319#17, 336#6, 348#4, 405#2, 411#4, 416#1, 430#8, 445#15, 448#2, 633#5, aceB, agaZ, aidA, argB, argC, aroF, aroK, aspA, atpB, baiF, bassS, cedA, citB, citG, clpX, cysD, cysJ, cysM, cysW, dgxA, dicC, dinD, ecnB, eno, fadB, fba, fdhE, fecB, fecR, fimB, fimC, fliA, fliS, flxA, folP, frvX, ftn, fumB, gabD, galR, gcpE, glvB, grxA, grxC, gst, hemX, hflX, hisS, hofH, hoxK, hsdM, hycA, hycF, hypC, ibpB, infC, ivbL, lasT, LDR-ABC, LDR-D, lldR, mcrD, metB, metJ, mltB, mviN, narY, nuoE, phbA, phnB, phnG, phnM, ppdB, ptpS, ptsN, purM, radC, rbfA, rbsB, recN, rffD, rpiB, rplP, rplQ, rplT, rpmJ, rpsG, rpsR, selD, slyA, slyD, ssi6, sugE, tdcB, thiF, torA, trmD, ubiG, umuD, vacJ, wcaA, ybbA, ybbQ, ycbF, ycdB, yceD, ycgN, ydfA, ydfD, ydfR, ydhL, ydiL, yedF, yehR, yejG, yejO, yfeC, yfhD, yfiC, yfiD, yfjI, yfjQ, ygbA, ygbD, ygbO, ygcQ, ygeW, ygfY, yhaA, yhaC, yhaN, yhcI, yhcJ, yhfR, yhfV, yhgH, yhgI, yicC, yieF, yieJ, yigK, yihA, yihD, yihK, yiiF, yijD, yijF, yjaI, yjbI, yjbL, yjbQ, yjbR, yjcS, yjeB, yjeJ, yjgF, yjhC, yjhE, yjhF, yjhO, yjiA, yliG, ymfE, yohL, yphC, and yrbB, or fragments thereof.

In another aspect, the invention features a microchip containing a set of biomarkers for distinguishing Crohn's Disease from ulcerative colitis, the set containing E. coli polypeptides era, ybaN, yhgN, focA, ga bT and ycdG, or fragments thereof.

In another aspect, the invention features a microchip containing a set of biomarkers for diagnosing ulcerative colitis, where the set is any one or more of E. coli polypeptides (rtn), cadA, lueO, mesJ, mhpF, modC, murA, nrfF, prpE, purK, tpiA, yciD, yejA, ygcE, ygfQ, yhjC, yjfH, yjiJ, (yeeF), 211#11, 23-12A0, 279#6, 427#1, dgkA, dinI, emrY, focA, folK, fsr, ginD, kch, maoC, msbA, nac, nagE, narI, ppx, prtC, rfaB, secF, secY/prlA, trkG, yafJ, yaiM, ybbC, ycbM, ydaA, ydbD, ydhV, yefI, yeiO, ygjR, yhiN, yjgT, yojI, yphD, (yhcP), (yhhT), (yhiW), 16-3B0, 214#3, 233#6, 273#6, 280#1, 316#4, 321#3, 323#1, 331#2, 356#7, 406#7, 409#5, 411#1, 420#7, 452#13, 610#6.1, aceF, allP, ansP, aqpZ, atoE, brnQ, celD, cobU, codB, cybB, cydB, cydC, dgt, dnaQ, ebgA, emrB, emrD, exuR, fabH, fabZ, fadA, fepD, flhD, glnQ, glpF, gppA, greA, hemY, JW0438, JW1949, lipA, lpxC, malX, malZ, menG, mrdB, murG, mutT, narU, nfrB, nrfE, ompC, oppC, oppF, pbuX, pheP, phsE, pnuC, potC, pssR, ptsH, putP, queA, rfaL, rffG, rocE, rplO, sdhD, secB, sfsA, slyX, sucB, sucD, tauB, thiL, trkH, udk, uidB, virK, yaaH, yabK, yadQ, yaeG, yagG, yagM, yaiV, yajR, ybaN, ybdS, ybfB, ybfC, ybgE, ybhA, ybhL, ybhM, ybhN, ybhR, ycaD, yccY, ycdG, yciQ, yciR, yciS, ydcD, yddH, ydeF, ydeZ, ydfO, ydjS, ydjZ, yeaS, yehK, yehY, yejF, yfjY, ygeD, ygfF, yggH, yghK, yghT, ygjQ, yhaH, yhaO, yhbX, yhcO, yhdM, yhdT, yheG, yheU, yhfU, yhhL, yhhS, yhiP, yhiQ, yhjX, yiaL, yiaQ, yibL, yibQ, yicO, yidY, yifE, yigF, yihG, yjeM, yjfF, yjfP, yjfY, yjhB, ymdD, ynaJ, yneC, yneG, ynjC, yoaA, yohG, yphA, yphG, yqcE, and yzgL, or fragments thereof. In one embodiment, the set of biomarkers is any one or more of (rtn), cadA, lueO, mesJ, mhpF, modC, murA, nrfF, prpE, purK, tpiA, yciD, yejA, ygcE, ygfQ, yhjC, yjfH, yjiJ, (yeeF), 211#11, 23-12A0, 279#6, 427#1, dgkA, dinI, emrY, focA, folK, fsr, ginD, kch, maoC, msbA, nac, nagE, narI, ppx, prtC, rfaB, secF, secY/prlA, trkG, yafJ, yaiM, ybbC, ycbM, ydaA, ydbD, ydhV, yefI, yeiO, ygjR, yhiN, yjgT, yojI, and yphD, or fragments thereof.

In yet another aspect, the invention features a microchip containing a set of biomarkers for distinguishing Chrohn's disease from ulcerative colitis, the chip containing a set of biomarkers that is any one or more of rpsK, rpsL, sixA, ycfF, yhdN, yjhA, (gntU), (phnE), (rcsC), (thiS), (ycfA), (yfjV), 221#15, 267#6, 304#1, 319#17, 336#6, 348#4, 405#2, 411#4, 416#1, 430#8, 445#15, 448#2, 633#5, aceB, agaZ, aidA, argB, argC, aroF, aroK, aspA, atpB, baiF, bassS, cedA, citB, citG, clpX, cysD, cysJ, cysM, cysW, dgxA, dicC, dinD, ecnB, eno, fadB, fba, fdhE, fecB, fecR, fimB, fimC, fliA, fliS, flxA, folP, frvX, ftn, fumB, gabD, galR, gcpE, glvB, grxA, grxC, gst, hemX, hflX, hisS, hofH, hoxK, hsdM, hycA, hycF, hypC, ibpB, infC, ivbL, lasT, LDR-ABC, LDR-D, lldR, mcrD, metB, metJ, mltB, mviN, narY, nuoE, phbA, phnB, phnG, phnM, ppdB, ptpS, ptsN, purM, radC, rbfA, rbsB, recN, rffD, rpiB, rplP, rplQ, rplT, rpmJ, rpsG, rpsR, selD, slyA, slyD, ssi6, sugE, tdcB, thiF, torA, trmD, ubiG, umuD, vacJ, wcaA, ybbA, ybbQ, ycbF, ycdB, yceD, ycgN, ydfA, ydfD, ydfR, ydhL, ydiL, yedF, yehR, yejG, yejO, yfeC, yfhD, yfiC, yfiD, yfjI, yfjQ, ygbA, ygbD, ygbO, ygcQ, ygeW, ygfY, yhaA, yhaC, yhaN, yhcI, yhcJ, yhfR, yhfV, yhgH, yhgI, yicC, yieF, yieJ, yigK, yihA, yihD, yihK, yiiF, yijD, yijF, yjaI, yjbI, yjbL, yjbQ, yjbR, yjcS, yjeB, yjeJ, yjgF, yjhC, yjhE, yjhF, yjhO, yjiA, yliG, ymfE, yohL, yphC, yrbB, (rtn), cadA, lueO, mesJ, mhpF, modC, murA, nrfF, prpE, purK, tpiA, yciD, yejA, ygcE, ygfQ, yhjC, yjfH, yjiJ, (yeeF), 211#11, 23-12A0, 279#6, 427#1, dgkA, dinI, emrY, focA, folK, fsr, ginD, kch, maoC, msbA, nac, nagE, narI, ppx, prtC, rfaB, secF, secY/prlA, trkG, yafJ, yaiM, ybbC, ycbM, ydaA, ydbD, ydhV, yefI, yeiO, ygjR, yhiN, yjgT, yojI, and yphD, or fragments thereof.

In various embodiments of the above aspects, the microarrays further contain one or more biomarkers any one or more of antibodies that specifically bind chitobioside IgA (ACCA), laminaribioside IgG (ALCA), manobioside IgG (AMCA), Man α-1,3 Man α-1,2 Man (ΣMan3), Man α-1,3 Man α-1,2 Man α-1,2 Man (ΣMan4) pANCA, antineutrophil cytoplasmic antibody, yeast oligomanna, *Saccharomyces cerevisiae*, ASCA, bacterial outer membrane porin C (OmpC), *Pseudomonas fluorescens* bacterial sequence I2, and bacterial flagellin (Cbir).

In one embodiment of the above aspects, the *E. coli* polypeptide induces an immune response when injected into a subject.

In still another aspect, the invention features a microchip containing a polypeptide, polypeptide set, or polypeptide pair delineated in any of Tables 2-5, 7, or FIG. 5.

In another aspect, the invention features a method for characterizing a condition associated with a dysregulated immune response to a polypeptide in a subject (e.g., human), the method involving contacting a microarray containing a set of polypeptides with sera derived from the subject, and detecting differential antibody binding to a polypeptide on the microarray in the subject sera relative to a control, where detection of differential antibody binding identifies the subject as having a condition associated with a dysregulated immune response [to a].

In another aspect, the invention features a method for diagnosing a subject as having or having a propensity to develop inflammatory bowel disease, the method involving contacting an array containing a set of *E. coli* polypeptides with sera derived from the subject, and detecting differential antibody binding to the polypeptide on the array in the subject sera relative to a healthy control, thereby characterizing inflammatory bowel disease in the subject. In one embodiment, antibodies that bind an *E. coli* polypeptide are any one or more of (yhcP), (yhhT), (yhiW), 16-3B0, 214#3, 233#6, 273#6, 280#1, 316#4, 321#3, 323#1, 331#2, 356#7, 406#7, 409#5, 411#1, 420#7, 452#13, 610#6.1, aceF, allP, ansP, aqpZ, atoE, brnQ, celD, cobU, codB, cybB, cydB, cydC, dgt, dnaQ, ebgA, emrB, emrD, exuR, fabH, fabZ, fadA, fepD, flhD, glnQ, glpF, gppA, greA, hemY, JW0438, JW1949, lipA, lpxC, malX, malZ, menG, mrdB, murG, mutT, narU, nfrB, nrfE, ompC, oppC, oppF, pbuX, pheP, phsE, pnuC, potC, pssR, ptsH, putP, queA, rfaL, rffG, rocE, rplO, sdhD, secB, sfsA, slyX, sucB, sucD, tauB, thiL, trkH, udk, uidB, virK, yaaH, yabK, yadQ, yaeG, yagG, yagM, yaiV, yajR, ybaN, ybdS, ybfB, ybfC, ybgE, ybhA, ybhL, ybhM, ybhN, ybhR, ycaD, yccY, ycdG, yciQ, yciR, yciS, ydcD, yddH, ydeF, ydeZ, ydfO, ydjS, ydjZ, yeaS, yehK, yehY, yejF, yfjY, ygeD, ygfF, yggH, yghK, yghT, ygjQ, yhaH, yhaO, yhbX, yhcO, yhdM, yhdT, yheG, yheU, yhfU, yhhL, yhhS, yhiP, yhiQ, yhjX, yiaL, yiaQ, yibL, yibQ, yicO, yidY, yifE, yigF, yihG, yjeM, yjfF, yjfP, yjfY, yjhB, ymdD, ynaJ, yneC, yneG, ynjC, yoaA, yohG, yphA, yphG, yqcE, and yzgL. In another embodiment, antibodies that bind an *E. coli* polypeptide are any one or more of rpsK, rpsL, sixA, ycfF, yhdN, yjhA, (gntU), (phnE), (rcsC), (thiS), (ycfA), (yfjV), 221#15, 267#6, 304#1, 319#17, 336#6, 348#4, 405#2, 411#4, 416#1, 430#8, 445#15, 448#2, 633#5, aceB, agaZ, aidA, argB, argC, aroF, aroK, aspA, atpB, baiF, basS, cedA, citB, citG, clpX, cysD, cysJ, cysM, cysW, dgxA, dicC, dinD, ecnB, eno, fadB, fba, fdhE, fecB, fecR, fimB, fimC, fliA, fliS, flxA, folP, frvX, ftn, fumB, gabD, galR, gcpE, glvB, grxA, grxC, gst, hemX, hflX, hisS, hofH, hoxK, hsdM, hycA, hycF, hypC, ibpB, infC, ivbL, lasT, LDR-ABC, LDR-D, lldR, mcrD, metB, metJ, mltB, mviN, narY, nuoE, phbA, phnB, phnG, phnM, ppdB, ptpS, ptsN, purM, radC, rbfA, rbsB, recN, rffD, rpiB, rplP, rplQ, rplT, rpmJ, rpsG, rpsR, selD, slyA, slyD, ssi6, sugE, tdcB, thiF, torA, trmD, ubiG, umuD, vacJ, wcaA, ybbA, ybbQ, ycbF, ycdB, yceD, ycgN, ydfA, ydfD, ydfR, ydhL, ydiL, yedF, yehR, yejG, yejO, yfeC, yfhD, yfiC, yfiD, yfjI, yfjQ, ygbA, ygbD, ygbO, ygcQ, ygeW, ygfY, yhaA, yhaC, yhaN, yhcI, yhcJ, yhfR, yhfV, yhgH, yhgI, yicC, yieF, yieJ, yigK, yihA, yihD, yihK, yiiF, yijD, yijF, yjaI, yjbI, yjbL, yjbQ, yjbR, yjcS, yjeB, yjeJ, yjgF, yjhC, yjhE, yjhF, yjhO, yjiA, yliG, ymfE, yohL, yphC, and yrbB. In yet another embodiment, antibodies that bind an *E. coli* polypeptide are any one or more of (rtn), cadA, lueO, mesJ, mhpF, modC, murA, nrfF, prpE, purK, tpiA, yciD, yejA, ygcE, ygfQ, yhjC, yjfH, yjiJ, (yeeF), 211#11, 23-12A0, 279#6, 427#1, dgkA, dinI, emrY, focA, folK, fsr, glnD, kch, maoC, msbA, nac, nagE, narI, ppx, prtC, rfaB, secF, secY/prlA, trkG, yafJ, yaiM, ybbC, ycbM, ydaA, ydbD, ydhV, yefI, yeiO, ygjR, yhiN, yjgT, yojI, and yphD. In one embodiment, an increase in levels of antibodies that specifically bind one or more *E. coli* polypeptides any one or more of rpsK, rpsL, sixA, ycfF, yhdN, yjhA, (gntU), (phnE), (rcsC), (thiS), (ycfA), (yfjV), 221#15, 267#6, 304#1, 319#17, 336#6, 348#4, 405#2, 411#4, 416#1, 430#8, 445#15, 448#2, 633#5, aceB, agaZ, aidA, argB, argC, aroF, aroK, aspA, atpB, baiF, basS, cedA, citB, citG, clpX, cysD, cysJ, cysM, cysW, dgxA, dicC, dinD, ecnB, eno, fadB, fba, fdhE, fecB, fecR, fimB, fimC, fliA, fliS, flxA, folP, frvX, ftn, fumB, gabD, galR, gcpE, glvB, grxA, grxC, gst, hemX, hflX, hisS, hofH, hoxK, hsdM, hycA, hycF, hypC, ibpB, infC, ivbL, lasT, LDR-ABC, LDR-D, lldR, mcrD, metB, metJ, mltB, mviN, narY, nuoE, phbA, phnB, phnG, phnM, ppdB, ptpS, ptsN, purM, radC, rbfA, rbsB, recN, rffD, rpiB, rplP, rplQ, rplT, rpmJ, rpsG, rpsR, selD, slyA, slyD, ssi6, sugE, tdcB, thiF, torA, trmD, ubiG, umuD, vacJ, wcaA, ybbA, ybbQ, ycbF, ycdB, yceD, ycgN, ydfA, ydfD, ydfR, ydhL, ydiL, yedF, yehR, yejG, yejO, yfeC, yfhD, yfiC, yfiD, yfjI, yfjQ, ygbA, ygbD, ygbO, ygcQ, ygeW, ygfY, yhaA, yhaC, yhaN, yhcI, yhcJ, yhfR, yhfV, yhgH, yhgI, yicC, yieF, yieJ, yigK, yihA, yihD, yihK, yiiF, yijD, yijF, yjaI, yjbI, yjbL, yjbQ, yjbR, yjcS, yjeB, yjeJ, yjgF, yjhC, yjhE, yjhF, yjhO, yjiA, yliG, ymfE, yohL, yphC, and yrbB identifies the subject as having Crohn's disease.

In various embodiments of the above aspects, an increase in levels of antibodies that specifically bind one or more *E. coli* polypeptides any one or more of (rtn), cadA, lueO, mesJ, mhpF, modC, murA, nrfF, prpE, purK, tpiA, yciD, yejA, ygcE, ygfQ, yhjC, yjfH, yjiJ, (yeeF), 211#11, 23-12A0, 279#6, 427#1, dgkA, dinI, emrY, focA, folK, fsr, glnD, kch, maoC, msbA, nac, nagE, narI, ppx, prtC, rfaB, secF, secY/prlA, trkG, yafJ, yaiM, ybbC, ycbM, ydaA, ydbD, ydhV, yeII, yeiO, ygjR, yhiN, yjgT, yojI, and yphD identifies the subject as having ulcerative colitis. In other embodiments, an increase in levels of antibodies that specifically bind one or more *E. coli* polypeptides any one or more of (yhcP), (yhhT), (yhiW), 16-3B0, 214#3, 233#6, 273#6, 280#1, 316#4, 321#3, 323#1, 331#2, 356#7, 406#7, 409#5, 411#1, 420#7, 452#13, 610#6.1, aceF, allP, ansP, aqpZ, atoE, brnQ, celD, cobU, codB, cybB, cydB, cydC, dgt, dnaQ, ebgA, emrB, emrD, exuR, fabH, fabZ, fadA, fepD, flhD, glnQ, glpF, gppA, greA, hemY, JW0438, JW1949, lipA, lpxC, malX, malZ, menG, mrdB, murG, mutT, narU, nfrB, nrfE, ompC, oppC, oppF, pbuX, pheP, phsE, pnuC, potC, pssR, ptsH, putP, queA, rfaL, rffG, rocE, rplO, sdhD, secB, sfsA, slyX, sucB, sucD, tauB, thiL, trkH, udk, uidB, virK, yaaH, yabK, yadQ, yaeG, yagG, yagM, yaiV, yajR, ybaN, ybdS, ybfB, ybfC, ybgE, ybhA, ybhL, ybhM, ybhN, ybhR, ycaD, yccY, ycdG, yciQ, yciR, yciS, ydcD, yddH, ydeF, ydeZ, ydfO, ydjS, ydjZ, yeaS, yehK, yehY, yejF, yfjY, ygeD, ygfF, yggH, yghK, yghT, ygjQ, yhaH, yhaO, yhbX, yhcO, yhdM, yhdT, yheG, yheU, yhfU, yhhL, yhhS, yhiP, yhiQ, yhjX, yiaL, yiaQ, yibL, yibQ, yicO, yidY, yifE, yigF, yihG, yjeM, yjfF, yjfP, yjfY, yjhB, ymdD, ynaJ, yneC, yneG, ynjC, yoaA, yohG, yphA, yphG, yqcE, and yzgL identifies the subject as a healthy control.

In another aspect, the invention features a method for diagnosing Crohn's disease, the method involving contacting an array containing a set of *E. coli* polypeptides with sera derived from the subject, and detecting in said subject's sera greater immunogenic reactivity to era than to ybaN, greater immunogenic reactivity to yhgN than to focA, and/or greater immunogenic reactivity to gabT than to ycdG, thereby identifying the subject as having Crohn's Disease.

In another aspect, the invention features a method for diagnosing ulcerative colitis in a subject, the method involving contacting an array containing a set of *E. coli* polypeptides with sera derived from the subject, and detecting in said subject's sera greater immunogenic reactivity to relE>cysE/wcaB, pyrI>yjgK, IntI>ybiO, ftsE>pssR, yhgN>yhfG, yafN>dsbB, yihI>yabK, 421#15>yhdN, hisP>rplO, cml>nuoM, yieC>nuoI, thereby identifying the subject as having ulcerative colitis.

In another aspect, the invention features a method for diagnosing ulcerative colitis, the method involving contacting an array involving a set of *E. coli* polypeptides with sera derived from the subject, and detecting in said subject's sera greater immunogenic reactivity to frvX than to yidX identifies a subject as having ulcerative colitis.

In another aspect, the invention features a method for selecting an appropriate treatment for a subject, the method involving contacting a microarray delineated herein with subject sera and detecting binding to a polypeptide that identifies the subject as having inflammatory bowel disease, thereby indicating that inflammatory bowel disease therapy is appropriate for said subject. In one embodiment, the subject is identified as having Crohn's disease or ulcerative colitis.

In another aspect, the invention features a method for selecting surgery for a subject, the method involving contacting a microarray of any of claims 1-11 with subject sera and detecting binding to a polypeptide that identifies the subject as having inflammatory bowel disease, thereby indicating that surgery is appropriate for said subject. In one embodiment, the method detects greater immunogenic reactivity to era than to ybaN, greater immunogenic reactivity to yhgN than to focA, and/or greater immunogenic reactivity to gabT than to ycdG. In another embodiment, the method detects relE>cysE/wcaB, pyrI>yjgK, IntI>ybiO, ftsE>pssR, yhgN>yhfG, yafN>dsbB, yihI>yabK, 421#15>yhdN, hisP>rplO, cml>nuoM, and/or yieC>nuoI.

In embodiments of the previous aspects, the method further involves detecting an antibody that specifically binds any one or more of chitobioside IgA (ACCA), laminaribioside IgG (ALCA), manobioside IgG (AMCA), Man α-1,3 Man α-1,2 Man (ΣMan3), Man α-1,3 Man α-1,2 Man α-1,2 Man (ΣMan4) pANCA, antineutrophil cytoplasmic antibody, yeast oligomanna, *Saccharomyces cerevisiae*, ASCA, bacterial outer membrane porin C (OmpC), *Pseudomonas fluorescens* bacterial sequence I2, and bacterial flagellin.

In another aspect, the invention features a method for selecting an appropriate treatment method for a subject, the method involving contacting a microarray delineated herein with subject sera and detecting binding to a polypeptide that identifies the subject as not having inflammatory bowel disease, thereby indicating that inflammatory bowel disease therapy is not appropriate for said subject.

In another aspect, the invention features a method for monitoring the condition of a subject having Crohn's disease, the method involving contacting an array containing a set of *E. coli* polypeptides with sera derived from the subject, and detecting in said subject's sera immunogenic reactivity to era relative to ybaN, immunogenic reactivity to yhgN relative to focA, and immunogenic reactivity to gabT relative to ycdG, where a reduction in said immunogenic reactivity identifies an improvement in the subject's condition, and an increase in said immunogenic reactivity identifies a worsening in the subject's condition.

In yet another aspect, the invention features a method for monitoring the condition of a subject having ulcerative colitis, the method involving contacting an array containing a set of *E. coli* polypeptides with sera derived from the subject, and detecting in said subject's sera immunogenic reactivity to frvX relative to yidX, where a reduction in said immunogenic reactivity identifies an improvement in the subject's condition, and an increase in said immunogenic reactivity identifies a worsening in the subject's condition.

In another aspect, the invention features a method for determining whether a therapy is efficacious for a subject, the method involving contacting a microarray of any previous aspect with subject sera collected at a first time and detecting binding to a polypeptide that identifies the subject as having inflammatory bowel disease, and contacting a microarray of any previous aspect with subject sera collected at a second time and detecting binding to a polypeptide that identifies the subject as having inflammatory bowel disease, where detection of a reduction in binding at the second time relative to the first indicates that said therapy is efficacious and a failure to detect a reduction in binding indicates that said therapy is not efficacious.

In another aspect, the invention features a kit containing a microarray of any previous aspect, and instructions for use of the array in diagnosing inflammatory bowel disease, Crohn's disease, or ulcerative colitis.

In various embodiments of the above aspect, or any other method delineated herein, binding is detected in an immunoassay (e.g., ELISA). In other embodiments of the above aspects, the control is a healthy subject, a subject with Crohn's disease, or a subject with ulcerative colitis. In other embodiments of the above aspects, the detecting is of differential binding of a pair of antibodies to a pair of polypeptides on the array (i.e., comparing binding of one antibody to one polypeptide relative to the binding of the other antibody to the other polypeptide). In other embodiments of the above aspects, the array comprises cell wall polypeptides, intracellular polypeptides, and macromolecular complex polypeptides. In other embodiments, an increase in subject antibody binding to a polypeptide relative to healthy control antibody binding identifies the polypeptide as immunogenic in subjects having a dysregulated immune response to the polypeptide. In still other embodiments, the condition is any one or more of inflammatory bowel disease, Crohn's disease, ulcerative colitis, and indeterminate colitis. In various embodiments of the above aspects, the array comprises at least about 85, 90, 95, or 100% of the *E. coli* proteome. In still other embodiments, the polypeptides are differentially immunogenic in healthy controls, Crohn's disease, and/or ulcerative colitis. In still other embodiments, the method further involves detecting an antibody that specifically binds any one or more of chitobioside IgA (ACCA), laminaribioside IgG (ALCA), manobioside IgG (AMCA), Man α-1,3 Man α-1,2 Man (ΣMan3), Man α-1,3 Man α-1,2 Man α-1,2 Man (ΣMan4) pANCA, antineutrophil cytoplasmic antibody, yeast oligomanna, *Saccharomyces cerevisiae*, ASCA, bacterial outer membrane porin C (OmpC), *Pseudomonas fluorescens* bacterial sequence I2, and bacterial flagellin. In still other embodiments, the methods further involve stool sample analysis, colonoscopy, sigmoidoscopy, barium x-ray, computerized axial tomography, and/or capsule endoscopy. In still other embodiments, the method identifies the subject as a healthy control or as not having Crohn's disease or ulcerative colitis. In other embodiments of the above aspects, the invention features a microchip containing a polypeptide, polypeptide set, or polypeptide pair delineated in any of Tables 2-5, 7, or FIG. 5; accordingly, the invention further provides for the detection of differential immunogenicity between pairs of polypeptides or sets of polypeptides relative to a control (e.g., healthy control, UC, or CD)

The invention provides compositions and methods useful for the diagnosis of inflammatory bowel diseases, including distinguishing Crohn's disease from healthy controls and ulcerative colitis. Compositions and articles defined by the invention were isolated or otherwise manufactured in connection with the examples provided below. Other features and advantages of the invention will be apparent from the detailed description, and from the claims.

DEFINITIONS

By "inflammatory bowel disease" is meant a disease characterized by inflammation of the small and/or large intestines.

By "Crohn's disease" is meant an inflammatory bowel disease characterized by chronic inflammation of the gastrointestinal tract.

By "ulcerative colitis" is meant an inflammatory bowel disease characterized by inflammation of the rectum and/or large intestine.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10%-100% change in expression levels (e.g., 10, 20, 30, 40, 50, 60, 75, 80, 85, 90, 95, 100%) change in expression levels.

By "derived from" is meant isolated from or having the sequence of a naturally-occurring sequence (e.g., a cDNA, genomic DNA, synthetic, or combination thereof).

By "microarray" is meant an organized collection of at least two proteins or polypeptides affixed to a solid support. In some embodiments, a polypeptide microarray contains at least a polypeptide or fragment thereof (e.g., 10, 20, 30, 40, 50, 75, or 100 amino acids) listed in any of FIG. 5 and Tables 2-5, and 7. A microarray contains at least 2, 5, 10, 25, 50, 75, 100, 150, 200, 250, or 300 polypeptide or nucleic acid molecule members. Frequently, the surface of the microarray comprises a plurality of addressable locations, each of which location has the adsorbent bound there.

By "biomarker" is meant a polypeptide, polynucleotide, or other molecule that is altered in level or activity in a disease state relative to the level or activity present in a healthy control, or from one disease type (such as Crohn's) from another (such as UC). In one embodiment, a biomarker is a polypeptide that is differentially immunogenic, i.e., that induces an immune response that differs between healthy control subjects and subjects having a disease or disorder.

In another embodiment, a biomarker is a serum antibody that binds to a polypeptide where the serum antibody is differentially present in a subject having a disease or disorder relative to a healthy control subject or a subject not having the disease or disorder.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of an analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

"Diagnostic" means identifying the presence or nature of a pathologic condition. While a particular diagnostic method may not provide a definitive diagnosis of a condition, it suffices if the method provides a positive indication that aids in diagnosis.

By "differentially immunogenic" is meant that a polypeptide induces an altered immune response in a subject having a disease relative to the immune response that the polypeptide induces in a healthy control or a subject not having the disease, or a subject having one type of disease (such as CD) relative to a subject having another disease (such as UC) or vice versa. This difference may be either an increase or a decrease in immune response when compared to control conditions. Preferably, the increase or decrease is at least 10%, 20%, 30%, 40%, 50%, 60%, 70%, 80%, 90%, or even 100%.

By "disease" is meant any condition or disorder that damages or interferes with the normal function of a cell, tissue, or organ.

The invention provides a number of targets that are useful for the development of highly specific drugs to treat inflammatory bowel disease characterized by the methods delineated herein. In addition, the methods of the invention provide a facile means to identify therapies that are safe for use in eukaryotic host organisms. In addition, the methods of the invention provide a route for analyzing virtually any number of compounds for effects on a disease described herein with high-volume throughput, high sensitivity, and low complexity.

By "dysregulated immune response to a pathogen" is meant an excessive or undesirable immune response that causes cell, tissue or organ damage.

By "*E. coli* polypeptide" is meant a protein that naturally occurs in *E. coli*. Such polypeptides are available in Genbank or in the *E. coli* genome and proteome database.

By "fragment" is meant a portion of a polypeptide. This portion contains, preferably, at least 10%, 20%, 30%, 40%, 50%, 60%, 70%, 80%, or 90% of the entire length of the reference polypeptide. A fragment may contain 10, 20, 30, 40, 50, 60, 70, 80, 90, or 100, 200, 300, 400, 500, 600, 700, 800, 900, or 1000 amino acids.

By "function" is meant any biological activity of a polypeptide or polynucleotide. In one embodiment, a polypeptide is an antibody. In another embodiment, a biological activity is immunogenicity.

As used herein, the terms "gene" and "recombinant gene" refer to nucleic acid molecules comprising an open reading frame encoding a marker protein.

By "immunological assay" is meant an assay that relies on an immunological reaction, for example, antibody binding to an antigen. Examples of immunological assays include ELISAs, Western blots, immunoprecipitations, and other assays known to the skilled artisan.

By "polypeptide" is meant any chain of amino acids, regardless of length or post-translational modification (for example, glycosylation or phosphorylation). In one example, an antibody is a polypeptide.

By an "isolated polypeptide" is meant a polypeptide of the invention that has been separated from components that naturally accompany it. Typically, the polypeptide is isolated when it is at least 60%, by weight, free from the proteins and naturally occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "microarray" is meant an organized collection of at least two polypeptides, polynucleotides, or fragments thereof affixed to a solid support. A polypeptide microarray contains one or more polypeptides (e.g., 10, 20, 30, 40, 50, 75, or 100 amino acids) delineated herein. A microarray contains at least 1, 2, 3, 4, 5, 6 polypeptide or nucleic acid molecules delineated herein.

"Monitoring" refers to recording changes in a varying parameter (e.g. monitoring progression of a disease).

As used herein, "obtaining" as in "obtaining an agent" includes synthesizing, purchasing, or otherwise acquiring the agent.

By "pathogen" is meant a bacteria, mycobacteria, fungi (including yeast), virus, or other microbe associated with disease. Exemplary pathogen's include various $E.$ $coli$ strains, $C.$ $difficle,$ $B.$ $fragilis,$ $E.$ $coli$ LF-82 and $H.$ $hepaticus,$ all of which have been demonstrated to be pathogenic to IBD. In certain embodiments, the term pathogen is applied to microbes that are not typically associated with disease in healthy individuals, but that are associated with disease in individuals having a dysregulated immune response (e.g., $E.$ $coli$ K-12 in Crohn's disease and ulcerative colitis).

By "portion" is meant a fragment of a protein or nucleic acid that is substantially identical to a reference protein or nucleic acid. In some embodiments the portion retains at least 50% 75%, or 80%, or more preferably 90%, 95%, or even 99% of the biological activity of the reference protein or nucleic acid described herein.

By "reduces" is meant a negative alteration of at least 10%, 25%, 50%, 75%, or 100%.

By "reference" is meant a standard or control condition.

As used herein, "sample" or "biological sample" refers to anything, which may contain an analyte (e.g., polypeptide, polynucleotide, or fragment thereof) for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. In one embodiment, a biological sample is blood, plasma or serum.

By "a set" is meant a group having more than one member. The set may be composed of 2, 4, 5, 8, 10, 20, 30, 40, 50, 60, 70, 80, 90, 100, 125, 150, 200, 250, or 300 polypeptide, nucleic acid molecule, or chemical compound members.

As used herein, the term "sensitivity" is the percentage of marker-detected subjects with a particular disease.

By "specifically binds" is meant an agent (e.g., antibody) which recognizes and binds a polypeptide of the invention, but that does not substantially recognize and bind other molecules.

As used herein, the term "specificity" is the percentage of subjects correctly identified as having a particular disease. For example, the specificity is calculated as the number of subjects with a particular disease as compared to normal healthy subjects.

By "subject" is meant a mammal, including, but not limited to, a human or non-human mammal, such as a bovine, equine, canine, ovine, rodent, or feline.

By "specifically binds" is meant a compound or antibody that recognizes and binds a polypeptide of the invention, but which does not substantially recognize and bind other molecules in a sample, for example, a biological sample, which naturally includes a polypeptide of the invention.

As used herein, "obtaining" as in "obtaining an agent" includes synthesizing, purchasing, or otherwise acquiring the agent.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 2B is a scatter plot showing duplicate spots are highly correlated with each other (R=0.985). Each point is the plot of the original protein spot expression vs. the technical replicate protein spot expression. All 4265 proteins of a single array are displayed in this scatter plot.

FIG. 3A is a heatmap of 273 differentially immunogenic proteins between healthy controls (HC) and Crohn's Disease (CD) samples identified by SAM analysis. Yellow and blue colors indicate high and low immunogenic response, respectively. FIG. 3B is a heatmap of the 188 differentially immunogenic proteins between Crohn's Disease and ulcerative colitis samples identified by SAM analysis; and FIG. 3C illustrates 33 differentially immunogenic proteins between healthy controls and ulcerative colitis samples as identified by SAM analysis. Each row corresponds to a protein and each column corresponds to a sample. The expression level for each protein is normalized across the samples such that the mean is 0 and the standard deviation is 1. Blue and yellow indicates high and low immunogenic proteins, respectively. FIG. 3D is a Venn diagram of these differentially immunogenic proteins showing only limited overlapping among healthy control vs Crohn's Disease vs ulcerative colitis.

FIG. 5A depicts the classifier for healthy control vs Crohn's Disease (yellow=CD, blue=HC). For example, if immungenic reaction against era is >ybaN, the subject is identified as having Crohn's Disease and shows as yellow (light shading). If not, then its indicative of a healthy control (blue) (dark shading). FIG. 5B displays healthy control vs. ulcerative colitis classifier (yellow=ulcerative colitis, blue=healthy control). For example, if immungenic reaction against relE is >cysE_wcaB, the subject is identified as having ulcerative colitis and shows as yellow, If not, then its indicative of it is classified as a healthy control (blue). FIG. 5C shows the Crohn's Disease vs. ulcerative colitis classifier (yellow=ulcerative colitis, blue=Crohn's Disease). If frvX is ≥yidX, it is a ulcerative colitis (yellow), or else a CD (blue). See representative images of some of those protein pairs in FIG. 2.

FIG. 6C shows that immunogenic reactivity to era or ybaN alone (the top scoring pair in the HC vs CD k-TSP classifier) does not allow for class separation of the data; no threshold level would clearly separate healthy controls from Crohn's Disease. However, the ratio of the two features (top-scoring pair ratio) results in clear separation in the data lending well to classification FIG. 6C. Similar results were found when scatter plot analysis were done for the other two TSP pairs from the HC vs Crohn's Disease classifier as shown in FIG. 5A.

DETAILED DESCRIPTION OF THE INVENTION

Figure 1:
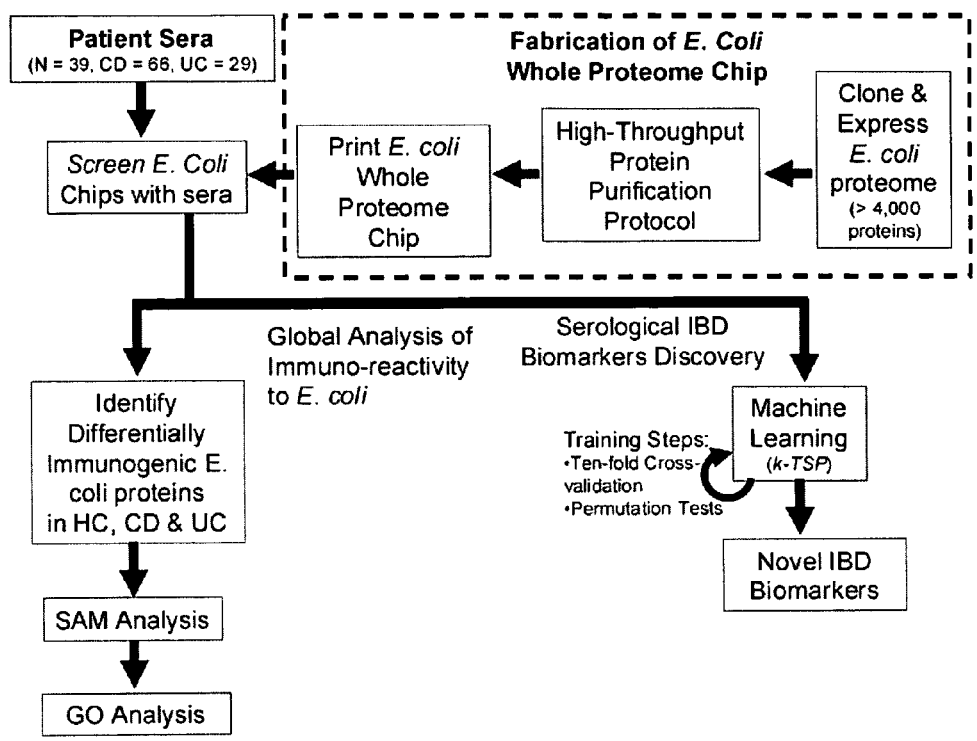
FIG. 1 is a schematic diagram showing the overall strategy used for the identification of novel serological biomarkers for inflammatory bowel disease using *E. coli* whole proteome chip. To fabricate the whole proteome chip, >4,000 *E. coli* proteins were cloned and expressed. These proteins were purified using high-throughput protein purification protocol and printed onto FullMoon slides using a ChipWriter Pro robot. 134 patient sera were collected from the Johns Hopkins Hospital for this analysis. These sera were screen by *E. coli* proteome chips. Two-level of data analyses were performed: (i) global IBD analysis was performed to identify differentially immunogenic proteins in healthy control, CD and ulcerative colitis using Significance Analysis of Microarray (SAM) and Gene Ontology (GO) enrichment analysis; and (ii) serological IBD biomarkers discovery using k-TSP algorithm.

The present invention provides biomarkers for use in serological testing for inflammatory bowel disease, and methods of using such markers to distinguish among intestinal disorders and selected effective therapies.

The invention is based, at least in part, on the discovery of new serological markers using a whole E. coli proteome microarray as a novel high-throughput proteomic approach to screening and identifying IBD markers. Each protein array, which contains 4,256 E. coli K12 proteins, was screened using individual serum from healthy controls (n=39) and clinically well-characterized patients with IBD [66 Crohn's disease (CD) and 29 ulcerative colitis (UC)]. Proteins that could be recognized by serum antibodies were visualized and quantified using Cy3-labeled goat anti-human antibodies. Surprisingly, SAM (significant analysis of microarray) analysis identified a total of 417 E. coli proteins that were differentially recognized by serum antibodies between healthy controls and Crohn's Disease or ulcerative colitis. Among those, 169 proteins were identified as highly immunogenic in healthy controls, 186 proteins are highly immunogenic in Crohn's Disease, only 19 in ulcerative colitis. Using a supervised learning algorithm (k-Top Scoring Pairs), two sets of serum antibodies were identified that were novel biomarkers for specifically distinguishing Crohn's Disease from healthy controls (accuracy: 86±4%; p<0.01), and Crohn's Disease from ulcerative colitis (accuracy: 80±2%; p<0.01), respectively. The Set 1 antibodies recognized three pairs of E. coli proteins: era vs ybaN, yhgN vs focA, and gabT vs ycdG and the Set 2 antibodies recognized yidX vs frvX. The specificity and sensitivity of Set 1 antibodies were 81±5% and 89±3%, respectively, while those of set 2 antibodies were 84±1% and 70±6%, respectively. Serum antibodies identified for distinguishing healthy controls vs ulcerative colitis were only marginal, since their accuracy, specificity and sensitivity were 66±5%, 69±5%, and 61±7%, respectively (p<0.04). Taken together, novel sets of serological biomarkers have been identified for diagnosis of Crohn's disease vs healthy control and Crohn's disease vs ulcerative colitis.

The use of biomarkers is particularly important because Crohn's disease and ulcerative colitis share many symptoms, both clinically and histologically. This makes the diagnosis of these two diseases difficult. The differences between Crohn's disease and ulcerative colitis exist at many levels. Crohn's disease may occur anywhere along the digestive tract from the mouth to the anus (although in most cases distal ileum and colon are affected). In ulcerative colitis, the large intestine (colon) is typically the only site that is affected. Second, the pattern of inflammation may be different. Ulcerative colitis tends to be continuous throughout the inflamed area, while Crohn's disease exhibits skipped lessions or ranulomas (intermittent patterns between inflamed and healthy-looking tissues. Third, there can be difference in the degree of tissue penetration. In ulcerative colitis, the colonic mucosal lining is ulcerated, but this does not extend beyond the mucosal lining. In Crohn's, such ulceration is typically deeper and may extend to virtually any layers of colon wall. Finally, the complications associated with the disease may differ. In Crohn's disease patients may experience complications, such as fistulizing and structuring. These complications are much less frequent in ulcerative colitis. In up to 15% Crohn's patients, extra-intestinal manifestations of disease can also occur. These may include inflammation in tissues or organs outside the gastrointestinal tract. Interesting general, smoking is bad and of a risk factor for Crohn's disease but protective or therapeutic for UC.

Inflammatory Bowel Disease

Serological testing is a non-invasive method for diagnosing IBD, and differentiating ulcerative colitis from Crohn's disease (Li et al., (2008) World J. Gastroenterol. 14, 5115-5124; Peyrin-Biroulet et al. (2007) Inflamm. Bowel. Dis. 13, 1561-1566; Vermeire et al. (2008) Gastroenterol. Clin. North Am. 37, 429-438). Several serological IBD biomarkers have been identified in the past decade, and some have been used in the clinics of IBD (Li et al., (2008) World J. Gastroenterol. 14, 5115-5124; Peyrin-Biroulet et al. (2007) Inflamm. Bowel. Dis. 13, 1561-1566; Vermeire et al. (2008) Gastroenterol. Clin. North Am. 37, 429-438). Many of these antibodies are produced on intestinal exposure to normal commensal bacteria in genetically susceptible individuals. Although it is not known whether these antibodies are pathogenic or not, they are specific to patients with either Crohn's disease or ulcerative colitis, and may reflect a dysregulated immune inflammatory response to intestinal bacterial antigens (Xavier (2007) Nature 448, 427-434, Strober (2002) Annu. Rev. Immunol. 20, 495-549; Blumberg (1999) Curr. Opin. Immunol. 11, 648-656; Papp et al., (2007) Inflamm. Bowel. Dis. 13, 984-992). Work on several experimental animal models of IBD have led to the suggestion that the pathogenesis of IBD may be the result of an aberrant immune response to normal commensal bacteria in genetically susceptible individuals. In fact, most of the major serological biomarkers being used in IBD clinics are antibodies to microbial antigens, including yeast oligomanna (anti-*Saccharomyces cerevisiae*, ASCA), bacterial outer membrane porin C (OmpC), *Pseudomonas fluorescens* bacterial sequence I2 (anti-I2), and most recently bacterial flagellin (CBir 1) ((Li et al., (2008) World J. Gastroenterol. 14, 5115-5124; Peyrin-Biroulet et al. (2007) Inflamm. Bowel. Dis. 13, 1561-1566; Vermeire et al. (2008) Gastroenterol. Clin. North Am. 37, 429-438)). All of these antimicrobial antibodies show preponderance in patients with Crohn's Disease. However, ASCA has been identified in up to 5% of patients with ulcerative colitis.

In comparison, IBD-specific pANCA or antineutrophil cytoplasmic antibody with perinuclear highlighting was first described in 1990. Although generally considered an autoantibody, the specific antigenic stimulation for pANCA production remains unclear. This auto-antibody is present in up to 70% of patients with ulcerative colitis, and in up to 20% of patients with CD. Recently, a panel of five new anti-glycan antibodies have been identified, including anti-chitobioside IgA (ACCA), anti-laminaribioside IgG (ALCA), anti-manobioside IgG (AMCA), and antibodies against chemically synthesized ($\Sigma$) two major oligomannose epitopes, Man $\alpha$-1,3 Man $\alpha$-1,2 Man ($\Sigma$Man3) and Man $\alpha$-1,3 Man $\alpha$-1,2 Man $\alpha$-1,2 Man ($\Sigma$Man4) (Li (2008) World J. Gastroenterol. 14, 5115-5124, 13, 15). If desired, these conventional biomarkers may be used in combination with the new serological biomarkers delineated herein (e.g., FIG. 5 and Tables 2-5, and 7).

Collectively, these antibodies are not generally present in either children or adults with non-IBD disease, and may represent serological markers of intestinal inflammation specific to ulcerative colitis or Crohn's disease. Though encouraging, none of the current commercially available biomarker tests/assays, including all of those mentioned above, can be used as stand-alone tools in clinics, and therefore they are currently only recommended as an adjunct to endoscopy in diagnosis and prognosis of the disease (Li (2008) World J. Gastroenterol. 14, 5115-5124; 16, 17). Therefore, additional specific and sensitive IBD biomarkers are needed.

Proteomic technologies, such as 2-dimensional gel electrophoresis, various variations of mass spectrometry and protein chip (array) technology are now proving to be powerful tools in biomarker discovery and are beginning to be utilized in IBD biomarker discovery (Li (2008) World J. Gastroenterol. 14, 5115-5124; 18). These technologies enable robust, and/or large-scale and high-throughput identification and analysis of differential protein expression when comparing disease to control. Blood-based (serum or plasma-based) proteomics hold particular promises for biomarker discovery of various human diseases such as neurodegenerative diseases and cancers (Goldknopf (2008) Expert Rev. Proteomics. 5, 1-8; Maurya et al., (2007) Anticancer Res. 27, 1247-1255; Veenstra et al. (2005) 4, 409-418.-21). Antigen microarrays are also powerful tools that allow high-throughput serum analysis of aberrant immune responses in autoimmune diseases, as well as efficient discovery of biomarkers for infectious pathogens. The present invention provides methods of using an *E coli* proteome microarray to characterize differential immune responses (serum anti-*E. coli* antibodies) among patients clinically classified as having Crohn's disease, ulcerative colitis and healthy controls. In addition, the invention provides novel IBD-specific anti microbial antibodies, particularly anti-*E. coli* antibodies, which are present in IBD patients and were identified by screening the sera with *E. coli* protein arrays.

Serum Antibody Biomarkers

The present invention provides serum antibody biomarkers that are differentially present in subjects having an inflammatory bowel disease, such as Crohn's disease or ulcerative colitis. These serum antibody biomarkers specifically bind to particular *E. coli* polypeptides, which are delineated in FIG. 5 and Tables 2-5, and 7. In particular, the invention provides that serum antibody biomarkers of the invention may be used individually or in combination with other markers to provide a method of diagnosing an inflammatory bowel disease. In one embodiment, the diagnosis of an inflammatory bowel disease involves distinguishing an inflammatory bowel disease from healthy controls. In certain embodiments, biomarkers comprises the pairs and sets of *E. coli* polypeptides delineated in FIGS. 5A, 5B, and 5C and Table 7 and the corresponding serum antibodies. In another embodiment, the diagnosis of an inflammatory bowel disease involves distinguishing Crohn's disease from ulcerative colitis. The invention further provides methods for selecting or monitoring the efficacy of a therapeutic regimen in a subject having a inflammatory bowel disease. Inflammatory bowel diseases include, but are not limited to Crohn's disease, ulcerative colitis, and indeterminate colitis.

Serum antibody biomarkers that are differentially present in samples of subjects having a inflammatory bowel disease and healthy control subjects find application in methods and kits for diagnosing an inflammatory bowel disease, such as Crohn's disease or ulcerative colitis, or distinguishing inflammatory bowel disease from healthy control. Accordingly, methods are provided for identifying inflammatory bowel disease in a subject, which involve detecting a differential presence of a serum antibody biomarker in subjects with a inflammatory bowel disease in a biological sample (e.g., blood, sera, plasma) obtained from the subject. The amount of one or more serum antibody biomarkers found in a test sample compared to a control, or the presence or absence of one or more serum antibody biomarkers in the test sample provides useful information regarding the inflammatory bowel disease status of the patient.

The serum antibody biomarkers can be measured in different types of biological samples. Preferably, the sample is a blood sample.

Detection Methods

The invention provides methods of detecting one or more serum antibody biomarkers associated with a inflammatory bowel disease or control markers in a blood sample obtained from a subject. The invention specifically describes the use of immunoassays to detect serum antibody biomarkers that specifically bind certain polypeptides or that measure the relative immune reaction against certain polypeptides. For example, the invention provides for the detection of greater immunogenic reactivity to era than to ybaN, greater immunogenic reactivity to yhgN than to focA, and greater immunogenic reactivity to gabT than ycdG. When each of these differential immunogenic reactivities is present then the subject is identified as having Crohn's Disease. In another example, the detection of greater immunogenic reactivity to frvX than to yidX identifies a subject as having ulcerative colitis.

In other embodiments, the invention provides at Table 7 methods for distinguishing Crohn's disease, ulcerative colitis, and healthy controls. In particular, microarrays comprising *E. coli* polypeptides delineated herein are useful for measuring immunogenic reactivity present in subject sera. Measurements can be relative to the immunogenic reactivity of another *E. coli* polypeptide. In one embodiment, the method provides that the following pairs can be used to measure relative levels of immunogenic reactivity.

For example, era>ybaN=Crohn's disease (CD)

The sequence of *E. coli* polypeptides are known in the art and can be identified in public databases by searching on the gene or polypeptide name. For example, the *E. coli* era polypeptide is NCBI Reference Sequence: AAA03242.1. The amino acid sequence of an exemplary era polypeptide is provided below.

(SEQ ID NO: 1)

```
  1 msidksycgf iaivgrpnvg kstllnkllg qkisitsrka qttrhrivgi htegayqaiy
 61 vdtpglhmee krainrlmnk aasssigdve lvifvvegtr wtpddemvln klregkapvi
121 lavnkvdnvq ekadllphlq flasqmnfld ivpisaetgl nvdtiaaivr khlpeathhf
```

-continued

```
181 pedyitdrsq rfmaseiire klmrflgael pysvtveier fvsnerggyd inglilvere
241 gqkkmvignk gakiktigie arkdmqemfe apvhlelwvk vksgwadder alrslgyvdd
301 l
```

The sequence of an exemplary E. coli ybaN polypeptide (NCBI Reference Sequence: AP_001117.1) is provided below:

```
                                                          (SEQ ID NO: 2)
  1 mqriiliiig wlavvlgtlg vvlpvlpttp fillaawcfa rssprfhawl lyrswfgsyl
 61 rfwqkhhamp rgvkpraill illtfaislw fvqmpwvrim llvilacllf ymwripvide
121 kqekh
```

In another example, yhgN>focA=CD. The sequence of an exemplary E. coli yhgN (NCBI Reference Sequence: AP_004357) is provided below:

```
                                                          (SEQ ID NO: 3)
  1 mneiisaavl lilimdplgn lpifmsvlkh tepkrrraim vrelliallv mlvflfagek
 61 ilaflslrae tvsisggiil fliaikmifp sasgnssglp ageepfivpl aiplvagpti
121 latlmllshq ypnqmghlvi alllawggtf villqsslfl rllgekgvna lerlmglilv
181 mmatqmfldg irmwmkg
```

The sequence of an exemplary E. coli focA (NCBI Reference Sequence: AP_001534) is provided below:

```
                                                          (SEQ ID NO: 4)
  1 mkadnpfdll lpaamakvae eagvykatkh plktfylait agvfisiafv fyitattgtg
 61 tmpfgmaklv ggicfslgli lcvvcgadlf tstvlivvak asgritwgql aknwlnvyfg
121 nlvgallfvl lmwlsgeymt angqwglnvl qtadhkvhht fieavclgil anlmvclavw
181 msysgrslmd kafimvlpva mfvasgfehs ianmfmipmg ivirdfaspe fwtavgsape
241 nfshltvmnf itdnlipvti gniigggllv gltywviylr endhh
```

For example, gabT>ycdG=CD The sequence of an exemplary E. coli gabT (NCBI Reference Sequence: AP_003235.1) is provided below

```
                                                          (SEQ ID NO: 5)
  1 mnsnkelmqr rsgaiprgvg qihpifadra encrvwdveg reyldfaggi avlntghlhp
 61 kvvaaveaql kklshtcfqv layepylelc eimnqkvpgd fakktllvtt gseavenavk
121 iaraatkrsg tiafsgayhg rthytlaltg kvnpysagmg lmpghvyral ypcplhgise
181 ddaiasihri fkndaapedi aaiviepvqg eggfyasspa fmqrlralcd ehgimliade
241 vqsgagrtgt lfameqmgva pdlttfaksi aggfplagvt graevmdava pgglggtyag
301 npiacvaale vlkvfeqenl lqkandlgqk lkdgllaiae khpeigdvrg lgamiaielf
361 edgdhnkpda kltaeivara rdkglillsc gpyynvlril vpltiedaqi rqgleiisqc
421 fdeakq
```

The sequence of an exemplary E. coli ycdG (NCBI Reference Sequence: AP_001637.1) is provided below.

```
                                                                  (SEQ ID NO: 6)
  1 mamfgfphwq lkststesgv vapderlpfa qtavmgvqha vamfgatvlm pilmgldpnl 61 silmsgigtl lfffitggrv psylgssaaf vgvviaatgf ngqginpnis ialggiiacg 121 lvytviglvv mkigtrwier lmppvvtgav vmaiglnlap iavksysasa fdswmavmtv 181 lciglvavft rgmiqrllil vglivaclly gvmtnvlglg kavdftlvsh aawfglphfs 241 tpafngqamm liapvavilv aenlghlkav agmtgrnmdp ymgrafvgdg latmlsgsvg 301 gsgvttyaen igvmavtkvy stlvfvaaav iamllgfspk fgalihtipa aviggasivv 361 fgliavagar iwvqnrvdls qngnlimvav tlvlgagdfa ltlggftlgg igtatfgail 421 lnallsrklv dvpppevvhq ep
```

In other examples yidX (NCBI AP_004097)>frvX=UC; relE (NCBI ABD51640.1)>cysE/wcaB (NCBI CAQ33933.1)=UC; lnt (NCBI AP_001306.1)>ybiO (NCBI AP_001439.1)=UC; ftsE (NCBI AP_004329.1)>pssR (NCBI F65179)=UC; yhgN(NCBI AP_004357.1)>yhfG (NCBI AP_004427.1)=UC; yafN(NCBI AP_000885.1)>dsbB (NCBI AP_001810.1)=UC; yihI (NCBI AP_003942.1)>yabK (NCBI AAC73178.1)=UC 421#15>yhdN(NCBI AAC76318.1)=UC; hisP (NCBI AAC75366.1)>rp10 (NCBI AAC76326.1)=UC; cml (NCBI P12056.1)>nuoM (NCBI AP_002875.1)=UC; yieC(NCBI AAC76743.1)>nuoI (NCBI AP_002879.1)=UC.

One of skill in the art will recognize that any suitable method can be used to detect the serum antibody biomarkers described herein. Successful practice of the invention can be achieved with one or a combination of methods that can detect and/or quantify the markers. Such methods include, without limitation, hybridization-based methods including those employed in microarrays, mass spectrometry (e.g., laser desorption/ionization mass spectrometry), fluorescence (e.g. sandwich immunoassay), surface plasmon resonance, ellipsometry, atomic force microscopy, and 2-dimensional gel electrophoresis. Methods may further include, one or more of electrospray ionization mass spectrometry (ESI-MS), ESI-MS/MS, ESI-MS/(MS)$_n$, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APC)-MS), atmospheric pressure photoionization mass spectrometry (APPI-MS), quadrupole mass spectrometry, fourier transform mass spectrometry (FTMS), and ion trap mass spectrometry. In one preferred embodiment, detection methods employ a microchip array comprising immunogenic pathogen (e.g., E. coli) polypeptides.

Microarrays

As described herein, collections of immunogenic E. coli polypeptides may be used to identify serum antibody biomarker profiles that are associated with inflammatory bowel disease. These collections preferably include polypeptides that are differentially immunogenic (e.g., polypeptides that induce serum antibody biomarkers in healthy controls, but not in inflammatory bowel disease, or polypeptides that induce serum antibody biomarkers in inflammatory bowel disease or ulcerative colitis, but not in healthy controls). Such polypeptides of the invention are useful as hybridizable array elements in a microarray. Polypeptides useful in arrays of the invention include, but are not limited to, those polypeptides delineated in FIG. 5 and Tables 2-5, and 7. The array elements are organized in an ordered fashion such that each element is present at a specified location (i.e., an addressable location) on the substrate. Useful substrate materials include membranes, composed of paper, nylon or other materials, filters, chips, glass slides, and other solid supports. The ordered arrangement of the array elements allows hybridization patterns and intensities to be interpreted as levels of particular serum antibody biomarkers. Methods for making polypeptide microarrays are described, for example, by Ge (Nucleic Acids Res. 28: e3. i-e3. vii, 2000), MacBeath et al., (Science 289:1760-1763, 2000), Zhu et al. (Nature Genet. 26:283-289), and in U.S. Pat. No. 6,436,665, hereby incorporated by reference.

Serum antibody biomarkers associated with inflammatory bowel disease may be analyzed using protein microarrays comprising the entire E. coli proteome, or comprising as few as one, two, three, four, five, or six E. coli proteins. Typically, protein microarrays feature a protein, or fragment thereof, bound to a solid support. Suitable solid supports include membranes (e.g., membranes composed of nitrocellulose, paper, or other material), polymer-based films (e.g., polystyrene), beads, or glass slides. For some applications, proteins are spotted on a substrate using any convenient method known to the skilled artisan (e.g., by hand or by inkjet printer). Preferably, such methods retain the biological activity or function of the protein bound to the substrate (Ge et al., supra; Zhu et al., supra).

The protein microarray is hybridized with blood, serum, or plasma derived from a subject. The sample comprises antibodies that specifically bind an E. coli polypeptide, thereby acting as probes. Probes can also include antibodies, candidate peptides, nucleic acids, or small molecule compounds derived from a peptide, nucleic acid, or chemical library. Hybridization conditions (e.g., temperature, pH, protein concentration, and ionic strength) are optimized to promote specific interactions. Such conditions are known to the skilled artisan and are described, for example, in Harlow, E. and Lane, D., Using Antibodies: A Laboratory Manual. 1998, New York: Cold Spring Harbor Laboratories. After removal of non-specific probes, specifically bound probes are detected, for example, by fluorescence, enzyme activity (e.g., an enzyme-linked calorimetric assay), direct immunoassay, radiometric assay, or any other suitable detectable method known to the skilled artisan.

The biochip surfaces may, for example, be ionic, anionic, hydrophobic; comprised of immobilized nickel or copper ions, comprised of a mixture of positive and negative ions; and/or comprised of one or more antibodies, single or double stranded nucleic acids, proteins, peptides or fragments thereof, amino acid probes, or phage display libraries. Many protein biochips are described in the art. These include, for example, protein biochips produced by Ciphergen Biosystems (Fremont, Calif.), Packard BioScience Company (Meriden Conn.), Zyomyx (Hayward, Calif.) and Phylos (Lexington, Mass.). Examples of such protein biochips are described in the following patents or patent applications: U.S. Pat. No. 6,225,047 (Hutchens and Yip, "Use of retentate chromatography to generate difference maps," May 1, 2001); International publication WO 99/51773 (Kuimelis and Wagner, "Addressable protein arrays," Oct. 14, 1999); U.S. Pat. No. 6,329,209 (Wagner et al., "Arrays of protein-capture agents and methods of use thereof," Dec. 11, 2001) and International publication WO 00/56934 (Englert et al., "Continuous porous matrix arrays," Sep. 28, 2000).

Serum antibody biomarkers may be captured with capture reagents (e.g., target polypeptides) immobilized to a solid support, such as a biochip, a multiwell microtiter plate, a resin, or nitrocellulose membranes that are subsequently probed for the presence of proteins. Capture can be on a chromatographic surface or a biospecific surface. For example, a serological sample containing the serum antibody biomarkers may be contacted with the active surface of a biochip for a sufficient time to allow binding. Then, unbound molecules are washed from the surface using a suitable eluant, such as phosphate buffered saline. In general, the more stringent the eluant, the more tightly the proteins must be bound to be retained after the wash.

Upon capture on a biochip, analytes can be detected by a variety of detection methods selected from, for example, a gas phase ion spectrometry method, an optical method, an electrochemical method, atomic force microscopy and a radio frequency method. Gas phase ion spectrometry methods are described herein. Of particular interest is the use of mass spectrometry, and in particular, SELDI. Optical methods include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Immunoassays in various formats (e.g., ELISA) are popular methods for detection of analytes captured on a solid phase. Electrochemical methods include voltametry and amperometry methods. Radio frequency methods include multipolar resonance spectroscopy.

Mass spectrometry (MS) is a well-known tool for analyzing chemical compounds. Thus, in one embodiment, the methods of the present invention comprise performing quantitative MS to measure serum antibody biomarkers present in a serological sample. The method may be performed in an automated (Villanueva, et al., *Nature Protocols* (2006) 1(2): 880-891) or semi-automated format. This can be accomplished, for example with MS operably linked to a liquid chromatography device (LC-MS/MS or LC-MS) or gas chromatography device (GC-MS or GC-MS/MS). Methods for performing MS are known in the field and have been disclosed, for example, in US Patent Application Publication Nos: 20050023454; 20050035286; U.S. Pat. No. 5,800,979 and references disclosed therein.

The protein fragments, whether they are peptides derived from the main chain of the protein or are residues of a side-chain, are collected on the collection layer. They may then be analyzed by a spectroscopic method based on matrix-assisted laser desorption/ionization (MALDI) or electrospray ionization (ESI). The preferred procedure is MALDI with time of flight (TOF) analysis, known as MALDI-TOF MS. This involves forming a matrix on the membrane, e.g. as described in the literature, with an agent which absorbs the incident light strongly at the particular wavelength employed. The sample is excited by UV, or IR laser light into the vapour phase in the MALDI mass spectrometer. Ions are generated by the vaporization and form an ion plume. The ions are accelerated in an electric field and separated according to their time of travel along a given distance, giving a mass/charge (m/z) reading which is very accurate and sensitive. MALDI spectrometers are commercially available from PerSeptive Biosystems, Inc. (Frazingham, Mass., USA) and are described in the literature, e.g. M. Kussmann and P. Roepstorff, cited above.

Diagnostics

Levels of particular serum antibody biomarkers have been correlated with a particular inflammatory bowel disease state, and thus are useful in diagnosis. In one embodiment, a patient having a inflammatory bowel disease will show an alteration in the expression of one or more serum antibody biomarkers delineated herein. In another embodiment, a patient having a inflammatory bowel disease will have a particular expression profile that includes significantly altered expression of two or more serum antibody biomarkers. Alterations in serum antibody biomarkers levels are detected using methods known to the skilled artisan and described herein. If desired, biomarkers delineated herein are used alone or in combination with convention biomarkers, which include anti-glycan antibodies (e.g., anti-chitobioside IgA (ACCA), anti-laminaribioside IgG (ALCA), anti-manobioside IgG (AMCA)), antibodies against chemically synthesized ($\Sigma$) two major oligomannose epitopes, Man $\alpha$-1,3 Man $\alpha$-1,2 Man ($\Sigma$Man3) and Man $\alpha$-1,3 Man $\alpha$-1,2 Man $\alpha$-1,2 Man ($\Sigma$Man4) (Li (2008) World J. Gastroenterol. 14, 5115-5124; 13, 15), IBD-specific pANCA or antineutrophil cytoplasmic antibody, antibodies to microbial antigens (e.g., yeast oligomanna (anti-*Saccharomyces cerevisiae*, ASCA), bacterial outer membrane porin C (OmpC), *Pseudomonas fluorescens* bacterial sequence I2 (anti-I2), and antibodies against bacterial flagellin).

In one embodiment, *E. coli* polypeptides or fragments derived from these polypeptides may be used as targets in a microarray. The microarray is used to assay the level of large numbers of serum antibody biomarkers simultaneously and to identify alterations in the overall or relative levels of expression. Such information can be used to diagnose a inflammatory bowel disease or a subject having a propensity to develop such a condition.

In one embodiment, an increased level of a serum antibody biomarker that specifically binds frvX relative to the level of serum antibody biomarker that binds yidX identifies a subject as having ulcerative colitis. In another embodiment an increased level of serum antibody biomarker binding to era relative to ybaN, increased serum antibody biomarker binding to yhgN relative to focA, and/or increased serum antibody biomarker binding to gabT relative to ycdG identifies a subject as having Crohn's Disease. A variety of protocols for measuring an alteration in the expression of such polypeptides are known, including immunological methods (such as ELISAs and RIAs), and provide a basis for diagnosing an inflammatory bowel disease.

In additional embodiment of the methods of the present invention, multiple markers are measured. The use of multiple markers increases the predictive value of the test and provides greater utility in diagnosis, treatment selection, patient stratification and patient monitoring. The process detects serum antibody biomarker profiles formed by the analysis of multiple markers. Such analysis may improve the sensitivity and specificity of tests delineated herein. Subtle variations in data from clinical samples indicate that certain patterns of serum antibody biomarker expression can predict phenotypes such as the presence or absence of a certain disease, a particular stage of disease progression, or a positive or adverse response to drug treatments.

Data generated by detection of serum antibody biomarkers can be analyzed using any suitable means. In one embodiment, data is analyzed with the use of a programmable digital computer. The computer program generally contains a readable medium that stores data. This data can indicate the number of serum antibody biomarkers detected, including the strength of the signal generated by each marker. Data analysis can include the steps of determining signal strength of a marker detected. When the sample is measured and data is generated, the data is then analyzed by a computer software program As indicated above, the invention provides methods for aiding a human inflammatory bowel disease diagnosis using one or more serum antibody biomarkers, as specified herein. These markers can be used alone, in combination with other markers in any set, or with entirely different markers in aiding human inflammatory bowel disease diagnosis. The serum antibody biomarkers are differentially present in samples of a subject having or having a propensity to develop a inflammatory bowel disease and a healthy control subject in whom inflammatory bowel disease is undetectable. For example, some of the serum antibody biomarkers are expressed at an elevated level and/or are present at a higher frequency in human inflammatory bowel disease subjects than in normal subjects, while some of the serum antibody biomarkers are expressed at a decreased level and/or are present at a lower frequency in human inflammatory bowel disease subjects than in normal subjects. Therefore, detection of one or more of these markers in a person would provide useful information regarding the probability that the person may have an inflammatory bowel disease.

The detection of a marker is then correlated with a probable diagnosis of inflammatory bowel disease. In some embodiments, the detection of the mere presence or absence of a marker, without quantifying the amount thereof, is useful and can be correlated with a probable diagnosis of inflammatory bowel disease. The measurement of markers may also involve quantifying the markers to correlate the detection of markers with a probable diagnosis of inflammatory bowel disease. Thus, if the amount of the markers detected in a subject being tested is different compared to a control amount (i.e., higher or lower than the control, depending on the marker), then the subject being tested has a higher probability of having inflammatory bowel disease.

The correlation may take into account the amount of the serum antibody biomarkers in the sample compared to a control amount of the serum antibody biomarkers (up or down regulation of the marker or markers) in normal subjects or in subjects where inflammatory bowel disease is undetectable. A control can be, e.g., the average or median amount of marker present in comparable samples of normal subjects. The control amount is measured under the same or substantially similar experimental conditions as in measuring the test amount. As a result, the control can be employed as a reference standard, where the normal phenotype is known, and each result can be compared to that standard, rather than re-running a control.

Accordingly, a serum antibody biomarkers profile may be obtained from a subject sample and compared to a reference marker profile obtained from a reference population, so that it is possible to classify the subject as belonging to or not belonging to the reference population. The correlation may take into account the presence or absence of the markers in a test sample and the frequency of detection of the same markers in a control. The correlation may take into account both of such factors to facilitate determination inflammatory bowel disease status.

Any marker, individually, is useful in aiding in the determination of inflammatory bowel disease status. First, the selected serum antibody biomarkers is detected in a subject sample using the methods described herein (e.g. microarray analysis). Then, the result is compared with a control that distinguishes inflammatory bowel disease status from non-inflammatory bowel disease status. As is well understood in the art, the techniques can be adjusted to increase sensitivity or specificity of the diagnostic assay depending on the preference of the diagnostician.

While individual serum antibody biomarkers are useful diagnostic markers, in some instances, a combination of markers provides greater predictive value than single markers alone. The detection of a plurality of markers (or absence thereof, as the case may be) in a sample can increase the percentage of true positive and true negative diagnoses and decrease the percentage of false positive or false negative diagnoses. Thus, one method of the present invention provides for the measurement of more than one marker.

Optionally, methods described herein may be combined with any conventional method for the diagnosis of IBD (e.g., stool sample analysis, colonoscopy or sigmoidoscopy, barium x-ray, computerized axial tomography, and or capsule endoscopy).

Monitoring

Methods of characterizing inflammatory bowel disease in a subject are also useful in managing subject treatment based on the subject's status. The invention provides for such methods where the serum antibody biomarkers (or specific combinations of markers) are measured before and again after subject management. In these cases, the methods are used to monitor the status of the inflammatory bowel disease, e.g., response to inflammatory bowel disease treatment, amelioration of the disease or progression of the disease.

Figure 5:
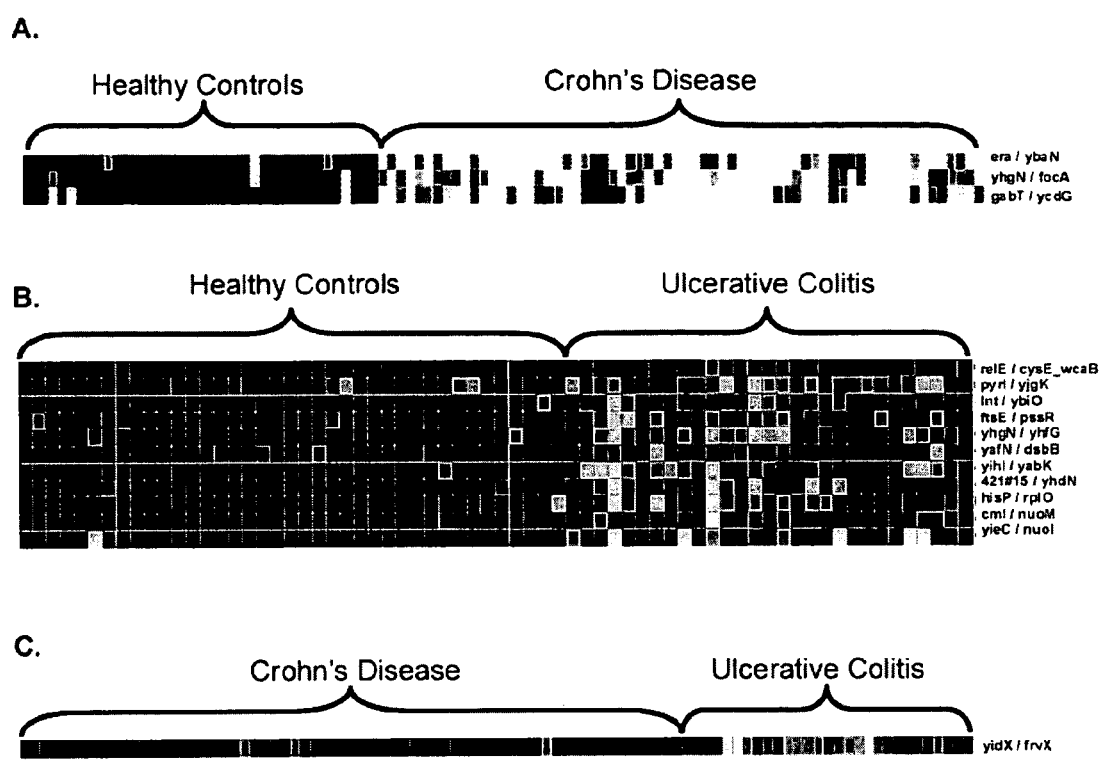
FIG. 5 includes three heat maps showing that k-TSP identified the top three pairs of biomarkers that can discriminate controls from Crohn's Disease patients. Each column represents the immunogenic reactivity by individual IBD patients or healthy control. Within a column, each row represents ratio of the immunogenic reactivity of a top scoring pair of proteins. The expression values represented are the ratio of immunogenic reactivity (fluorescent signal or intensity) to protein X divided by the signals to protein Y, referred to as the TSP ratio (X and Y being example proteins). If the immunogenic reactivity of a patient to protein X was greater than the reactivity to protein Y, the box will appear yellow, and blue for vice versa (see examples below).

For example, markers of the invention (e.g., antibodies that bind an *E. coli* polypeptide listed in FIG. 5 and Tables 2-5, and 7) can be used to monitor a subject's response to certain treatments of inflammatory bowel disease. The level or function of a marker delineated herein may be measured before treatment, during treatment, or following the conclusion of a treatment regimen. Preferably, multiple measurements (e.g., 2, 3, 4, 5) are made at one or more of those times. Measurements are made, for example, using an immunoassay, microarray or other method to determine the expression profile of one or more serum antibody biomarkers. Such monitoring may be useful, for example, in assessing the efficacy of a particular drug in a patient. Therapeutics that normalize the levels of a serum antibody biomarker (e.g., that increase or reduce levels to correspond to levels present in a healthy control subject) are taken as particularly useful in the invention.

Kits

In one aspect, the invention provides kits for monitoring and diagnosing inflammatory bowel disease, wherein the kits can be used to detect the markers described herein. For example, the kits can be used to detect any one or more of the markers differentially present in samples of inflammatory bowel disease subjects vs. normal subjects. If desired a kit of the invention includes any one or more of the *E. coli* polypeptides listed in FIG. 5 and Tables 2-5, and 7. In one embodiment, the kit comprises a set of biomarkers for distinguishing Crohn's Disease from healthy control, the set comprising era, ybaN, yhgN, focA, ga bT and ycdG. In another embodiment, the kit comprises the set of biomarkers for distinguishing Crohns from UC, which is yidx/frvx. If desired, the kit comprises reagents suitable for measuring conventional IBD biomarkers, including anti-glycan antibodies (e.g., anti-chitobioside IgA (ACCA), anti-laminaribioside IgG (ALCA), anti-manobioside IgG (AMCA)), antibodies against chemically synthesized (Σ) two major oligomannose epitopes, Man α-1,3 Man α-1,2 Man (ΣMan3) and Man α-1,3 Man α-1,2 Man α-1,2 Man (ΣMan4) (Li (2008) World J. Gastroenterol. 14, 5115-512413, 15), IBD-specific pANCA or antineutrophil cytoplasmic antibody, antibodies to microbial antigens (e.g., yeast oligomanna (anti-*Saccharomyces cerevisiae*, ASCA), bacterial outer membrane porin C (OmpC), *Pseudomonas fluorescens* bacterial sequence I2 (anti-I2), and antibodies against bacterial flagellin (Cbir).

The kits of the invention have many applications. For example, the kits can be used to distinguish between inflammatory bowel disease and control, to determine if a subject has a Crohn's Disease or ulcerative colitis, or to determine that the subject does not have inflammatory bowel disease, thus aiding in inflammatory bowel disease diagnosis. The kits can also be used to identify compounds that modulate expression of one or more of the serum antibody biomarkers in an animal model of inflammatory bowel disease.

The kits of the invention may include instructions for the assay, reagents, testing equipment (test tubes, reaction vessels, needles, syringes, etc.), standards for calibrating the assay, and/or equipment provided or used to conduct the assay. Reagents may include acids, bases, oxidizing agents, marker species. The instructions provided in a kit according to the invention may be directed to suitable operational parameters in the form of a label or a separate insert.

The kits may also include an adsorbent, wherein the adsorbent retains one or more markers selected from one or more of the markers described herein, and written instructions for use of the kit for detection of an inflammatory bowel disease. Such a kit could, for example, comprise: (a) a substrate comprising an adsorbent thereon, wherein the adsorbent is suitable for binding a serum antibody biomarkers, and (b) instructions to detect the serum antibody biomarkers by contacting a sample with the adsorbent and detecting the serum antibody biomarkers retained by the adsorbent. Accordingly, the kit could further comprise a detection reagent.

Optionally, the kit may further comprise a standard or control information so that the test sample can be compared with the control information standard to determine if the test amount of a marker detected in a sample is a diagnostic amount consistent with a diagnosis of inflammatory bowel disease.

Selection of a Treatment Method

After a subject is diagnosed as having inflammatory bowel disease a method of treatment is selected. Because inflammatory bowel disease typically involves an excessive or undesirable immune response, therapies often involve treatment with immunosuppressive agents. Such therapies would not be appropriate for a subject that has irritable bowel syndrome. Thus, the invention provides methods for selecting an appropriate therapy for a subject, the method involving identifying a subject as having inflammatory bowel disease, Crohn's disease or ulcerative colitis, and administering to the subject a therapeutic treatment appropriate for that disease. Exemplary treatments for IBD include but are not limited to aminosalicylates, immunomodulators, infliximab, adalimumab, certolizumab, and/or antibiotics.

Biomarkers identified herein are useful for identifying subjects in need of surgery. In particular embodiments, pairs and sets of biomarkers delineated in Tables 2-5, 7, and FIG. 5 are useful alone or in combination with existing biomarkers to identify subjects that could benefit from surgery.

*E. coli* Polypeptides and Analogs

Also included in the invention are *E. coli* polypeptides or fragments thereof that are modified in ways that enhance or do not inhibit their ability to bind a serum antibody. In one embodiment, the invention provides methods for optimizing an *E. coli* amino acid sequence or nucleic acid sequence by producing an alteration. Such changes may include certain mutations, deletions, insertions, or post-translational modifications. In one preferred embodiment, the *E. coli* amino acid sequence is modified to enhance protease resistance. Accordingly, the invention further includes polypeptides of other yeast or bacteria having at least 85%, 90%, 95% or greater sequence identity to an *E. coli* polypeptide delineated herein. In other embodiments, the invention includes analogs of any naturally-occurring polypeptide of the invention. Analogs can differ from the naturally-occurring polypeptide of the invention by amino acid sequence differences, by post-translational modifications, or by both. Analogs of the invention will generally exhibit at least 85%, more preferably 90%, and most preferably 95% or even 99% identity with all or part of a naturally-occurring amino, acid sequence of the invention. The length of sequence comparison is at least 10, 13, 15 amino acid residues, preferably at least 25 amino acid residues, and more preferably more than 35 amino acid residues. Again, in an exemplary approach to determining the degree of identity, a BLAST program may be used, with a probability score between $e^{-3}$ and $e^{-100}$ indicating a closely related sequence. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the invention by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., .beta. or .gamma. amino acids.

In addition to full-length polypeptides, the invention also includes fragments of any one of the polypeptides of the invention. As used herein, the term "a fragment" means at least 5, 10, 13, or 15 amino acids in length. In other embodiments a fragment is at least 20 contiguous amino acids, at least 30 contiguous amino acids, or at least 50 contiguous amino acids, and in other embodiments at least 60 to 80 or more contiguous amino acids. Fragments of the invention can be generated by methods known to those skilled in the art or may result from normal protein processing (e.g., removal of amino acids from the nascent polypeptide that are not required for biological activity or removal of amino acids by alternative mRNA splicing or alternative protein processing events).

Screening Assays

Methods of the invention are useful for the high-throughput low-cost screening of candidate agents that bind an *E. coli* polypeptide described herein. A candidate agent that specifically binds to a *E. coli* is then isolated and tested for activity in an in vitro assay or in vivo assay. If desired, the candidate agent comprises a detectable label. In one embodiment, such polypeptides are subsequently screened for an effect on bacterial proliferation or as agents that block antibody binding to a *E. coli* polypeptide listed herein. One skilled in the art appreciates that the effects of a candidate agent on a cell is typically compared to a corresponding control cell not contacted with the candidate agent. Thus, the screening methods include comparing the effect of a candidate agent with an untreated control cell.

In one embodiment, candidate compounds may be identified by first assaying those that specifically bind to an *E. coli* polypeptide of the invention. Such an interaction can be readily assayed using any number of standard binding techniques and functional assays (e.g., those described in Ausubel et al., supra). For example, a candidate compound may be tested in vitro for interaction and binding with a polypeptide of the invention and its ability to modulate bacterial proliferation may be assayed by any standard assays (e.g., those described herein)

In one particular example, a candidate compound that binds to an *E. coli* polypeptide may be identified using a chromatography-based technique. For example, a recombinant *E. coli* polypeptide of the invention may be purified by standard techniques from cells engineered to express the polypeptide, or may be chemically synthesized, once purified the peptide is immobilized on a column. A solution of candidate agents is then passed through the column, and an agent that specifically binds the polypeptide or a fragment thereof is identified on the basis of its ability to bind to the polypeptide and to be immobilized on the column. To isolate the agent, the column is washed to remove non-specifically bound molecules, and the agent of interest is then released from the column and collected. Agents isolated by this method (or any other appropriate method) may, if desired, be further purified (e.g., by high performance liquid chromatography). In addition, these candidate agents may be tested for their ability to reduce bacterial proliferation or block serum antibody binding to an *E. coli* polypeptide. Agents isolated by this approach may also be used, for example, as therapeutics to treat or prevent inflammatory bowel disease (e.g., Crohn's, ulcerative colitis). Compounds that are identified as binding to a an *E. coli* polypeptide with an affinity constant less than or equal to 1 nM, 5 nM, 10 nM, 100 nM, 1 mM or 10 mM are considered particularly useful in the invention.

Such agents may be used, for example, as a therapeutic to combat the pathogenicity of an bacterial pathogen. Optionally, agents identified in any of the above-described assays may be confirmed as useful in conferring protection against the development of a pathogen infection in any standard animal model and, if successful, may be used as antipathogen therapeutics.

Each of the protein sequences provided herein may also be used in the discovery and development of antipathogenic compounds (e.g., antibiotics). The *E. coli* protein, upon expression, can be used as a target for the screening of drugs to treat or prevent IBD.

Test Compounds and Extracts

In general, candidate agents are identified from large libraries of natural product or synthetic (or semi-synthetic) extracts or chemical libraries or from polypeptide or nucleic acid libraries, according to methods known in the art. Those skilled in the field of drug discovery and development will understand that the precise source of test extracts or compounds is not critical to the screening procedure(s) of the invention. Agents used in screens may include known those known as therapeutics for the treatment of pathogen infections. Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as the modification of existing polypeptides.

Libraries of natural polypeptides in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). Such polypeptides can be modified to include a protein transduction domain using methods known in the art and described herein. In addition, natural and synthetically produced libraries are produced, if desired, according to methods known in the art, e.g., by standard extraction and fractionation methods. Examples of methods for the synthesis of molecular libraries can be found in the art, for example in: DeWitt et al., *Proc. Natl. Acad. Sci. U.S.A.* 90:6909, 1993; Erb et al., *Proc. Natl. Acad. Sci. USA* 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33:2059, 1994; Carell et al., *Angew. Chem. Int. Ed. Engl.* 33:2061, 1994; and Gallop et al., *J. Med. Chem.* 37:1233, 1994. Furthermore, if desired, any library or compound is readily modified using standard chemical, physical, or biochemical methods.

Numerous methods are also available for generating random or directed synthesis (e.g., semi-synthesis or total synthesis) of any number of polypeptides, chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, chemical compounds to be used as candidate compounds can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Libraries of compounds may be presented in solution (e.g., Houghten, *Biotechniques* 13:412-421, 1992), or on beads (Lam, *Nature* 354:82-84, 1991), chips (Fodor, *Nature* 364:555-556, 1993), bacteria (Ladner, U.S. Pat. No. 5,223, 409), spores (Ladner U.S. Pat. No. 5,223,409), plasmids (Cull et al., *Proc Natl Acad Sci USA* 89:1865-1869, 1992) or on phage (Scott and Smith, *Science* 249:386-390, 1990; Devlin, *Science* 249:404-406, 1990; Cwirla et al. *Proc. Natl.*

*Acad. Sci.* 87:6378-6382, 1990; Felici, *J. Mol. Biol.* 222: 301-310, 1991; Ladner supra.).

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity should be employed whenever possible.

When a crude extract is found to have *E. coli* polypeptide binding activity further fractionation of the positive lead extract is necessary to isolate molecular constituents responsible for the observed effect. Thus, the goal of the extraction, fractionation, and purification process is the careful characterization and identification of a chemical entity within the crude extract that treats or prevents IBD or acts as an antibiotic. Methods of fractionation and purification of such heterogenous extracts are known in the art. If desired, compounds shown to be useful as therapeutics are chemically modified according to methods known in the art.

The present invention provides methods of treating inflammatory bowel disease and/or disorders or symptoms thereof which comprise administering a therapeutically effective amount of a pharmaceutical composition comprising a compound of the formulae herein to a subject (e.g., a mammal such as a human). Thus, one embodiment is a method of treating a subject suffering from or susceptible to a inflammatory bowel disease or disorder or symptom thereof. The method includes the step of administering to the mammal a therapeutic amount of an amount of a compound herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method). As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated. As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which inflammation of the intestine may be implicated.

In one embodiment, the invention provides a method of monitoring treatment progress. The method includes the step of determining a level of diagnostic marker (Marker) (e.g., any target delineated herein) or diagnostic measurement (e.g., screen, assay) in a subject suffering from or susceptible to a inflammatory bowel disease, or disorder or symptoms thereof associated with intestinal inflammation. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Identification of IBD Serological Markers from *E. coli* Proteome Chips

Sera was collected from 134 individuals (29 healthy control, 66 CD and 39 ulcerative colitis) from the Johns Hopkins Medical Institutes (Table 1).

TABLE 1

Demographic and clinical information of IBD Patient and healthy controls.

| Patient Data/Characteristics | CD (n = 66) | UC (n = 29) | HC (n = 39) |
| --- | --- | --- | --- |
| Gender: female % | 55 | 53 | 43 |
| Age: mean/st dev (yrs) | 36.7 ± 13.1 | 38 ± 14.5 | 47 ± 12.4 |
| Age at diagnosis: mean (yrs) | 36.7 | 28 | |

TABLE 1-continued

Demographic and clinical information of IBD Patient and healthy controls.

| Patient Data/Characteristics | CD (n = 66) | UC (n = 29) | HC (n = 39) |
|---|---|---|---|
| Duration of disease (yrs) | 12.3 | 8.9 | |
| Extraintestinal disease: n (%) | 7 (11) | 3 (10) | |
| Surgery: n (%) | 46 (70) | 4 (12) | |
| Ethnicity: n (%) | | | |
| African American | 29 (44) | 10 (34) | |
| Caucasian | 35 (53) | 22 (75) | |
| Hispanic | 2 (3) | 0 | |
| Smoking: n (%) | | | |
| Past or present | 17 (26) | 5 (17) | |
| Nonsmoker | 40 (60) | 18 (62) | |
| Unknown | 9 (14) | 9 (35) | |
| Medications: n (%) | | | |
| Antibiotics | 23 (35) | 4 (14) | |
| 5-ASA | 49 (74) | 26 (90) | |
| Corticosteroids | 16 (24) | 9 (35) | |
| AZA/6-MP | 26 (39) | 17 (59) | |
| Methotrexate | 0 | 1 (3) | |
| Infliximab | 15 (23) | 2 (7) | |
| Crohn's Disease Subtype: n (total) | | | |
| Nonstricturing and nonpenetrating | 18 (27) | | |
| Penetrating | 26 (40) | | |
| Stricturing | 14 (21) | | |
| Penetrating and stricturing | 8 (12) | | |
| Ulcerative Colitis: n (total) | | | |
| Left Sided Colitis | | 13 (45) | |
| Pancolitis | | 18 (62) | |

Figure 2A:
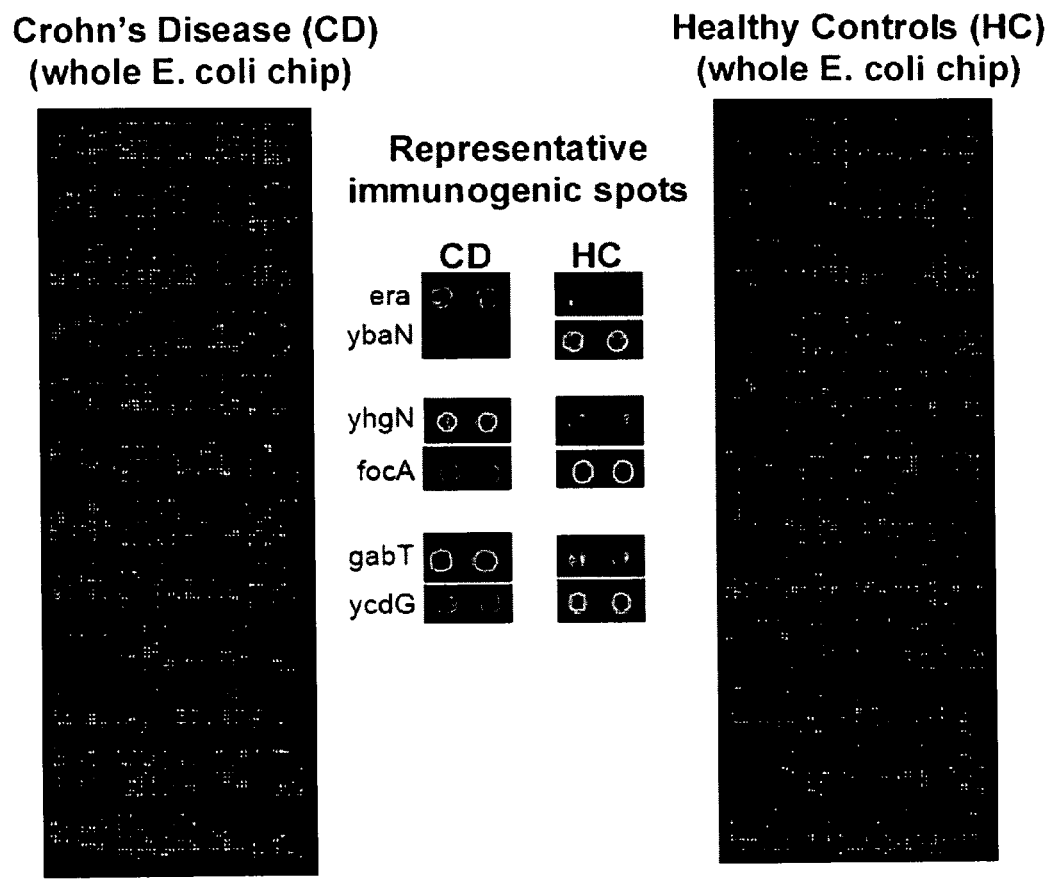
FIGS. 2A and 2B show representative images of *E. coli* proteome chips and a scatter plot, respectively. The proteome chip in FIG. 2A was probed with sera from Crohn's Disease patients and healthy controls, respectively. Two *E. coli* proteome chips probed with sera from a Crohn's Disease (CD) patient (left panel) and a healthy control (HC) (right panel). To identify the proteins that can be recognized by reactive serum antibodies, each *E. coli* protein chip was incubated with a serum from healthy control or Crohn's Disease, as illustrated in FIG. 1. Cy3-labeled anti-human immunoglobulin antibodies were then probed on the chips, allowing visualization of immunoreactive protein spots. The immunogenic profiles of both the IBD patients and healthy control were acquired by the resulting fluorescent signals. Green spots are spots of *E. coli* protein in the chips detected by serum antibodies, representing immunogenic reactions. The intensity of the protein spots reflects immunogenicity of the proteins. Middle panel shows some representative images of immunogenic spots of three pairs of specific proteins (see more information of these proteins in FIG. 5 and Tables 1-3) from these proteome chips. Every *E. coli* protein is spotted in duplicate on the chip. Crohn's Disease vs ulcerative colitis vs healthy control can be distinguished by comparing the signal intensities between protein spots on the *E. coli* proteome chips.
Figure 2B:
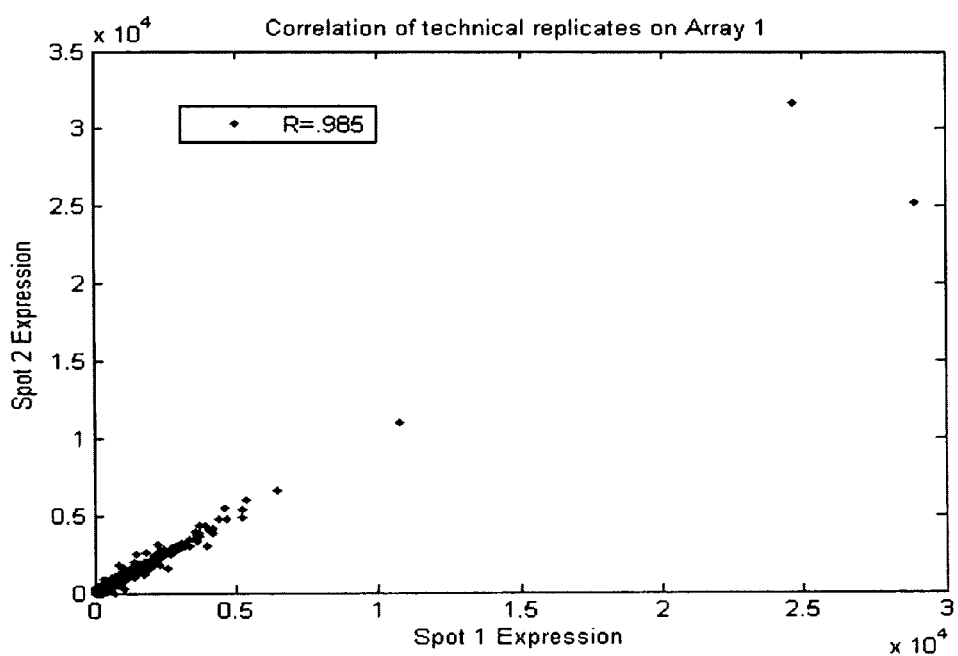

To identify potential biomarkers for IBD diagnosis, the antibody repertoire of the IBD patients was profiled using the *E. coli* proteome chips that each contained more than 4,200 individual proteins (see schematic illustration of our strategy in (FIG. 1). Since each protein was spotted in duplicate on the chip, the reproducibility of duplicates of each protein was first analyzed. As shown in FIG. 2A, the visual appearance of duplicate spots was very similar. As shown in FIG. 2B in scatter plot, the duplicate spots of each protein were highly correlated, indicating the good quality of the array manufacturing. To recognize those reactive antibodies on the chips, the chips were probed with Cy3-labeled anti-human immunoglobulin antibodies. The immunogenic profiles of both the IBD patients and healthy control were acquired by the resulting fluorescent signals. CD vs ulcerative colitis vs healthy control can be distinguished by comparing the signal intensities between protein spots on the *E. coli* proteome chips (see FIG. 2A, which shows visual appearance of two representative chips probed with sera from CD and healthy control, respectively). Two-level of data analyses were performed with these immunogenic profiles (i) to identify differential immunogenic responses among CD vs ulcerative colitis vs healthy control using Significance Analysis of Microarray (SAM) and Gene Ontology (GO) enrichment analysis; and (ii) to construct robust classifiers to distinguish CD vs ulcerative colitis vs healthy control using k-TSP method.

Example 2

Global Immunogenic Profiles of IBD Against *E. coli*

Figure 3:
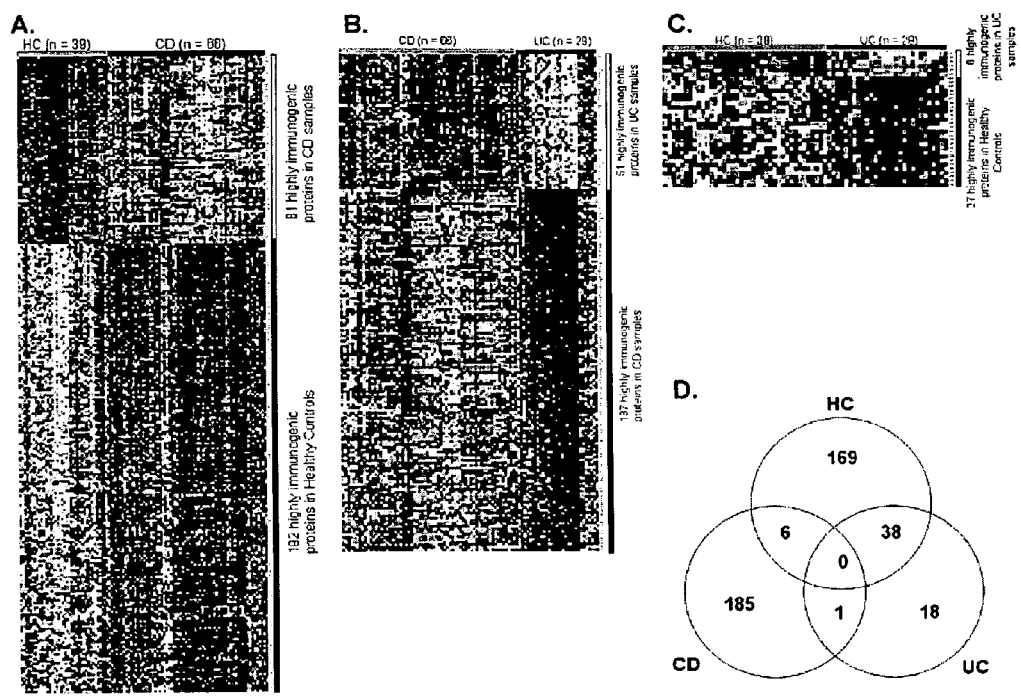
FIG. 3 shows global immunogenic profiles of IBD patients' sera against *E. coli* proteins.

Sera samples from healthy control subjects (n=39), patients with Crohn's Disease (n=66), and patients with ulcerative colitis (n=29) (Table 1) were used to compare differences between healthy control and IBD immunogenic profiles. To investigate the differential global changes in immunogenic response to *E. coli* proteins among healthy control vs Crohn's Disease vs ulcerative colitis, SAM was employed as described herein above for the immunogenic profiles. For convenience, the *E. coli* proteins that were differentially recognized by serum antibodies from healthy control, Crohn's Disease or ulcerative colitis are referred to as "differentially-expressed immunogenic proteins" throughout. Heat maps shown in FIGS. 3A-C present a visual illustration of the differentially immunogenic proteins for each phenotype. 273 differentially immunogenic proteins were identified by SAM when compared healthy control with CD samples. 81 proteins are highly immunogenic in CD samples and 192 are highly immunogenic in healthy control samples (FIG. 3A). Conversely, 188 proteins have different immunogenic responses in the IBD subtypes, 51 and 137 are highly immunogenic in ulcerative colitis and CD samples, respectively (FIG. 3B). When healthy control and ulcerative colitis samples are compared, only 27 and 6 proteins are discriminatory and highly immunogenic in healthy control and ulcerative colitis samples, respectively (FIG. 3C). A full list of the immunogenic *E. coli* proteins in FIGS. 3A-C can be found in Tables 2-4, respectively.

TABLE 2

| SAM ANALYSIS OF HEALTHY CONTROLS (HC) VERSUS CROHN'S DISEASE (CD) (see FIG. 3A) | | | |
|---|---|---|---|
| SPOT | PROTEIN | NAME | GO BP |
| 81 Highly immunogenic proteins in CD | | | |
| yfiC | yfiC | Hypothetical protein yfiC /// predicted S-adenosyl-L-methionine-dependent methyltransferase | — |
| era | era | GTP-binding protein Era | 50875 // cellular physiological process // inferred from electronic annotation |
| ygbD | ygbD | nitric oxide reductase | 6118 // electron transport // inferred from electronic annotation |
| yjhO | yjhO /// sgcX | KpLE2 phage-like element; predicted endoglucanase with | — |

TABLE 2-continued

SAM ANALYSIS OF HEALTHY CONTROLS (HC) VERSUS CROHN'S DISEASE (CD) (see FIG. 3A)

| | | | |
|---|---|---|---|
| aidA | aidA | Zn-dependent exopeptidase domain DNA-3-methyladenine glycosylase II /// 3-methyl-adenine DNA glycosylase II | 6281 // DNA repair // inferred from electronic annotation /// 6284 // base-excision repair // inferred from electronic annotation /// 6974 // response to DNA damage stimulus // inferred from electronic annotation /// 5975 // carbohydrate metabolism // inf |
| yhcI | yhcI /// nanK | N-acetylmannosamine kinase | 5975 // carbohydrate metabolism // inferred from electronic annotation /// 6051 // N-acetylmannosamine metabolism // inferred from electronic annotation |
| fliS | fliS | flagellar protein FliS | 9296 // flagellum biogenesis // inferred from electronic annotation |
| infC | infC | Translation initiation factor IF-3 | 6412 // protein biosynthesis // inferred from electronic annotation /// 6413 // translational initiation // inferred from electronic annotation /// 6417 // regulation of protein biosynthesis // inferred from electronic annotation /// 6445 // regulation of |
| metB | metB | cystathionine gamma-synthase | 6520 // amino acid metabolism // inferred from electronic annotation /// 8652 // amino acid biosynthesis // inferred from electronic annotation /// 9086 // methionine biosynthesis // inferred from electronic annotation |
| purM | purM | phosphoribosylaminoimidazole synthetase | 6164 // purine nucleotide biosynthesis // inferred from electronic annotation /// 6189 // 'de novo' IMP biosynthesis // inferred from electronic annotation |
| argC | argC | N-acetyl-gamma-glutamyl-phosphate reductase | 6520 // amino acid metabolism // |

TABLE 2-continued

SAM ANALYSIS OF HEALTHY CONTROLS (HC) VERSUS CROHN'S DISEASE (CD) (see FIG. 3A)

| | | | |
|---|---|---|---|
| | | | inferred from electronic annotation /// 6526 // arginine biosynthesis // inferred from electronic annotation /// 8652 // amino acid biosynthesis // inferred from electronic annotation /// 9085 // lysine biosynthesis // inf |
| phnB | phnB | PhnB protein /// hypothetical protein | — |
| torA | torA | Trimethylamine-N-oxide reductase 1 precursor /// trimethylamine N-oxide (TMAO) reductase I, catalytic subunit | 6118 // electron transport // inferred from electronic annotation |
| ibpB | ibpB | 16 kDa heat shock protein B /// heat shock chaperone | 6457 // protein folding // inferred from electronic annotation /// 6986 // response to unfolded protein // inferred from electronic annotation /// 50821 // protein stabilization // inferred from electronic annotation |
| hycF | hycF | hydrogenase 4 Fe—S subunit /// formate hydrogenlyase complex iron-sulfur protein | 6118 // electron transport // inferred from electronic annotation /// 6810 // transport // inferred from electronic annotation |
| ycbF | ycbF | predicted periplasmic pilini chaperone | 6457 // protein folding // inferred from electronic annotation /// 7047 // cell wall organization and biogenesis // inferred from electronic annotation |
| ssi6 | ssi6 | hypothetical protein | — |
| yjhE | yjhE | KpLE2 phage-like element; predicted membrane protein (pseudogene) | 6810 // transport // inferred from electronic annotation |
| ygeW | ygeW | ornithine carbamoyltransferase | 6207 // 'de novo' pyrimidine base biosynthesis // inferred from electronic annotation /// 6520 // amino acid metabolism // inferred from electronic annotation |
| hofH | hofH /// gspH | Putative general secretion pathway protein H precursor /// predicted general secretory pathway component, cryptic | 6810 // transport // inferred from electronic annotation /// 15628 // type II protein secretion system // inferred from |

TABLE 2-continued

SAM ANALYSIS OF HEALTHY CONTROLS (HC) VERSUS CROHN'S DISEASE (CD) (see FIG. 3A)

| | | | |
|---|---|---|---|
| rffD | rffD /// wecC | UDP-N-acetyl-D-mannosamine dehydrogenase /// UDP-N-acetyl-D-mannosaminuronic acid dehydrogenase | electronic annotation 6118 // electron transport // inferred from electronic annotation |
| yjhC | yjhC | KpLE2 phage-like element; predicted oxidoreductase | 6118 // electron transport // inferred from electronic annotation /// 8152 // metabolism // inferred from electronic annotation |
| yjcS | yjcS | Hypothetical protein yjcS | — |
| ftn | ftn | Ferritin 1 /// ferritin iron storage protein (cytoplasmic) | 6826 // iron ion transport // inferred from electronic annotation /// 6879 // iron ion homeostasis // inferred from electronic annotation |
| ybbQ | ybbQ | 2-hydroxy-3-oxopropionate reductase | 6098 // pentose-phosphate shunt // inferred from electronic annotation /// 6573 // valine metabolism // inferred from electronic annotation /// 46487 // glyoxylate metabolism // inferred from electronic annotation |
| ppdB | ppdB | Prepilin peptidase dependent protein B precursor /// hypothetical protein | — |
| fimC | fimC | Chaperone protein fimC precursor /// chaperone, periplasmic | 6457 // protein folding // inferred from electronic annotation /// 7047 // cell wall organization and biogenesis // inferred from electronic annotation |
| dgxA | dgxA | hypothetical protein | — |
| fumB | fumB | Fumarate hydratase class I, anaerobic /// anaerobic class I fumarate hydratase (fumarase B) | 6091 // generation of precursor metabolites and energy // inferred from electronic annotation /// 6099 // tricarboxylic acid cycle // inferred from electronic annotation |
| (thiS) | thiS | sulfur carrier protein ThiS | 6790 // sulfur metabolism // inferred from electronic annotation |
| yjeJ | yjeJ | Hypothetical protein yjeJ /// hypothetical protein | — |
| cedA | cedA | Cell division activator cedA /// cell division modulator | 7049 // cell cycle // inferred from electronic annotation /// 51301 // cell division // |

TABLE 2-continued

SAM ANALYSIS OF HEALTHY CONTROLS (HC) VERSUS CROHN'S DISEASE (CD) (see FIG. 3A)

| | | | |
|---|---|---|---|
| | | | inferred from electronic annotation |
| cysW | cysW | sulfate/thiosulfate transporter subunit | 6810 // transport // inferred from electronic annotation /// 8272 // sulfate transport // inferred from electronic annotation |
| ygcQ | ygcQ | Putative electron transfer flavoprotein subunit ygcQ | 6118 // electron transport // inferred from electronic annotation |
| rpsR | rpsR | 30S ribosomal protein S18 | 6412 // protein biosynthesis // inferred from electronic annotation |
| narY | narY | nitrate reductase 2 (NRZ), beta subunit | 6118 // electron transport // inferred from electronic annotation /// 6810 // transport // inferred from electronic annotation /// 42126 // nitrate metabolism // inferred from electronic annotation /// 42128 // nitrate assimilation // inferred from electr |
| citB | citB | Transcriptional Regulatory protein dpiA /// DNA-binding response regulator in two-component regulatory system with citA | 160 // two-component signal transduction system (phosphorelay) // inferred from electronic annotation /// 6350 // transcription // inferred from electronic annotation /// 6355 // regulation of transcription, DNA-dependent // inferred from electronic annotation |
| yjbR | yjbR | Protein yjbR /// hypothetical protein | — |
| ybbA | ybbA | Hypothetical ABC transporter ATP-binding protein ybbA /// predicted transporter subunit: ATP-binding component of ABC superfamily | 6810 // transport // inferred from electronic annotation |
| gst | gst | Glutathione S-transferase /// glutathionine S-transferase | — |
| grxC | grxC | Glutaredoxin 3 | 6118 // electron transport // inferred from electronic annotation /// 6810 // transport // inferred from electronic annotation /// 9263 // deoxyribonucleotide biosynthesis // inferred from electronic |

TABLE 2-continued

SAM ANALYSIS OF HEALTHY CONTROLS (HC) VERSUS CROHN'S DISEASE (CD) (see FIG. 3A)

| | | | |
|---|---|---|---|
| cysD | cysD | sulfate adenylyltransferase subunit 2 | annotation /// 45454 // cell redox homeostasis // infer 103 // sulfate assimilation // inferred from electronic annotation /// 8152 // metabolism // inferred from electronic annotation /// 8652 // amino acid biosynthesis // inferred from electronic annotation /// 19344 // cysteine biosynthesis // inferred from electronic annotation |
| radC | radC | DNA repair protein RadC | 6281 // DNA repair // inferred from electronic annotation /// 6974 // response to DNA damage stimulus // inferred from electronic annotation |
| citG | citG | 2-(5''-triphosphoribosyl)-3'-dephosphocoenzyme-A synthase /// triphosphoribosyl-dephospho-CoA transferase | — |
| fdhE | fdhE | formate dehydrogenase accessory protein FdhE | 6118 // electron transport // inferred from electronic annotation |
| fecB | fecB | KpLE2 phage-like element; iron-dicitrate transporter subunit | 6810 // transport // inferred from electronic annotation /// 6811 // ion transport // inferred from electronic annotation /// 6826 // iron ion transport // inferred from electronic annotation /// 6827 // high affinity iron ion transport inferred from electronic annotation |
| yhgH | yhgH /// gntX | Hypothetical protein yhgH /// gluconate periplasmic binding protein with phosphoribosyltransferase domain, GNT I system | 9116 // nucleoside metabolism // inferred from electronic annotation |
| (phnE) | phnE | membrane channel protein component of Pn transporter | 6810 // transport // inferred from electronic annotation /// 15716 // phosphonate transport // inferred from electronic annotation |
| cysJ | cysJ | Sulfite reductase [NADPH] flavoprotein alpha-component /// sulfite reductase, alpha subunit, flavoprotein | 103 // sulfate assimilation // inferred from electronic annotation /// 6118 // electron transport // inferred from electronic |

TABLE 2-continued

SAM ANALYSIS OF HEALTHY CONTROLS (HC) VERSUS CROHN'S DISEASE (CD) (see FIG. 3A)

| | | | |
|---|---|---|---|
| | | | annotation /// 6810 // transport // inferred from electronic annotation /// 8652 // amino acid biosynthesis // inferred from electronic annotation |
| 445#15 | ygaX | Putative transport protein /// predicted transporter | 6810 // transport |
| fba | fba /// fbaA | fructose-bisphosphate aldolase /// fructose-bisphosphate aldolase | 6096 // glycolysis // inferred from electronic annotation |
| yjbI | yjbI | hypothetical protein | — |
| yfjQ | yfjQ | CP4-57 prophage; predicted protein | — |
| mltB | mltB | Membrane-bound lytic murein transglycosylase B precursor | 5975 // carbohydrate metabolism // inferred from electronic annotation |
| yhaA | yhaA /// tdcD | propionate kinase/acetate kinase C, anaerobic | 6082 // organic acid metabolism // inferred from electronic annotation /// 8152 // metabolism // inferred from electronic annotation /// 16310 // phosphorylation // inferred from electronic annotation |
| yjeB | yjeB | Hypothetical protein yjeB /// predicted DNA-binding transcriptional regulator | 6412 // protein biosynthesis // inferred from electronic annotation |
| thiF | thiF | thiamine biosynthesis protein ThiF | 9228 // thiamin biosynthesis // inferred from electronic annotation |
| gcpE | gcpE /// ispG | 4-hydroxy-3-methylbut-2-en-1-yl diphosphate synthase /// 4-hydroxy-3-methylbut-2-en-1-yl diphosphate synthase | 8299 // isoprenoid biosynthesis // inferred from electronic annotation /// 16114 // terpenoid biosynthesis // inferred from electronic annotation |
| mviN | mviN | Virulence factor mviN homolog /// predicted inner membrane protein | 9405 // pathogenesis // inferred from electronic annotation |
| yihK | yihK /// bipA | GTP-binding protein typA/BipA /// GTP-binding protein | 6412 // protein biosynthesis // inferred from electronic annotation |
| ubiG | ubiG | 3-demethylubiquinone-9 3-methyltransferase | 6744 // ubiquinone biosynthesis // inferred from electronic annotation |

TABLE 2-continued

SAM ANALYSIS OF HEALTHY CONTROLS (HC) VERSUS CROHN'S DISEASE (CD) (see FIG. 3A)

| | | | |
|---|---|---|---|
| yejG | yejG | Hypothetical protein yejG /// hypothetical protein | — |
| 304#1 | lsrB | AI2 transporter | — |
| ygfY | ygfY | Hypothetical protein ygfY /// hypothetical protein | — |
| 319#17 | ydhZ | Hypothetical protein ydhZ /// hypothetical protein | — |
| 336#6 | | | |
| 430#8 | iscR | Hypothetical protein yfhP /// DNA-binding transcriptional repressor | — |
| yhfR | yhfR /// frlR | predicted DNA-binding transcriptional regulator | 6350 // transcription // inferred from electronic annotation /// 6355 // regulation of transcription, DNA-dependent // inferred from electronic annotation /// 45449 // regulation of transcription // inferred from electronic annotation |
| phnG | phnG | PhnG protein /// carbon-phosphorus lyase complex subunit | 15716 // phosphonate transport // inferred from electronic annotation /// 19634 // phosphonate metabolism // inferred from electronic annotation |
| ymfE | ymfE | e14 prophage; predicted inner membrane protein | — |
| yejO | yejO | predicted autotransporter outer membrane protein | 7155 // cell adhesion // inferred from electronic annotation |
| dicC | dicC | Qin prophage; DNA-binding transcriptional regulator for DicB | 6350 // transcription // inferred from electronic annotation /// 6355 // regulation of transcription, DNA-dependent // inferred from electronic annotation /// 7049 // cell cycle // inferred from electronic annotation /// 51301 // cell division // inferred from electronic annotation |
| galR | galR | Galactose operon repressor /// DNA-binding transcriptional repressor | 5975 // carbohydrate metabolism // inferred from electronic annotation /// 6012 // galactose metabolism // inferred from electronic annotation /// 6350 // transcription // inferred from electronic annotation /// 6355 |

TABLE 2-continued

SAM ANALYSIS OF HEALTHY CONTROLS (HC) VERSUS CROHN'S DISEASE (CD) (see FIG. 3A)

| | | | |
|---|---|---|---|
| | | | // regulation of transcription, DNA-de |
| yphC | yphC | Hypothetical zinc-type alcohol dehydrogenase-like protein yphC | — |
| rplT | rplT | 50S ribosomal protein L20 | 27 // ribosomal large subunit assembly and maintenance // inferred from electronic annotation /// 6412 // protein biosynthesis // inferred from electronic annotation |
| 267#6 | paaJ | acetyl-CoA acetyltransferase | — |
| selD | selD | selenophosphate synthetase | — |
| tdcB | tdcB | threonine dehydratase | 6520 // amino acid metabolism // inferred from electronic annotation /// 8152 // metabolism // inferred from electronic annotation |
| yhfV | yhfV | Phosphotriesterase homology protein | 9056 // catabolism // inferred from electronic annotation |
| yjaI | yjaI /// zraP | Zinc resistance-associated protein precursor /// Zn-binding periplasmic protein | — |
| hycA | hycA | Formate hydrogenlyase Regulatory protein hycA /// regulator of the transcriptional regulator FhlA | 6350 // transcription // inferred from electronic annotation /// 6355 // regulation of transcription, DNA-dependent // inferred from electronic annotation |
| 192 Highly immunogenic response proteins in HC ||||
| pbuX | pbuX | hypothetical protein | — |
| fabH | fabH | 3-oxoacyl-(acyl carrier protein) synthase | 6633 // fatty acid biosynthesis // inferred from electronic annotation /// 8610 // lipid biosynthesis // inferred from electronic annotation |
| glpF | glpF | Glycerol uptake facilitator protein /// glycerol facilitator | 6810 // transport // inferred from electronic annotation |
| 273#6 | ydcU | Hypothetical ABC transporter permease protein ydcU /// predicted spermidine/putrescine transporter subunit | 6810 // transport |
| ybhR | ybhR | Hypothetical protein ybhR /// predicted transporter subunit: membrane component of ABC superfamily | 6810 // transport // inferred from electronic annotation |
| yqcE | yqcE | Hypothetical protein yqcE /// predicted transporter | 6810 // transport // inferred from electronic annotation |
| flhD | flhD | transcriptional activator FlhD | 6350 // transcription // inferred from electronic annotation /// 6355 // regulation of transcription, DNA-dependent // inferred from electronic annotation /// 9296 // flagellum biogenesis // inferred from electronic annotation /// 45893 // positive regula |
| trkG | trkG | Rac prophage; potassium transporter subunit | 6810 // transport // inferred from electronic annotation |

TABLE 2-continued

SAM ANALYSIS OF HEALTHY CONTROLS (HC) VERSUS CROHN'S DISEASE (CD) (see FIG. 3A)

| | | | |
|---|---|---|---|
| | | | /// 6811 // ion transport // inferred from electronic annotation /// 6812 // cation transport // inferred from electronic annotation /// 6813 // potassium ion transport // inferred from electronic annotation |
| ybdS | ybdS | Citrate carrier/transporter | 6814 // sodium ion transport // inferred from electronic annotation |
| brnQ | brnQ | Branched-chain amino acid transport system II carrier protein /// predicted branched chain amino acid transporter (LIV-II) | 6810 // transport // inferred from electronic annotation /// 6865 // amino acid transport // inferred from electronic annotation /// 15803 // branched-chain aliphatic amino acid transport // inferred from electronic annotation |
| ycaD | ycaD | putative MFS family transporter protein | 6810 // transport // inferred from electronic annotation |
| ybhN | ybhN | Hypothetical protein ybhN /// conserved inner membrane protein | — |
| yabK | yabK /// thiP | thiamin ABC transporter membrane component | 6810 // transport // inferred from electronic annotation |
| ycdG | ycdG | Putative purine permease ycdG /// predicted transporter | 6810 // transport // inferred from electronic annotation |
| yojI | yojI | Hypothetical ABC transporter ATP-binding protein yojI /// fused predicted multidrug transport subunits of ABC superfamily: membrane component/ATP-binding component | 6810 // transport // inferred from electronic annotation /// 15833 // peptide transport // inferred from electronic annotation /// 46677 // response to antibiotic // inferred from electronic annotation |
| ybaN | ybaN | Hypothetical protein ybaN /// conserved inner membrane protein | — |
| focA | focA | F1C major fimbrial subunit precursor | 7155 // cell adhesion // inferred from electronic annotation |
| 321#3 yciR | yciR | Hypothetical protein yciR | 7165 // signal transduction // inferred from electronic annotation |
| 427#1 | yfgF | Hypothetical protein yfgF /// predicted inner membrane protein | — |
| celD | celD /// chbR | Cel operon repressor /// DNA-binding transcriptional dual regulator | 6350 // transcription // inferred from electronic annotation /// 6355 // regulation of transcription, DNA-dependent // inferred from electronic annotation /// 45449 // regulation of transcription // inferred from electronic annotation |
| uidB | uidB | Glucuronide carrier protein /// glucuronide transporter | 6810 // transport // inferred from electronic annotation /// 6814 // sodium ion transport // inferred from electronic annotation |
| ydjS | ydjS /// astE | succinylglutamate desuccinylase /// succinylglutamate desuccinylase | 6525 // arginine metabolism // inferred from electronic annotation /// 6527 // arginine catabolism // inferred from electronic annotation /// 8152 // metabolism // inferred from electronic annotation |
| rocE | rocE | hypothetical protein | — |
| emrY | emrY | Multidrug resistance protein Y /// predicted multidrug efflux system | 6810 // transport // inferred from electronic annotation /// 6306 // DNA methylation // inferred from electronic annotation |
| cydC | cydC | Transport ATP-binding protein cydC /// fused cysteine transporter subunits of ABC | 6810 // transport // inferred from electronic annotation |

TABLE 2-continued

SAM ANALYSIS OF HEALTHY CONTROLS (HC) VERSUS CROHN'S DISEASE (CD) (see FIG. 3A)

| | | | |
|---|---|---|---|
| | | superfamily: membrane component/ATP-binding component | |
| yhhS | yhhS | hypothetical protein /// predicted transporter | 6810 // transport // inferred from electronic annotation |
| 406#7 | yfcH | Hypothetical protein yfcH /// conserved protein with NAD(P)-binding Rossmann-fold domain | 9225 // nucleotide-sugar metabolism |
| atoE | atoE | Short-chain fatty acids transporter /// short chain fatty acid transporter | 6810 // transport // inferred from electronic annotation /// 15912 // short-chain fatty acid transport // inferred from electronic annotation |
| ybgE | ybgE | Protein ybgE /// conserved inner membrane protein | — |
| JW0438 | mdlA | Multidrug resistance-like ATP-binding protein mdlA | 6810 // transport |
| (yhhT) | yhhT | Hypothetical protein yhhT /// predicted inner membrane protein | — |
| ybhM | ybhM | Hypothetical protein ybhM | — |
| yicO | yicO | Hypothetical protein yicO /// predicted xanthine/uracil permase | 6810 // transport // inferred from electronic annotation |
| ybhL | ybhL | Hypothetical protein ybhL /// predicted inner membrane protein | — |
| yhiQ | yhiQ | Hypothetical protein yhiQ | — |
| ydaA | ydaA /// uspE | Protein ydaA /// stress-induced protein | 6950 // response to stress // inferred from electronic annotation |
| ydjZ | ydjZ | Hypothetical protein ydjZ /// conserved inner membrane protein | — |
| dnaQ | dnaQ | DNA polymerase III subunit epsilon | 6260 // DNA replication // inferred from electronic annotation |
| yidY | yidY /// mdtL | Hypothetical transport protein yidY /// multidrug efflux system protein | 6810 // transport // inferred from electronic annotation /// 46677 // response to antibiotic // inferred from electronic annotation |
| 211#11 dgkA | dgkA | Diacylglycerol kinase | 8654 // phospholipid biosynthesis // inferred from electronic annotation |
| secF | secF | protein export protein SecF | 6605 // protein targeting // inferred from electronic annotation /// 6810 // transport // inferred from electronic annotation /// 6886 // intracellular protein transport // inferred from electronic annotation /// 15031 // protein transport // inferred from electronic annotation |
| ybbC | ybbC | hypothetical protein | — |
| fadA | fadA | acetyl-CoA acetyltransferase | 6629 // lipid metabolism // inferred from electronic annotation /// 6631 // fatty acid metabolism // inferred from electronic annotation /// 16042 // lipid catabolism // inferred from electronic annotation |
| fepD | fepD | Ferric enterobactin transport system permease protein fepD | 6810 // transport // inferred from electronic annotation |
| sdhD | sdhD | succinate dehydrogenase cytochrome b556 small membrane subunit | 6099 // tricarboxylic acid cycle // inferred from electronic annotation /// 6118 // electron transport // inferred from electronic annotation /// 6810 // transport // inferred from electronic annotation |
| yeiO | yeiO /// setB | Sugar efflux transporter B /// lactose/glucose efflux system | 6810 // transport // inferred from electronic annotation /// 8643 // carbohydrate transport // inferred from electronic annotation |
| yhfU | yhfU | Hypothetical protein yhfU /// hypothetical protein | — |

TABLE 2-continued

SAM ANALYSIS OF HEALTHY CONTROLS (HC) VERSUS CROHN'S DISEASE (CD) (see FIG. 3A)

| | | | |
|---|---|---|---|
| (yeeF) | yeeF | Hypothetical transport protein yeeF /// predicted amino-acid transporter | 6810 // transport // inferred from electronic annotation /// 6865 // amino acid transport // inferred from electronic annotation |
| yaeG | yaeG /// cdaR | Carbohydrate diacid regulator /// DNA-binding transcriptional activator | 6350 // transcription // inferred from electronic annotation /// 6355 // regulation of transcription, DNA-dependent // inferred from electronic annotation |
| nac | nac | Nitrogen assimilation Regulatory protein nac /// DNA-binding transcriptional dual regulator of nitrogen assimilation | 6350 // transcription // inferred from electronic annotation /// 6355 // regulation of transcription, DNA-dependent // inferred from electronic annotation /// 42128 // nitrate assimilation // inferred from electronic annotation |
| msbA | msbA | Probable transport ATP-binding protein msbA /// fused lipid transporter subunits of ABC superfamily: membrane component/ATP-binding component | 6810 // transport // inferred from electronic annotation /// 6869 // lipid transport // inferred from electronic annotation |
| narI | narI | Respiratory nitrate reductase 1 gamma chain /// nitrate reductase 1, gamma (cytochrome b(NR)) subunit | 6118 // electron transport // inferred from electronic annotation /// 6810 // transport // inferred from electronic annotation /// 42128 // nitrate assimilation // inferred from electronic annotation |
| oppC | oppC | Oligopeptide transport system permease protein oppC /// oligopeptide transporter subunit | 6810 // transport // inferred from electronic annotation /// 6857 // oligopeptide transport // inferred from electronic annotation /// 15031 // protein transport // inferred from electronic annotation |
| yibQ | yibQ | Hypothetical protein yibQ precursor /// predicted polysaccharide deacetylase | — |
| pheP | pheP | Phenylalanine-specific permease /// phenylalanine transporter | 6810 // transport // inferred from electronic annotation /// 6865 // amino acid transport // inferred from electronic annotation |
| 16-3B0 emrD | emrD | Multidrug resistance protein D /// multidrug efflux system protein | 6810 // transport // inferred from electronic annotation /// 15893 // drug transport // inferred from electronic annotation |
| ydeZ | ydeZ /// lsrD | AI2 transporter | 6810 // transport // inferred from electronic annotation |
| 280#1 | ddpX | D-ala-D-ala dipeptidase, Zn-dependent | 6508 // proteolysis |
| ybfC | ybfC | hypothetical protein | — |
| ydcD | ydcD | hypothetical protein | — |
| ygjR | ygjR | Hypothetical oxidoreductase ygjR /// predicted NAD(P)-binding dehydrogenase | 6118 // electron transport // inferred from electronic annotation /// 8152 // metabolism // inferred from electronic annotation |
| yehY | yehY | Hypothetical ABC transporter permease protein yehY /// predicted transporter subunit: membrane component of ABC superfamily | 6810 // transport // inferred from electronic annotation |
| ppx | ppx | Exopolyphosphatase | — |
| nagE | nagE | PTS system, N-acetylglucosamine-specific IIABC component | 6810 // transport // inferred from electronic annotation /// 9401 // phosphoenolpyruvate-dependent sugar phosphotransferase system // inferred from electronic annotation |

TABLE 2-continued

SAM ANALYSIS OF HEALTHY CONTROLS (HC) VERSUS
CROHN'S DISEASE (CD) (see FIG. 3A)

| | | | |
|---|---|---|---|
| kch | kch | Putative potassium channel protein /// voltage-gated potassium channel | 6810 // transport // inferred from electronic annotation /// 6811 // ion transport // inferred from electronic annotation /// 6813 // potassium ion transport // inferred from electronic annotation |
| yjeM | yjeM | Hypothetical transporter yjeM /// predicted transporter | 6810 // transport // inferred from electronic annotation /// 6865 // amino acid transport // inferred from electronic annotation |
| ybfB | ybfB | predicted inner membrane protein | — |
| 279#6 | ddpC | D-ala-D-ala transporter subunit | 6810 // transport |
| aqpZ | aqpZ | aquaporin Z | 6810 // transport // inferred from electronic annotation |
| yhjX | yhjX | Hypothetical protein yhjX | 6810 // transport // inferred from electronic annotation |
| malX | malX | PTS system, maltose and glucose-specific IIABC component /// fused maltose and glucose-specific PTS enzymes: IIB component-! IIC component | 6810 // transport // inferred from electronic annotation /// 9401 // phosphoenolpyruvate-dependent sugar phosphotransferase system // inferred from electronic annotation |
| ycbM | ycbM /// ssuC | Putative aliphatic sulfonates transport permease protein ssuC /// alkanesulfonate transporter subunit | 6810 // transport // inferred from electronic annotation |
| narU | narU | Nitrite extrusion protein 2 /// nitrate/nitrite transporter | 6810 // transport // inferred from electronic annotation /// 15698 // inorganic anion transport // inferred from electronic annotation /// 42128 // nitrate assimilation // inferred from electronic annotation |
| lpxC | lpxC | UDP-3-O-[3-hydroxymyristoyl] N-acetylglucosamine deacetylase | 8610 // lipid biosynthesis // inferred from electronic annotation /// 9245 // lipid A biosynthesis // inferred from electronic annotation |
| secY/prlA | secY /// prlA | preprotein translocase SecY /// protein translocase subunit SecY | 6605 // protein targeting // inferred from electronic annotation /// 6810 // transport // inferred from electronic annotation /// 9306 // protein secretion // inferred from electronic annotation /// 15031 // protein transport // inferred from electronic annotation |
| (yhcP) | yhcP | Hypothetical protein yhcP /// p-hydroxybenzoic acid efflux system component | 6810 // transport // inferred from electronic annotation |
| phsE | phsE /// dacD | Penicillin-binding protein 6B precursor /// D-alanyl-D-alanine carboxypeptidase (penicillin-binding protein 6b) | 6508 // proteolysis // inferred from electronic annotation /// 8360 // regulation of cell shape // inferred from electronic annotation /// 9252 // peptidoglycan biosynthesis // inferred from electronic annotation |
| hemY | hemY | predicted protoheme IX synthesis protein | 6779 // porphyrin biosynthesis // inferred from electronic annotation |
| yciS | yciS | Hypothetical protein yciS /// conserved inner membrane protein | — |
| malZ | malZ | Maltodextrin glucosidase | 5975 // carbohydrate metabolism // inferred from electronic annotation |
| ymdD | ymdD /// mdoC | glucans biosynthesis protein | 9250 // glucan biosynthesis // inferred from electronic annotation |

TABLE 2-continued

SAM ANALYSIS OF HEALTHY CONTROLS (HC) VERSUS CROHN'S DISEASE (CD) (see FIG. 3A)

| | | | |
|---|---|---|---|
| 316#4 | rsxA | hypothetical protein | — |
| rfaB | rfaB | UDP-D-galactose:(glucosyl)lipopolysaccharide-1,6-D-galactosyltransferase | 9058 // biosynthesis // inferred from electronic annotation /// 9103 // lipopolysaccharide biosynthesis // inferred from electronic annotation |
| emrB | emrB | multidrug efflux system protein | 6810 // transport // inferred from electronic annotation /// 46677 // response to antibiotic // inferred from electronic annotation |
| 356#7 | yegJ | hypothetical protein | — |
| fsr | fsr | Fosmidomycin resistance protein /// predicted fosmidomycin efflux system | 6810 // transport // inferred from electronic annotation /// 46677 // response to antibiotic // inferred from electronic annotation |
| yigF | yigF | conserved inner membrane protein | — |
| 233#6 | yceJ | Cytochrome b561 homolog 2 /// predicted cytochrome b561 | 6118 // electron transport /// 6810 // transport |
| 331#2 | yeaE | Hypothetical protein yeaE | — |
| mrdB | mrdB | Rod shape-determining protein rodA | 7049 // cell cycle // inferred from electronic annotation /// 8360 // regulation of cell shape // inferred from electronic annotation |
| thiL | thiL | thiamine monophosphate kinase | 9228 // thiamin biosynthesis // inferred from electronic annotation |
| yphD | yphD | predicted sugar transporter subunit: membrane component of ABC superfamily | 6810 // transport // inferred from electronic annotation |
| fabZ | fabZ | (3R)-hydroxymyristoyl ACP dehydratase | 6633 // fatty acid biosynthesis // inferred from electronic annotation /// 8610 // lipid biosynthesis // inferred from electronic annotation /// 9245 // lipid A biosynthesis // inferred from electronic annotation |
| yoaA | yoaA | conserved protein with nucleoside triphosphate hydrolase domain | 6139 // nucleobase, nucleoside, nucleotide and nucleic acid metabolism // inferred from electronic annotation |
| yfjY | yfjY | CP4-57 prophage; predicted DNA repair protein | 6281 // DNA repair // inferred from electronic annotation |
| nrfE | nrfE | heme lyase (NrfEFG) for insertion of heme into c552, subunit NrfE | 6461 // protein complex assembly // inferred from electronic annotation /// 8535 // cytochrome c oxidase complex assembly // inferred from electronic annotation /// 15886 // heme transport // inferred from electronic annotation /// 17004 // cytochrome com |
| udk | udk | uridine kinase | 8655 // pyrimidine salvage // inferred from electronic annotation /// 9058 // biosynthesis // inferred from electronic annotation |
| yhhL | yhhL | Hypothetical protein yhhL /// conserved inner membrane protein | — |
| JW1949 | yedS_3 | Pseudo | — |
| sucB | sucB | dihydrolipoamide acetyltransferase | 6099 // tricarboxylic acid cycle // inferred from electronic annotation /// 8152 // metabolism // inferred from electronic annotation |
| aceF | aceF | dihydrolipoamide acetyltransferase | 6096 // glycolysis // inferred from electronic annotation /// 8152 // metabolism // inferred from electronic annotation |

TABLE 2-continued

SAM ANALYSIS OF HEALTHY CONTROLS (HC) VERSUS CROHN'S DISEASE (CD) (see FIG. 3A)

| | | | |
|---|---|---|---|
| yaiV | yaiV | Hypothetical protein yaiV /// predicted DNA-binding transcriptional regulator | 6355 // regulation of transcription, DNA-dependent // inferred from electronic annotation |
| yccY | yccY /// etp | phosphotyrosine-protein phosphatase | 6470 // protein amino acid dephosphorylation // inferred from electronic annotation |
| yhaO | yhaO | predicted transporter | 6810 // transport // inferred from electronic annotation |
| yhiP | yhiP | Hypothetical transporter yhiP /// predicted transporter | 6810 // transport // inferred from electronic annotation /// 6857 // oligopeptide transport // inferred from electronic annotation |
| yaaH | yaaH | Hypothetical protein yaaH /// conserved inner membrane protein associated with acetate transport | — |
| oppF | oppF | Oligopeptide transport ATP-binding protein oppF /// oligopeptide transporter subunit | 6810 // transport // inferred from electronic annotation /// 6857 // oligopeptide transport // inferred from electronic annotation /// 15031 // protein transport // inferred from electronic annotation /// 15833 // peptide transport // inferred from electronic annotation |
| pnuC | pnuC | Protein pnuC /// predicted nicotinamide mononucleotide transporter | 6810 // transport // inferred from electronic annotation |
| ansP | ansP | L-asparagine permease /// L-asparagine transporter | 6810 // transport // inferred from electronic annotation /// 6865 // amino acid transport // inferred from electronic annotation |
| cybB | cybB | Cytochrome b561 | 6118 // electron transport // inferred from electronic annotation /// 6810 // transport // inferred from electronic annotation |
| yddH | yddH | Hypothetical protein yddH | 6118 // electron transport // inferred from electronic annotation |
| sfsA | sfsA | sugar fermentation stimulation protein /// sugar fermentation stimulation protein A | — |
| slyX | slyX | hypothetical protein | — |
| dinI | dinI | DNA-damage-inducible protein I /// DNA damage-inducible protein I | 6281 // DNA repair // inferred from electronic annotation /// 6974 // response to DNA damage stimulus // inferred from electronic annotation /// 9432 // SOS response // inferred from electronic annotation |
| ynjC | ynjC | fused transporter subunits of ABC superfamily: membrane components | 6810 // transport // inferred from electronic annotation |
| 411#1 | yfdG | CPS-53 (KpLE1) prophage; bactoprenol-linked glucose translocase (flippase) | 271 // polysaccharide biosynthesis /// 6810 // transport |
| yjgT | yjgT /// idnT | Gnt-II system L-idonate transporter /// L-idonate and D-gluconate transporter | 6810 // transport // inferred from electronic annotation /// 15725 // gluconate transport // inferred from electronic annotation /// 19521 // D-gluconate metabolism // inferred from electronic annotation |
| yheG | yheG | Probable general secretion pathway protein E | 6810 // transport // inferred from electronic annotation /// 15628 // type II protein secretion system // inferred from electronic annotation |
| dgt | dgt | deoxyguanosinetriphosphate triphosphohydrolase | 46039 // GTP metabolism // inferred from electronic annotation |
| folK | folK | 2-amino-4-hydroxy-6-hydroxymethyldihydropteridine | 9396 // folic acid and derivative biosynthesis // |

TABLE 2-continued

SAM ANALYSIS OF HEALTHY CONTROLS (HC) VERSUS
CROHN'S DISEASE (CD) (see FIG. 3A)

| | | pyrophosphokinase | inferred from electronic annotation |
|---|---|---|---|
| gppA | gppA /// gpp | Guanosine-5'-triphosphate,3'-diphosphate pyrophosphatase /// guanosine pentaphosphatase/exopolyphosphatase | — |
| glnD | glnD | PII uridylyl-transferase | 6807 // nitrogen compound metabolism // inferred from electronic annotation /// 8152 // metabolism // inferred from electronic annotation /// 9399 // nitrogen fixation // inferred from electronic annotation |
| yhbX | yhbX | Outer-membrane protein yhbX precursor /// predicted hydrolase, inner membrane | 8152 // metabolism // inferred from electronic annotation |
| ygjQ | ygjQ | Hypothetical protein ygjQ | — |
| 323#1 | ydiV | Hypothetical protein ydiV /// hypothetical protein | — |
| cydB | cydB | Cytochrome D ubiquinol oxidase subunit II /// cytochrome d terminal oxidase, subunit II | 6118 // electron transport // inferred from electronic annotation /// 6810 // transport // inferred from electronic annotation |
| ybhA | ybhA | Hypothetical protein ybhA /// predicted hydrolase | 6812 // cation transport // inferred from electronic annotation /// 8152 // metabolism // inferred from electronic annotation |
| yibL | yibL | hypothetical protein | — |
| yifE | yifE | Protein yifE /// hypothetical protein | — |
| ygfF | ygfF | predicted NAD(P)-binding oxidoreductase with NAD(P)-binding Rossmann-fold domain | 8152 // metabolism // inferred from electronic annotation |
| rffG | rffG | dTDP-glucose 4,6-dehydratase | 9103 // lipopolysaccharide biosynthesis // inferred from electronic annotation /// 9225 // nucleotide-sugar metabolism // inferred from electronic annotation /// 44237 // cellular metabolism // inferred from electronic annotation |
| yeaS | yeaS | Hypothetical protein yeaS /// neutral amino-acid efflux system | 6865 // amino acid transport // inferred from electronic annotation |
| yaiM | yaiM /// frmB | Hypothetical protein yaiM /// predicted esterase | — |
| ygeD | ygeD | Hypothetical protein ygeD /// predicted inner membrane protein | — |
| yjhB | yjhB | KpLE2 phage-like element; predicted transporter | 6810 // transport // inferred from electronic annotation |
| codB | codB | Cytosine permease /// cytosine transporter | 6810 // transport // inferred from electronic annotation /// 15931 // nucleobase, nucleoside, nucleotide and nucleic acid transport // inferred from electronic annotation /// 19858 // cytosine metabolism // inferred from electronic annotation |
| rfaL | rfaL | O-antigen ligase | 9103 // lipopolysaccharide biosynthesis // inferred from electronic annotation |
| yiaQ | yiaQ /// sgbH | Probable hexulose-6-phosphate synthase /// 3-keto-L-gulonate 6-phosphate decarboxylase | 5975 // carbohydrate metabolism // inferred from electronic annotation /// 6207 // 'de novo' pyrimidine base biosynthesis // inferred from electronic annotation |
| potC | potC | spermidine/putrescine ABC transporter membrane component /// spermidine/putrescine ABC transporter membrane protein | 6810 // transport // inferred from electronic annotation |
| secB | secB | export protein SecB | 6457 // protein folding // inferred from electronic |

TABLE 2-continued

SAM ANALYSIS OF HEALTHY CONTROLS (HC) VERSUS CROHN'S DISEASE (CD) (see FIG. 3A)

| | | | |
|---|---|---|---|
| | | | annotation /// 6605 // protein targeting // inferred from electronic annotation /// 6810 // transport // inferred from electronic annotation /// 15031 // protein transport // inferred from electronic annotation |
| murG | murG | N-acetylglucosaminyl transferase | 5975 // carbohydrate metabolism // inferred from electronic annotation /// 7049 // cell cycle // inferred from electronic annotation /// 8360 // regulation of cell shape // inferred from electronic annotation /// 9252 // peptidoglycan biosynthesis // inferred from electronic annotation |
| ydhV | ydhV | Hypothetical protein ydhV /// predicted oxidoreductase | 6118 // electron transport // inferred from electronic annotation |
| putP | putP | Sodium/proline symporter /// proline:sodium symporter | 6810 // transport // inferred from electronic annotation /// 6811 // ion transport // inferred from electronic annotation /// 6814 // sodium ion transport // inferred from electronic annotation /// 6865 // amino acid transport // inferred from electronic annotation |
| yiaL | yiaL | Hypothetical protein yiaL | — |
| queA | queA | S-adenosylmethionine:tRNA ribosyltransferase-isomerase | 8616 // queuosine biosynthesis // inferred from electronic annotation |
| yhaH | yhaH | Hypothetical protein yhaH /// predicted inner membrane protein | — |
| cobU | cobU | adenosylcobinamide kinase /// adenosylcobinamide kinase/adenosylcobinamide-phosphate guanylyltransferase | 6779 // porphyrin biosynthesis // inferred from electronic annotation /// 9236 // cobalamin biosynthesis // inferred from electronic annotation |
| 23-12A0 yadQ | yadQ | chloride channel protein | 6810 // transport // inferred from electronic annotation /// 6811 // ion transport // inferred from electronic annotation /// 6821 // chloride transport // inferred from electronic annotation |
| yciQ | yciQ | predicted inner membrane protein | — |
| tauB | tauB | Taurine transport ATP-binding protein tauB /// taurine transporter subunit | 6810 // transport // inferred from electronic annotation |
| yagG | yagG | CP4-6 prophage; predicted sugar transporter | 6810 // transport // inferred from electronic annotation /// 6814 // sodium ion transport // inferred from electronic annotation |
| lipA | lipA | lipoyl synthase | 9107 // lipoate biosynthesis // inferred from electronic annotation |
| yhcO | yhcO | Hypothetical protein yhcO /// predicted barnase inhibitor | — |
| maoC | maoC | fused aldehyde dehydrogenase/enoyl-CoA hydratase | 8152 // metabolism // inferred from electronic annotation |
| nfrB | nfrB | Bacteriophage N4 adsorption protein B /// bacteriophage N4 receptor, inner membrane subunit | 6810 // transport // inferred from electronic annotation /// 9597 // detection of virus // inferred from electronic annotation /// 46718 // entry of virus into host cell // inferred from electronic annotation |

TABLE 2-continued

SAM ANALYSIS OF HEALTHY CONTROLS (HC) VERSUS CROHN'S DISEASE (CD) (see FIG. 3A)

| | | | |
|---|---|---|---|
| yajR | yajR | Hypothetical transport protein yajR /// predicted transporter | 6810 // transport // inferred from electronic annotation |
| trkH | trkH | Trk system potassium uptake protein trkH /// potassium transporter | 6810 // transport // inferred from electronic annotation /// 6811 // ion transport // inferred from electronic annotation /// 6812 // cation transport // inferred from electronic annotation /// 6813 // potassium ion transport // inferred from electronic a |
| exuR | exuR | Exu regulon transcriptional regulator /// DNA-binding transcriptional repressor | 6350 // transcription // inferred from electronic annotation /// 6355 // regulation of transcription, DNA-dependent // inferred from electronic annotation |
| glnQ | glnQ | glutamine ABC transporter ATP-binding component /// glutamine ABC transporter ATP-binding protein | 6810 // transport // inferred from electronic annotation /// 6865 // amino acid transport // inferred from electronic annotation |
| yafJ | yafJ | Hypothetical protein yafJ /// predicted amidotransfease | 8152 // metabolism // inferred from electronic annotation |
| ydeF | ydeF /// ydeE | Hypothetical protein ydeE /// predicted transporter | 6810 // transport // inferred from electronic annotation |
| yejF | yejF | Hypothetical ABC transporter ATP-binding protein yejF /// fused predicted oligopeptide transporter subunits of ABC superfamilly: ATP-binding components | 6810 // transport // inferred from electronic annotation /// 6857 // oligopeptide transport // inferred from electronic annotation /// 15031 // protein transport // inferred from electronic annotation |
| yheU | yheU | hypothetical protein | — |
| greA | greA | transcription elongation factor GreA | 6350 // transcription // inferred from electronic annotation /// 6355 // regulation of transcription, DNA-dependent // inferred from electronic annotation |
| yagM | yagM | CP4-6 prophage; predicted protein | — |
| allP | allP /// ybbW | Putative allantoin permease /// predicted allantoin transporter | 6144 // purine base metabolism // inferred from electronic annotation /// 6810 // transport // inferred from electronic annotation /// 15931 // nucleobase, nucleoside, nucleotide and nucleic acid transport // inferred from electronic annotation |
| yghK | yghK | Glycolate permease glcA /// glycolate transporter | 6810 // transport // inferred from electronic annotation /// 15727 // lactate transport // inferred from electronic annotation |
| yjfP | yjfP | Hypothetical protein yjfP /// predicted hydrolase | — |
| 409#5 | yfcP | Hypothetical fimbrial-like protein yfcP precursor | 7155 // cell adhesion |
| yefI | yefI /// wbbK | lipopolysaccharide biosynthesis protein | 9058 // biosynthesis // inferred from electronic annotation /// 9103 // lipopolysaccharide biosynthesis // inferred from electronic annotation |
| ydbD 214#3 | ydbD | hypothetical protein | — |
| yhiN | yhiN | Hypothetical protein yhiN /// predicted oxidoreductase with FAD/NAD(P)-binding domain | 6118 // electron transport // inferred from electronic annotation |
| mutT | mutT | Mutator mutT protein /// nucleoside triphosphate pyrophosphohydrolase, marked preference for dGTP | 6260 // DNA replication // inferred from electronic annotation /// 6281 // DNA |

TABLE 2-continued

SAM ANALYSIS OF HEALTHY CONTROLS (HC) VERSUS
CROHN'S DISEASE (CD) (see FIG. 3A)

| | | | |
|---|---|---|---|
| | | | repair // inferred from electronic annotation /// 6974 // response to DNA damage stimulus // inferred from electronic annotation /// 8299 // isoprenoid biosynthesis // inferred from electronic annotation |
| virK | virK | hypothetical protein | — |
| ompC | ompC | Outer membrane protein C precursor | 6810 // transport // inferred from electronic annotation /// 6811 // ion transport // inferred from electronic annotation /// 9597 // detection of virus // inferred from electronic annotation /// 46718 // entry of virus into host cell // inferred from electronic annotation |
| yghT | yghT | Hypothetical ATP-binding protein yghT /// predicted protein with nucleoside triphosphate hydrolase domain | — |
| yohG | yohG | Putative channel/filament proteins /// predicted outer membrane protein | 6810 // transport // inferred from electronic annotation /// 46677 // response to antibiotic // inferred from electronic annotation |
| ebgA | ebgA | Evolved beta-galactosidase alpha-subunit | 5975 // carbohydrate metabolism // inferred from electronic annotation |
| yjfF | yjfF | Hypothetical ABC transporter permease protein yjfF | 6810 // transport // inferred from electronic annotation |
| 452#13 | ygcH | hypothetical protein | — |
| yphG | yphG | Hypothetical protein yphG | — |
| ynaJ | ynaJ | Hypothetical protein ynaJ /// predicted inner membrane protein | — |
| sucD | sucD | succinyl-CoA synthetase alpha subunit /// succinyl-CoA synthetase subunit alpha | 6099 // tricarboxylic acid cycle // inferred from electronic annotation /// 8152 // metabolism // inferred from electronic annotation |
| prtC | prtC | hypothetical protein | — |
| yhdT | yhdT | Hypothetical protein yhdT /// conserved inner membrane protein | — |
| (yhiW) | yhiW | Hypothetical transcriptional regulator yhiW | 6350 // transcription // inferred from electronic annotation /// 6355 // regulation of transcription, DNA-dependent // inferred from electronic annotation /// 45449 // regulation of transcription // inferred from electronic annotation |
| 610#6.1 | | | |

| | SPOT | GO CC | GO MF |
|---|---|---|---|
| | | 81 Highly immunogenic proteins in CD | |
| | yfiC | — | 8168 // methyltransferase activity // inferred from electronic annotation /// 16740 // transferase activity // inferred from electronic annotation |
| | era | 5622 // intracellular // inferred from electronic annotation /// 16020 // membrane // inferred from electronic annotation | 166 // nucleotide binding // inferred from electronic annotation /// 3676 // nucleic acid binding // inferred from electronic annotation /// 3723 // RNA binding // inferred from electronic annotation /// 5525 // GTP binding // inferred from electronic annotation |
| | ygbD | — | 15036 // disulfide oxidoreductase activity // inferred from electronic annotation /// 16491 // |

TABLE 2-continued

SAM ANALYSIS OF HEALTHY CONTROLS (HC) VERSUS
CROHN'S DISEASE (CD) (see FIG. 3A)

| | | |
|---|---|---|
| | | oxidoreductase activity // inferred from electronic annotation /// 16731 // oxidoreductase activity, acting on iron-sulfur proteins as donors, NAD or NADP as acceptors |
| yjhO | — | 16787 // hydrolase activity // inferred from electronic annotation |
| aidA | — | 5515 // protein binding // inferred from physical interaction /// 3677 // DNA binding // inferred from electronic annotation /// 3905 // alkylbase DNA N-glycosylase activity // inferred from electronic annotation /// 16787 // hydrolase activity // inferred from electronic annotation |
| yhcI | — | 166 // nucleotide binding // inferred from electronic annotation /// 5524 // ATP binding // inferred from electronic annotation /// 9384 // N-acylmannosamine kinase activity // inferred from electronic annotation /// 16301 // kinase activity // inferred from electronic annotation |
| fliS | 9288 // flagellum (sensu Bacteria) // inferred from electronic annotation /// 19861 // flagellum // inferred from electronic annotation | — |
| infC | — | 3743 // translation initiation factor activity // inferred from electronic annotation /// 3723 // RNA binding // inferred from electronic annotation |
| metB | — | 3962 // cystathionine gamma-synthase activity // inferred from electronic annotation /// 16740 // transferase activity // inferred from electronic annotation /// 16829 // lyase activity // inferred from electronic annotation |
| purM | 5737 // cytoplasm // inferred from electronic annotation | 3824 // catalytic activity // inferred from electronic annotation /// 4641 // phosphoribosylformylglycinamidine cyclo-ligase activity // inferred from electronic annotation /// 16874 // ligase activity // inferred from electronic annotation |
| argC | 5737 // cytoplasm // inferred from electronic annotation | 3942 // N-acetyl-gamma-glutamyl-phosphate reductase activity // inferred from electronic annotation /// 16491 // oxidoreductase activity // inferred from electronic annotation /// 16620 // oxidoreductase activity, acting on the aldehyde or oxo group of do |
| phnB | — | — |
| torA | 42597 // periplasmic space // inferred from electronic annotation | 16491 // oxidoreductase activity // inferred from electronic annotation /// 30151 // molybdenum ion binding // inferred from electronic annotation /// 50626 // trimethylamine-N-oxide reductase (cytochrome c) activity // inferred from electronic annotation |
| ibpB | — | 5515 // protein binding // inferred from physical interaction /// 51082 // unfolded protein binding // inferred from electronic annotation |
| hycF | — | 5506 // iron ion binding // inferred from electronic annotation /// 9055 |

TABLE 2-continued

SAM ANALYSIS OF HEALTHY CONTROLS (HC) VERSUS CROHN'S DISEASE (CD) (see FIG. 3A)

| | | |
|---|---|---|
| | | // electron carrier activity // inferred from electronic annotation /// 46872 // metal ion binding // inferred from electronic annotation /// 51536 // iron-sulfur cluster binding // |
| ycbF | 9289 // fimbrium // inferred from electronic annotation /// 30288 // periplasmic space (sensu Proteobacteria) // inferred from electronic annotation /// 42597 // periplasmic space // inferred from electronic annotation | 5515 // protein binding // inferred from electronic annotation /// 51082 // unfolded protein binding // inferred from electronic annotation |
| ssi6 | — | — |
| yjhE | 16020 // membrane // inferred from electronic annotation /// 16021 // integral to membrane // inferred from electronic annotation | 5215 // transporter activity // inferred from electronic annotation |
| ygeW | — | 4070 // aspartate carbamoyltransferase activity // inferred from electronic annotation /// 16597 // amino acid binding // inferred from electronic annotation /// 16743 // carboxyl- and carbamoyltransferase activity // inferred from electronic annotation |
| hofH | 15627 // type II protein secretion system complex // inferred from electronic annotation | 8565 // protein transporter activity // inferred from electronic annotation |
| rffD | — | 16491 // oxidoreductase activity // inferred from electronic annotation |
| yjhC | — | 16491 // oxidoreductase activity // inferred from electronic annotation |
| yjcS | — | 5488 // binding // inferred from electronic annotation |
| ftn | — | 4322 // ferroxidase activity // inferred from electronic annotation /// 5488 // binding // inferred from electronic annotation /// 5506 // iron ion binding // inferred from electronic annotation /// 8199 // ferric iron binding // inferred from electronic |
| ybbQ | — | 4616 // phosphogluconate dehydrogenase (decarboxylating) activity // inferred from electronic annotation /// 8442 // 3-hydroxyisobutyrate dehydrogenase activity // inferred from electronic annotation /// 8679 // 2-hydroxy-3-oxopropionate reductase activit |
| ppdB | — | |
| fimC | 9289 // fimbrium // inferred from electronic annotation /// 30288 // periplasmic space (sensu Proteobacteria) // | 5515 // protein binding // inferred from electronic annotation /// 51082 // unfolded protein binding // inferred from electronic annotation |

TABLE 2-continued

SAM ANALYSIS OF HEALTHY CONTROLS (HC) VERSUS CROHN'S DISEASE (CD) (see FIG. 3A)

| | | |
|---|---|---|
| | inferred from electronic annotation /// 42597 // periplasmic space // inferred from electronic annotation | |
| dgxA | — | — |
| fumB | — | 3824 // catalytic activity // inferred from electronic annotation /// 4333 // fumarate hydratase activity // inferred from electronic annotation /// 5506 // iron ion binding // inferred from electronic annotation /// 16829 // lyase activity // inferred from electronic annotation |
| (thiS) | — | — |
| yjeJ | — | — |
| cedA | — | — |
| cysW | 9276 // cell wall (sensu Proteobacteria) // inferred from electronic annotation /// 16020 // membrane // inferred from electronic annotation /// 16021 // integral to membrane // inferred from electronic annotation | 5215 // transporter activity // inferred from electronic annotation /// 15116 // sulfate transporter activity // inferred from electronic annotation /// 15563 // uptake permease activity // inferred from electronic annotation |
| ygcQ | — | 9055 // electron carrier activity // inferred from electronic annotation /// 50660 // FAD binding // inferred from electronic annotation |
| rpsR | 5622 // intracellular // inferred from electronic annotation /// 5840 // ribosome // inferred from electronic annotation /// 30529 // ribonucleoprotein complex // inferred from electronic annotation | 3723 // RNA binding // inferred from electronic annotation /// 3735 // structural constituent of ribosome // inferred from electronic annotation /// 19843 // rRNA binding // inferred from electronic annotation |
| narY | 9325 // nitrate reductase complex // inferred from electronic annotation /// 16020 // membrane // inferred from electronic annotation | 5506 // iron ion binding // inferred from electronic annotation /// 8940 // nitrate reductase activity // inferred from electronic annotation /// 9055 // electron carrier activity // inferred from electronic annotation /// 16491 // oxidoreductase activity |
| citB | 5737 // cytoplasm // inferred from electronic annotation | 156 // two-component response regulator activity // inferred from electronic annotation /// 3677 // DNA binding // inferred from electronic annotation /// 30528 // transcription regulator activity // inferred from electronic annotation |
| yjbR | — | — |
| ybbA | — | 166 // nucleotide binding // inferred from electronic annotation /// 5524 // ATP binding // inferred from |

TABLE 2-continued

SAM ANALYSIS OF HEALTHY CONTROLS (HC) VERSUS CROHN'S DISEASE (CD) (see FIG. 3A)

| Gene | Cellular Component | Molecular Function |
|---|---|---|
| | | electronic annotation /// 5525 // GTP binding // inferred from electronic annotation /// 16887 // ATPase activity // inferred from electronic annotation |
| gst | — | 4364 // glutathione transferase activity // inferred from electronic annotation /// 16740 // transferase activity // inferred from electronic annotation |
| grxC | — | 9055 // electron carrier activity // inferred from electronic annotation /// 15035 // protein disulfide oxidoreductase activity // inferred from electronic annotation |
| cysD | — | 4781 // sulfate adenylyltransferase (ATP) activity // inferred from electronic annotation /// 16740 // transferase activity // inferred from electronic annotation /// 16779 // nucleotidyltransferase activity // inferred from electronic annotation |
| radC | — | — |
| citG | — | 16740 // transferase activity // inferred from electronic annotation /// 46917 // triphosphoribosyl-dephospho-CoA synthase activity // inferred from electronic annotation |
| fdhE | — | 5506 // iron ion binding // inferred from electronic annotation /// 9055 // electron carrier activity // inferred from electronic annotation /// 20037 // heme binding // inferred from electronic annotation |
| fecB | 42597 // periplasmic space // inferred from electronic annotation | 5381 // iron ion transporter activity // inferred from electronic annotation /// 5506 // iron ion binding // inferred from electronic annotation |
| yhgH (phnE) | — | — |
| | 5887 // integral to plasma membrane // inferred from electronic annotation /// 16020 // membrane // inferred from electronic annotation /// 16021 // integral to membrane // inferred from electronic annotation | 5215 // transporter activity // inferred from electronic annotation /// 15604 // phosphonate transporter activity// inferred from electronic annotation |
| cysJ | — | 5515 // protein binding // inferred from physical interaction /// 4783 // sulfite reductase (NADPH) activity // inferred from electronic annotation /// 5506 // iron ion binding // inferred from electronic annotation /// 9055 // electron carrier activity / |
| 445#15 | 16020 // membrane /// 16021 // integral to membrane | 5215 // transporter activity |
| fba | — | 5515 // protein binding // inferred from physical interaction /// 4332 // fructose-bisphosphate aldolase activity // inferred from electronic annotation /// 8270 // zinc ion binding // inferred from electronic annotation /// 16829 // lyase activity // inferred from electronic annotation |

TABLE 2-continued

SAM ANALYSIS OF HEALTHY CONTROLS (HC) VERSUS CROHN'S DISEASE (CD) (see FIG. 3A)

| Gene | Col 2 | Col 3 |
|---|---|---|
| yjbI | — | — |
| yfjQ | — | — |
| mltB | — | 16787 // hydrolase activity // inferred from electronic annotation /// 16798 // hydrolase activity, acting on glycosyl bonds // inferred from electronic annotation |
| yhaA | 5622 // intracellular // inferred from electronic annotation | 8776 // acetate kinase activity // inferred from electronic annotation /// 16301 // kinase activity // inferred from electronic annotation /// 16740 // transferase activity // inferred from electronic annotation /// 16774 // phosphotransferase activity, c |
| yjeB | — | 3677 // DNA binding // inferred from electronic annotation /// 4826 phenylalanine-tRNA ligase activity // inferred from electronic annotation /// 5524 // ATP binding // inferred from electronic annotation |
| thiF | — | 3824 // catalytic activity // inferred from electronic annotation /// 16740 // transferase activity // inferred from electronic annotation /// 16779 // nucleotidyltransferase activity // inferred from electronic annotation |
| gcpE | — | 5506 // iron ion binding // inferred from electronic annotation /// 16491 // oxidoreductase activity // inferred from electronic annotation /// 16728 // oxidoreductase activity, acting on CH2 groups, disulfide as acceptor // inferred from electronic annotation |
| mviN | 16020 // membrane // inferred from electronic annotation /// 16021 // integral to membrane // inferred from electronic annotation | — |
| yihK | 5622 // intracellular // inferred from electronic annotation | 5515 // protein binding // inferred from physical interaction /// 166 // nucleotide binding // inferred from electronic annotation /// 5525 // GTP binding // inferred from electronic annotation |
| ubiG | — | 5515 // protein binding // inferred from physical interaction /// 8168 // methyltransferase activity // inferred from electronic annotation /// 8425 // 2-polyprenyl-6-methoxy-1,4-benzoquinone methyltransferase activity // inferred from electronic annotati |
| yejG | — | — |
| 304#1 | — | — |
| ygfY | — | — |
| 319#17 | — | — |
| 336#6 | | |
| 430#8 | — | — |
| yhfR | 5622 // intracellular // inferred from electronic annotation | 5515 // protein binding // inferred from physical interaction /// 3677 // DNA binding // inferred from electronic annotation /// 3700 // transcription factor activity // inferred from electronic annotation /// 30528 // transcription regulator activity // |
| phnG | — | — |
| ymfE | 16020 // membrane // inferred from | — |

TABLE 2-continued

SAM ANALYSIS OF HEALTHY CONTROLS (HC) VERSUS CROHN'S DISEASE (CD) (see FIG. 3A)

| | | |
|---|---|---|
| | electronic annotation /// 16021 // integral to membrane // inferred from electronic annotation | |
| yejO | 16020 // membrane // inferred from electronic annotation /// 19867 // outer membrane // inferred from electronic annotation | 5524 // ATP binding // inferred from electronic annotation |
| dicC | — | 3677 // DNA binding // inferred from electronic annotation |
| galR | 5622 // intracellular // inferred from electronic annotation | 3677 // DNA binding // inferred from electronic annotation /// 3700 // transcription factor activity // inferred from electronic annotation |
| yphC | — | 8270 // zinc ion binding // inferred from electronic annotation /// 16491 // oxidoreductase activity // inferred from electronic annotation /// 46872 // metal ion binding // inferred from electronic annotation |
| rplT | 5622 // intracellular // inferred from electronic annotation /// 5840 // ribosome // inferred from electronic annotation /// 30529 // ribonucleoprotein complex // inferred from electronic annotation | 3723 // RNA binding // inferred from electronic annotation /// 3735 // structural constituent of ribosome // inferred from electronic annotation /// 19843 // rRNA binding // inferred from electronic annotation |
| 267#6 | — | 8415 // acyltransferase activity /// 16740 // transferase activity |
| selD | — | 166 // nucleotide binding // inferred from electronic annotation /// 287 // magnesium ion binding // inferred from electronic annotation /// 3824 // catalytic activity // inferred from electronic annotation /// 4756 // selenide, water dikinase activity // |
| tdcB | — | 3824 // catalytic activity // inferred from electronic annotation /// 4794 // threonine ammonia-lyase activity // inferred from electronic annotation /// 16829 // lyase activity // inferred from electronic annotation |
| yhfV | — | 8270 // zinc ion binding // inferred from electronic annotation /// 16788 // hydrolase activity, acting on ester bonds // inferred from electronic annotation |
| yjaI | 42597 // periplasmic space // inferred from electronic annotation | 8270 // zinc ion binding // inferred from electronic annotation |
| hycA | — | 16829 // lyase activity // inferred from electronic annotation |
| 192 Highly immunogenic response proteins in HC | | |
| pbuX | — | — |
| fabH | — | 3824 // catalytic |

TABLE 2-continued

SAM ANALYSIS OF HEALTHY CONTROLS (HC) VERSUS CROHN'S DISEASE (CD) (see FIG. 3A)

| | | |
|---|---|---|
| | | activity // inferred from electronic annotation /// 4315 // 3-oxoacyl-[acyl-carrier protein] synthase activity // inferred from electronic annotation /// 8415 // acyltransferase activity // inferred from electronic annotation /// 16740 / |
| glpF | 16020 // membrane // inferred from electronic annotation /// 16021 // integral to membrane // inferred from electronic annotation | 287 // magnesium ion binding // inferred from electronic annotation /// 5215 // transporter activity // inferred from electronic annotation /// 46872 // metal ion binding // inferred from electronic annotation |
| 273#6 | 16020 // membrane /// 16021 // integral to membrane | 5215 // transporter activity |
| ybhR | 16020 // membrane // inferred from electronic annotation /// 16021 // integral to membrane // inferred from electronic annotation | 5524 // ATP binding // inferred from electronic annotation /// 42626 // ATPase activity, coupled to transmembrane movement of substances // inferred from electronic annotation |
| yqcE | 16020 // membrane // inferred from electronic annotation /// 16021 // integral to membrane // inferred from electronic annotation | 5215 // transporter activity // inferred from electronic annotation |
| flhD | 19861 // flagellum // inferred from electronic annotation | 3677 // DNA binding // inferred from electronic annotation /// 3700 // transcription factor activity // inferred from electronic annotation /// 16563 // transcriptional activator activity // inferred from electronic annotation |
| trkG | 16020 // membrane // inferred from electronic annotation /// 16021 // integral to membrane // inferred from electronic annotation | 8324 // cation transporter activity // inferred from electronic annotation /// 30955 // potassium ion binding // inferred from electronic annotation |
| ybdS | 16020 // membrane // inferred from electronic annotation | 5215 // transporter activity // inferred from electronic annotation |
| brnQ | 16020 // membrane // inferred from | 15171 // amino acid transporter activity |

TABLE 2-continued

SAM ANALYSIS OF HEALTHY CONTROLS (HC) VERSUS CROHN'S DISEASE (CD) (see FIG. 3A)

| | | |
|---|---|---|
| | electronic annotation /// 16021 // integral to membrane // inferred from electronic annotation | // inferred from electronic annotation /// 15658 // branched-chain aliphatic amino acid transporter activity // inferred from electronic annotation |
| ycaD | 16020 // membrane // inferred from electronic annotation /// 16021 // integral to membrane // inferred from electronic annotation | 5215 // transporter activity // inferred from electronic annotation |
| ybhN | 16020 // membrane // inferred from electronic annotation /// 16021 // integral to membrane // inferred from electronic annotation | — |
| yabK | 9276 // cell wall (sensu Proteobacteria) // inferred from electronic annotation /// 16020 // membrane // inferred from electronic annotation /// 16021 // integral to membrane // inferred from electronic annotation | 5215 // transporter activity // inferred from electronic annotation |
| ycdG | 16020 // membrane // inferred from electronic annotation /// 16021 // integral to membrane // inferred from electronic annotation | 5215 // transporter activity // inferred from electronic annotation |
| yojI | 16020 // membrane // inferred from electronic annotation /// 16021 // integral to membrane // inferred from electronic annotation | 166 // nucleotide binding // inferred from electronic annotation /// 5524 // ATP binding // inferred from electronic annotation /// 15197 // peptide transporter activity // inferred from electronic annotation /// 16887 // ATPase activity // inferred from electronic annotation |
| ybaN | 16020 // membrane // inferred from electronic annotation /// 16021 // integral to membrane // inferred from electronic annotation | — |
| focA 321#3 | 9289 // fimbrium // inferred from electronic annotation | — |
| yciR | — | 4871 // signal transducer activity // inferred from electronic annotation |

TABLE 2-continued

SAM ANALYSIS OF HEALTHY CONTROLS (HC) VERSUS CROHN'S DISEASE (CD) (see FIG. 3A)

| | | |
|---|---|---|
| 427#1 | 16020 // membrane /// 16021 // integral to membrane | — |
| celD | 5622 // intracellular // inferred from electronic annotation | 3677 // DNA binding // inferred from electronic annotation /// 3700 // transcription factor activity // inferred from electronic annotation /// 43565 // sequence-specific DNA binding // inferred from electronic annotation |
| uidB | 16020 // membrane // inferred from electronic annotation /// 16021 // integral to membrane // inferred from electronic annotation | 5215 // transporter activity // inferred from electronic annotation /// 5351 // sugar porter activity // inferred from electronic annotation /// 15293 // symporter activity // inferred from electronic annotation |
| ydjS | — | 8270 // zinc ion binding // inferred from electronic annotation /// 16787 // hydrolase activity // inferred from electronic annotation /// 16788 // hydrolase activity, acting on ester bonds // inferred from electronic annotation /// 46872 // metal ion bin |
| rocE | — | — |
| emrY | 16020 // membrane // inferred from electronic annotation /// 16021 // integral to membrane // inferred from electronic annotation | 5215 // transporter activity // inferred from electronic annotation /// 3677 // DNA binding // inferred from electronic annotation |
| cydC | 16020 // membrane // inferred from electronic annotation /// 16021 // integral to membrane // inferred from electronic annotation | 166 // nucleotide binding // inferred from electronic annotation /// 5524 // ATP binding // inferred from electronic annotation /// 16887 // ATPase activity // inferred from electronic annotation /// 17111 // nucleoside-triphosphatase activity // inferred from electronic annotation |
| yhhS | 16020 // membrane // inferred from electronic annotation /// 16021 // integral to membrane // inferred from electronic annotation | 5215 // transporter activity // inferred from electronic annotation |

TABLE 2-continued

SAM ANALYSIS OF HEALTHY CONTROLS (HC) VERSUS CROHN'S DISEASE (CD) (see FIG. 3A)

| | | |
|---|---|---|
| 406#7 | — | 3824 // catalytic activity /// 51287 // NAD binding |
| atoE | 16020 // membrane // inferred from electronic annotation /// 16021 // integral to membrane // inferred from electronic annotation | 15635 // short-chain fatty acid transporter activity // inferred from electronic annotation |
| ybgE | — | — |
| JW0438 | 16021 // integral to membrane | 166 // nucleotide binding /// 5524 // ATP binding /// 16887 // ATPase activity /// 17111 // nucleoside-triphosphatase activity /// 42626 // ATPase activity, coupled to transmembrane movement of substances |
| (yhhT) | 16020 // membrane // inferred from electronic annotation /// 16021 // integral to membrane // inferred from electronic annotation | — |
| ybhM | — | — |
| yicO | 16020 // membrane // inferred from electronic annotation /// 16021 // integral to membrane // inferred from electronic annotation | 5215 // transporter activity // inferred from electronic annotation |
| ybhL | 16020 // membrane // inferred from electronic annotation /// 16021 // integral to membrane // inferred from electronic annotation | — |
| yhiQ | — | — |
| ydaA | — | — |
| ydjZ | 16020 // membrane // inferred from electronic annotation /// 16021 // integral to membrane // inferred from electronic annotation | — |
| dnaQ | 5622 // intracellular // inferred from electronic annotation | 287 // magnesium ion binding // inferred from electronic annotation /// 3677 // DNA binding // inferred from electronic annotation /// 3887 // DNA-directed DNA polymerase activity // inferred from electronic annotation /// 4518 // nuclease activity // inferred from electronic annotation |
| yidY | 16020 // membrane // inferred from electronic annotation /// 16021 // integral | 5215 // transporter activity // inferred from electronic annotation |

TABLE 2-continued

SAM ANALYSIS OF HEALTHY CONTROLS (HC) VERSUS CROHN'S DISEASE (CD) (see FIG. 3A)

| | | |
|---|---|---|
| 211#11 dgkA | to membrane // inferred from electronic annotation 16020 // membrane // inferred from electronic annotation /// 16021 // integral to membrane // inferred from electronic annotation | 4143 // diacylglycerol kinase activity // inferred from electronic annotation /// 16301 // kinase activity // inferred from electronic annotation /// 16740 // transferase activity // inferred from electronic annotation |
| secF | 9276 // cell wall (sensu Proteobacteria) // inferred from electronic annotation /// 15627 // type II protein secretion system complex // inferred from electronic annotation /// 16020 // membrane // inferred from electronic annotation /// 16021 // integral | 8565 // protein transporter activity // inferred from electronic annotation /// 15450 // protein translocase activity // inferred from electronic annotation |
| ybbC | — | — |
| fadA | — | 3988 // acetyl-CoA C-acyltransferase activity // inferred from electronic annotation /// 8415 // acyltransferase activity // inferred from electronic annotation /// 16740 // transferase activity // inferred from electronic annotation |
| fepD | 16020 // membrane // inferred from electronic annotation | 5215 // transporter activity // inferred from electronic annotation |
| sdhD | 16020 // membrane // inferred from electronic annotation /// 16021 // integral to membrane // inferred from electronic annotation | 5506 // iron ion binding // inferred from electronic annotation /// 46872 // metal ion binding // inferred from electronic annotation |
| yeiO | 16020 // membrane // inferred from electronic annotation /// 16021 // integral to membrane // inferred from electronic annotation | 5215 // transporter activity // inferred from electronic annotation /// 5351 // sugar porter activity // inferred from electronic annotation /// 15542 // sugar efflux transporter activity // inferred from electronic annotation |
| yhfU | — | — |
| (yeeF) | 16020 // membrane // inferred from electronic annotation /// 16021 // integral to membrane // | 5279 // amino acid-polyamine transporter activity // inferred from electronic |

TABLE 2-continued

SAM ANALYSIS OF HEALTHY CONTROLS (HC) VERSUS CROHN'S DISEASE (CD) (see FIG. 3A)

| | | |
|---|---|---|
| | inferred from electronic annotation | annotation /// 15171 // amino acid transporter activity // inferred from electronic annotation |
| yaeG | — | — |
| nac | — | 3677 // DNA binding // inferred from electronic annotation /// 3700 // transcription factor activity // inferred from electronic annotation |
| msbA | 9276 // cell wall (sensu Proteobacteria) // inferred from electronic annotation /// 16020 // membrane // inferred from electronic annotation /// 16021 // integral to membrane // inferred from electronic annotation | 166 // nucleotide binding // inferred from electronic annotation /// 5524 // ATP binding // inferred from electronic annotation /// 16887 // ATPase activity // inferred from electronic annotation /// 17111 // nucleoside-triphosphatase activity // inferred from electronic annotation |
| narI | 9325 // nitrate reductase complex // inferred from electronic annotation /// 16020 // membrane // inferred from electronic annotation /// 16021 // integral to membrane // inferred from electronic annotation | 5506 // iron ion binding // inferred from electronic annotation /// 8940 // nitrate reductase activity // inferred from electronic annotation /// 16491 // oxidoreductase activity // inferred from electronic annotation /// 46872 // metal ion binding // inferred from electronic annotation |
| oppC | 16020 // membrane // inferred from electronic annotation /// 16021 // integral to membrane // inferred from electronic annotation | 5215 // transporter activity // inferred from electronic annotation /// 15198 // oligopeptide transporter activity // inferred from electronic annotation |
| yibQ | — | — |
| pheP | 16020 // membrane // inferred from electronic annotation /// 16021 // integral to membrane // inferred from electronic annotation | 5279 // amino acid-polyamine transporter activity // inferred from electronic annotation /// 15171 // amino acid transporter activity // inferred from electronic annotation |
| 16-3B0 | | |
| emrD | 16020 // membrane // inferred from electronic annotation /// 16021 // integral to membrane // inferred from | 5215 // transporter activity // inferred from electronic annotation /// 15238 // drug transporter activity // inferred |

TABLE 2-continued

SAM ANALYSIS OF HEALTHY CONTROLS (HC) VERSUS CROHN'S DISEASE (CD) (see FIG. 3A)

| | | electronic annotation | from electronic annotation |
|---|---|---|---|
| | ydeZ | 16020 // membrane // inferred from electronic annotation /// 16021 // integral to membrane // inferred from electronic annotation | 5215 // transporter activity // inferred from electronic annotation |
| | 280#1 | 5618 // cell wall | 8233 // peptidase activity /// 8237 // metallopeptidase activity /// 16787 // hydrolase activity /// 16805 // dipeptidase activity |
| | ybfC | — | — |
| | ydcD | — | — |
| | ygjR | 16020 // membrane // inferred from electronic annotation /// 16021 // integral to membrane // inferred from electronic annotation | 16491 // oxidoreductase activity // inferred from electronic annotation |
| | yehY | 16020 // membrane // inferred from electronic annotation /// 16021 // integral to membrane // inferred from electronic annotation | 5215 // transporter activity // inferred from electronic annotation |
| | ppx | 16020 // membrane // inferred from electronic annotation | 287 // magnesium ion binding // inferred from electronic annotation /// 4309 // exopolyphosphatase activity // inferred from electronic annotation /// 16787 // hydrolase activity // inferred from electronic annotation |
| | nagE | 16020 // membrane // inferred from electronic annotation /// 16021 // integral to membrane // inferred from electronic annotation /// 19866 // organelle inner membrane // inferred from electronic annotation | 5351 // sugar porter activity // inferred from electronic annotation /// 8982 // protein-N(PI)-phosphohistidine-sugar phosphotransferase activity // inferred from electronic annotation |
| | kch | 16020 // membrane // inferred from electronic annotation /// 16021 // integral to membrane // inferred from electronic annotation | 5216 // ion channel activity // inferred from electronic annotation |
| | yjeM | 16020 // membrane // inferred from electronic annotation /// 16021 // integral to membrane // inferred from electronic annotation | 5279 // amino acid-polyamine transporter activity // inferred from electronic annotation |
| | ybfB | 16020 // membrane // inferred from electronic annotation /// 16021 // integral to membrane // | — |

TABLE 2-continued

SAM ANALYSIS OF HEALTHY CONTROLS (HC) VERSUS CROHN'S DISEASE (CD) (see FIG. 3A)

| | | |
|---|---|---|
| 279#6 | inferred from electronic annotation 16020 // membrane /// 16021 // integral to membrane | 5215 // transporter activity |
| aqpZ | 16020 // membrane // inferred from electronic annotation /// 16021 // integral to membrane // inferred from electronic annotation | 5215 // transporter activity // inferred from electronic annotation /// 15250 // water channel activity // inferred from electronic annotation |
| yhjX | 16020 // membrane // inferred from electronic annotation /// 16021 // integral to membrane // inferred from electronic annotation | 5215 // transporter activity // inferred from electronic annotation /// 15297 // antiporter activity // inferred from electronic annotation |
| malX | 16020 // membrane // inferred from electronic annotation /// 16021 // integral to membrane // inferred from electronic annotation | 5351 // sugar porter activity // inferred from electronic annotation /// 8982 // protein-N(PI)-phosphohistidine-sugar phosphotransferase activity // inferred from electronic annotation /// 16740 // transferase activity // inferred from electronic annotati |
| ycbM | 16020 // membrane // inferred from electronic annotation /// 16021 // integral to membrane // inferred from electronic annotation | 5215 // transporter activity // inferred from electronic annotation |
| narU | 16020 // membrane // inferred from electronic annotation /// 16021 // integral to membrane // inferred from electronic annotation | 15103 // inorganic anion transporter activity // inferred from electronic annotation |
| lpxC | — | 8759 // UDP-3-O-[3-hydroxymyristoyl] N-acetylglucosamine deacetylase activity // inferred from electronic annotation /// 16787 // hydrolase activity // inferred from electronic annotation |
| secY/prlA | 16020 // membrane // inferred from electronic annotation /// 16021 // integral to membrane // inferred from electronic annotation | 15450 // protein translocase activity // inferred from electronic annotation |
| (yhcP) | 16020 // membrane // inferred from electronic annotation /// 16021 // integral to membrane // inferred from electronic annotation | — |

TABLE 2-continued

SAM ANALYSIS OF HEALTHY CONTROLS (HC) VERSUS CROHN'S DISEASE (CD) (see FIG. 3A)

| | | |
|---|---|---|
| phsE | 5618 // cell wall // inferred from electronic annotation /// 16020 // membrane // inferred from electronic annotation | 4180 // carboxypeptidase activity // inferred from electronic annotation /// 8233 // peptidase activity // inferred from electronic annotation /// 9002 // serine-type D-Ala-D-Ala carboxypeptidase activity // inferred from electronic annotation /// 16787 / |
| hemY | 16020 // membrane // inferred from electronic annotation /// 16021 // integral to membrane // inferred from electronic annotation | — |
| yciS | 16020 // membrane // inferred from electronic annotation /// 16021 // integral to membrane // inferred from electronic annotation | — |
| malZ | — | 3824 // catalytic activity // inferred from electronic annotation /// 4558 // alpha-glucosidase activity // inferred from electronic annotation /// 16787 // hydrolase activity // inferred from electronic annotation /// 16798 // hydrolase activity, acting |
| ymdD | 16020 // membrane // inferred from electronic annotation /// 16021 // integral to membrane // inferred from electronic annotation | 8415 // acyltransferase activity // inferred from electronic annotation /// 16740 // transferase activity // inferred from electronic annotation /// 16741 // transferase activity, transferring one-carbon groups // inferred from electronic annotation /// 1 |
| 316#4 | — | — |
| rfaB | — | 16740 // transferase activity // inferred from electronic annotation /// 16757 // transferase activity, transferring glycosyl groups // inferred from electronic annotation |
| emrB | 16020 // membrane // inferred from electronic annotation /// 16021 // integral to membrane // inferred from electronic annotation | 5215 // transporter activity // inferred from electronic annotation |

TABLE 2-continued

SAM ANALYSIS OF HEALTHY CONTROLS (HC) VERSUS CROHN'S DISEASE (CD) (see FIG. 3A)

| | | |
|---|---|---|
| 356#7 | — | — |
| fsr | 16020 // membrane // inferred from electronic annotation /// 16021 // integral to membrane // inferred from electronic annotation | 5215 // transporter activity // inferred from electronic annotation |
| yigF | — | — |
| 233#6 | 16020 // membrane /// 16021 // integral to membrane | 5506 // iron ion binding /// 46872 // metal ion binding |
| 331#2 | — | 16491 // oxidoreductase activity |
| mrdB | 9276 // cell wall (sensu Proteobacteria) // inferred from electronic annotation /// 16021 // integral to membrane // inferred from electronic annotation | — |
| thiL | — | 9030 // thiamin phosphate kinase activity // inferred from electronic annotation /// 16301 // kinase activity // inferred from electronic annotation /// 16740 // transferase activity // inferred from electronic annotation |
| yphD | 16020 // membrane // inferred from electronic annotation /// 16021 // integral to membrane // inferred from electronic annotation | 5215 // transporter activity // inferred from electronic annotation |
| fabZ | 5737 // cytoplasm // inferred from electronic annotation | 16829 // lyase activity // inferred from electronic annotation /// 16836 // hydro-lyase activity // inferred from electronic annotation |
| yoaA | — | 166 // nucleotide binding // inferred from electronic annotation /// 3676 // nucleic acid binding // inferred from electronic annotation /// 3677 // DNA binding // inferred from electronic annotation /// 4386 // helicase activity // inferred from electronic annotation |
| yfjY | — | — |
| nrfE | 16020 // membrane // inferred from electronic annotation /// 16021 // integral to membrane // inferred from electronic annotation | 15232 // heme transporter activity // inferred from electronic annotation |

TABLE 2-continued

SAM ANALYSIS OF HEALTHY CONTROLS (HC) VERSUS CROHN'S DISEASE (CD) (see FIG. 3A)

| | | |
|---|---|---|
| udk | — | 166 // nucleotide binding // inferred from electronic annotation /// 4849 // uridine kinase activity // inferred from electronic annotation /// 5524 // ATP binding // inferred from electronic annotation /// 16301 // kinase activity // inferred from electronic annotation |
| yhhL | — | — |
| JW1949 | — | — |
| sucB | 45252 // oxoglutarate dehydrogenase complex // inferred from electronic annotation | 4149 // dihydrolipoyllysine-residue succinyltransferase activity // inferred from electronic annotation /// 5515 // protein binding // inferred from electronic annotation /// 8415 // acyltransferase activity // inferred from electronic annotation /// 1674 |
| aceF | 45254 // pyruvate dehydrogenase complex // inferred from electronic annotation | 5515 // protein binding // inferred from physical interaction /// 4742 // dihydrolipoyllysine-residue acetyltransferase activity // inferred from electronic annotation /// 5515 // protein binding // inferred from electronic annotation /// 8415 // acyltran |
| yaiV | 5622 // intracellular // inferred from electronic annotation | 3700 // transcription factor activity // inferred from electronic annotation |
| yccY | — | 4721 // phosphoprotein phosphatase activity // inferred from electronic annotation /// 4725 // protein tyrosine phosphatase activity // inferred from electronic annotation /// 16787 // hydrolase activity // inferred from electronic annotation |
| yhaO | 16020 // membrane // inferred from electronic annotation /// 16021 // integral to membrane // inferred from electronic annotation | 5215 // transporter activity // inferred from electronic annotation |

TABLE 2-continued

SAM ANALYSIS OF HEALTHY CONTROLS (HC) VERSUS CROHN'S DISEASE (CD) (see FIG. 3A)

| | | |
|---|---|---|
| yhiP | 16020 // membrane // inferred from electronic annotation /// 16021 // integral to membrane // inferred from electronic annotation | 5215 // transporter activity // inferred from electronic annotation |
| yaaH | 16020 // membrane // inferred from electronic annotation /// 16021 // integral to membrane // inferred from electronic annotation | — |
| oppF | 16020 // membrane // inferred from electronic annotation | 166 // nucleotide binding // inferred from electronic annotation /// 5524 // ATP binding // inferred from electronic annotation /// 15197 // peptide transporter activity // inferred from electronic annotation /// 15198 // oligopeptide transporter activity |
| pnuC | 16020 // membrane // inferred from electronic annotation /// 16021 // integral to membrane // inferred from electronic annotation | — |
| ansP | 16020 // membrane // inferred from electronic annotation /// 16021 // integral to membrane // inferred from electronic annotation | 5279 // amino acid-polyamine transporter activity // inferred from electronic annotation /// 15171 // amino acid transporter activity // inferred from electronic annotation |
| cybB | 16020 // membrane // inferred from electronic annotation /// 16021 // integral to membrane // inferred from electronic annotation | 5506 // iron ion binding // inferred from electronic annotation /// 46872 // metal ion binding // inferred from electronic annotation |
| yddH | — | 16491 // oxidoreductase activity // inferred from electronic annotation |
| sfsA | — | 3677 // DNA binding // inferred from electronic annotation |
| slyX | — | — |
| dinI | — | — |
| ynjC | 16020 // membrane // inferred from electronic annotation /// 16021 // integral to membrane // inferred from electronic annotation | 5215 // transporter activity // inferred from electronic annotation |
| 411#1 | 16020 // membrane /// 16021 // integral to membrane | — |

TABLE 2-continued

SAM ANALYSIS OF HEALTHY CONTROLS (HC) VERSUS CROHN'S DISEASE (CD) (see FIG. 3A)

| | | |
|---|---|---|
| yjgT | 16020 // membrane // inferred from electronic annotation /// 16021 // integral to membrane // inferred from electronic annotation | 5351 // sugar porter activity // inferred from electronic annotation /// 15128 // gluconate transporter activity // inferred from electronic annotation |
| yheG | 5622 // intracellular // inferred from electronic annotation /// 15627 // type II protein secretion system complex // inferred from electronic annotation | 166 // nucleotide binding // inferred from electronic annotation /// 5524 // ATP binding // inferred from electronic annotation /// 8565 // protein transporter activity // inferred from electronic annotation /// 17111 // nucleoside-triphosphatase activity |
| dgt | — | 287 // magnesium ion binding // inferred from electronic annotation /// 3824 // catalytic activity // inferred from electronic annotation /// 8832 // dGTPase activity // inferred from electronic annotation /// 16787 // hydrolase activity // inferred from |
| folK | — | 3848 // 2-amino-4-hydroxy-6-hydroxymethyldihydropteridine diphosphokinase activity // inferred from electronic annotation /// 16301 // kinase activity // inferred from electronic annotation /// 16740 // transferase activity // inferred from electronic annotation |
| gppA | — | 8894 // guanosine-5'-triphosphate,3'-diphosphate diphosphatase activity // inferred from electronic annotation /// 16787 // hydrolase activity // inferred from electronic annotation |
| glnD | — | 3824 // catalytic activity // inferred from electronic annotation /// 8773 // [protein-PII] uridylyltransferase activity // inferred from electronic annotation /// 16597 // amino acid binding // inferred from electronic |

TABLE 2-continued

SAM ANALYSIS OF HEALTHY CONTROLS (HC) VERSUS CROHN'S DISEASE (CD) (see FIG. 3A)

| | | |
|---|---|---|
| | | annotation /// 16740 // transferase |
| yhbX | 16020 // membrane // inferred from electronic annotation /// 16021 // integral to membrane // inferred from electronic annotation | 8484 // sulfuric ester hydrolase activity // inferred from electronic annotation |
| ygjQ | — | — |
| 323#1 | — | — |
| cydB | 16020 // membrane // inferred from electronic annotation /// 16021 // integral to membrane // inferred from electronic annotation | 5506 // iron ion binding // inferred from electronic annotation /// 16491 // oxidoreductase activity // inferred from electronic annotation /// 46872 // metal ion binding // inferred from electronic annotation |
| ybhA | 16020 // membrane // inferred from electronic annotation | 287 // magnesium ion binding // inferred from electronic annotation /// 3824 // catalytic activity // inferred from electronic annotation /// 5524 // ATP binding // inferred from electronic annotation /// 15662 // ATPase activity, coupled to transmembrane |
| yibL | — | — |
| yifE | — | — |
| ygfF | — | 5515 // protein binding // inferred from physical interaction /// 16491 // oxidoreductase activity // inferred from electronic annotation |
| rffG | — | 3824 // catalytic activity // inferred from electronic annotation /// 8460 // dTDP-glucose 4,6-dehydratase activity // inferred from electronic annotation /// 16829 // lyase activity // inferred from electronic annotation /// 50662 // coenzyme binding // |
| yeaS | 16020 // membrane // inferred from electronic annotation /// 16021 // integral to membrane // inferred from electronic annotation | 5293 // lysine permease activity // inferred from electronic annotation |
| yaiM | — | 4759 // serine esterase activity // inferred from electronic annotation /// 16787 // hydrolase activity |

TABLE 2-continued

SAM ANALYSIS OF HEALTHY CONTROLS (HC) VERSUS
CROHN'S DISEASE (CD) (see FIG. 3A)

| | | |
|---|---|---|
| | | // inferred from electronic annotation /// 4091 // carboxylesterase activity // inferred from electronic annotation |
| ygeD | 16020 // membrane // inferred from electronic annotation /// 16021 // integral to membrane // inferred from electronic annotation | — |
| yjhB | 16020 // membrane // inferred from electronic annotation /// 16021 // integral to membrane // inferred from electronic annotation | 5215 // transporter activity // inferred from electronic annotation |
| codB | 16020 // membrane // inferred from electronic annotation /// 16021 // integral to membrane // inferred from electronic annotation | 15205 // nucleobase transporter activity // inferred from electronic annotation |
| rfaL | 16020 // membrane // inferred from electronic annotation /// 16021 // integral to membrane // inferred from electronic annotation | 16874 // ligase activity // inferred from electronic annotation |
| yiaQ | — | 5515 // protein binding // inferred from physical interaction /// 287 // magnesium ion binding // inferred from electronic annotation /// 4590 // orotidine-5'-phosphate decarboxylase activity // inferred from electronic annotation /// 16829 // lyase activ |
| potC | 16020 // membrane // inferred from electronic annotation /// 16021 // integral to membrane // inferred from electronic annotation | 5215 // transporter activity // inferred from electronic annotation |
| secB | — | 51082 // unfolded protein binding // inferred from electronic annotation |
| murG | 5618 // cell wall // inferred from electronic annotation /// 9276 // cell wall (sensu Proteobacteria) // inferred from electronic annotation /// 16020 // membrane // inferred from electronic annotation | 16740 // transferase activity // inferred from electronic annotation /// 16757 // transferase activity, transferring glycosyl groups // inferred from electronic annotation /// 16758 // transferase activity, transferring hexosyl groups // inferred from |

TABLE 2-continued

SAM ANALYSIS OF HEALTHY CONTROLS (HC) VERSUS CROHN'S DISEASE (CD) (see FIG. 3A)

| | | |
|---|---|---|
| ydhV | — | electronic annotation 16491 // oxidoreductase activity // inferred from electronic annotation /// 16730 // oxidoreductase activity, acting on iron-sulfur proteins as donors // inferred from electronic annotation |
| putP | 16020 // membrane // inferred from electronic annotation /// 16021 // integral to membrane // inferred from electronic annotation | 5215 // transporter activity // inferred from electronic annotation /// 5298 // proline:sodium symporter activity // inferred from electronic annotation /// 15171 // amino acid transporter activity // inferred from electronic annotation /// 15293 // sympo |
| yiaL | — | — |
| queA | — | 3824 // catalytic activity // inferred from electronic annotation /// 16740 // transferase activity // inferred from electronic annotation /// 16853 // isomerase activity // inferred from electronic annotation |
| yhaH | 16020 // membrane // inferred from electronic annotation /// 16021 // integral to membrane // inferred from electronic annotation | — |
| cobU | — | 166 // nucleotide binding // inferred from electronic annotation /// 3824 // catalytic activity // inferred from electronic annotation /// 5524 // ATP binding // inferred from electronic annotation /// 5525 // GTP binding // inferred from electronic annotation |
| 23-12A0 yadQ | 16020 // membrane // inferred from electronic annotation /// 16021 // integral to membrane // inferred from electronic annotation | 5247 // voltage-gated chloride channel activity // inferred from electronic annotation /// 15297 // antiporter activity // inferred from electronic annotation /// 31404 // chloride ion binding // inferred |

TABLE 2-continued

SAM ANALYSIS OF HEALTHY CONTROLS (HC) VERSUS CROHN'S DISEASE (CD) (see FIG. 3A)

| | | |
|---|---|---|
| yciQ | — | from electronic annotation — |
| tauB | 16020 // membrane // inferred from electronic annotation | 166 // nucleotide binding // inferred from electronic annotation /// 5524 // ATP binding // inferred from electronic annotation /// 15411 // taurine-transporting ATPase activity // inferred from electronic annotation /// 16787 // hydrolase activity // inferred from electronic annotation |
| yagG | 16020 // membrane // inferred from electronic annotation /// 16021 // integral to membrane // inferred from electronic annotation | 5215 // transporter activity // inferred from electronic annotation /// 15293 // symporter activity // inferred from electronic annotation |
| lipA | — | 3824 // catalytic activity // inferred from electronic annotation /// 5506 // iron ion binding // inferred from electronic annotation /// 16740 // transferase activity // inferred from electronic annotation /// 16783 // sulfurtransferase activity // inferred from electronic annotation |
| yhcO | — | — |
| maoC | — | 16491 // oxidoreductase activity // inferred from electronic annotation |
| nfrB | 16020 // membrane // inferred from electronic annotation /// 16021 // integral to membrane // inferred from electronic annotation | 5524 // ATP binding // inferred from electronic annotation |
| yajR | 16020 // membrane // inferred from electronic annotation /// 16021 // integral to membrane // inferred from electronic annotation | 5215 // transporter activity // inferred from electronic annotation |
| trkH | 16020 // membrane // inferred from electronic annotation /// 16021 // integral to membrane // inferred from electronic annotation | 8324 // cation transporter activity // inferred from electronic annotation /// 30955 // potassium ion binding // inferred from electronic annotation |
| exuR | 5622 // intracellular // inferred from electronic annotation | 3677 // DNA binding // inferred from electronic annotation /// 3700 |

TABLE 2-continued

SAM ANALYSIS OF HEALTHY CONTROLS (HC) VERSUS CROHN'S DISEASE (CD) (see FIG. 3A)

| | | |
|---|---|---|
| | | // transcription factor activity // inferred from electronic annotation |
| glnQ | 16020 // membrane // inferred from electronic annotation | 166 // nucleotide binding // inferred from electronic annotation /// 5524 // ATP binding // inferred from electronic annotation /// 15171 // amino acid transporter activity // inferred from electronic annotation /// 16887 // ATPase activity // inferred from electronic annotation r |
| yafJ | — | 16740 // transferase activity // inferred from electronic annotation |
| ydeF | 16020 // membrane // inferred from electronic annotation /// 16021 // integral to membrane // inferred from electronic annotation | 5215 // transporter activity // inferred from electronic annotation |
| yejF | 16020 // membrane // inferred from electronic annotation | 166 // nucleotide binding // inferred from electronic annotation /// 5524 // ATP binding // inferred from electronic annotation /// 16887 // ATPase activity // inferred from electronic annotation /// 17111 // nucleoside-triphosphatase activity // inferred from electronic annotation |
| yheU | — | — |
| greA | — | 3677 // DNA binding // inferred from electronic annotation /// 3711 // transcriptional elongation regulator activity // inferred from electronic annotation |
| yagM | — | — |
| allP | 16020 // membrane // inferred from electronic annotation /// 16021 // integral to membrane // inferred from electronic annotation | 15205 // nucleobase transporter activity // inferred from electronic annotation |
| yghK | 16020 // membrane // inferred from electronic annotation /// 16021 // integral to membrane // inferred from electronic annotation | 15129 // lactate transporter activity // inferred from electronic annotation |
| yjfP | — | 16787 // hydrolase activity // inferred |

TABLE 2-continued

SAM ANALYSIS OF HEALTHY CONTROLS (HC) VERSUS CROHN'S DISEASE (CD) (see FIG. 3A)

| | | |
|---|---|---|
| 409#5 | 9289 // fimbrium | from electronic annotation — |
| yefI | — | 16740 // transferase activity // inferred from electronic annotation |
| ydbD 214#3 | — | — |
| yhiN | — | 16491 // oxidoreductase activity // inferred from electronic annotation |
| mutT | — | 287 // magnesium ion binding // inferred from electronic annotation /// 4452 // isopentenyl-phosphate delta-isomerase activity // inferred from electronic annotation /// 8413 // 8-oxo-7,8-dihydroguanine triphosphatase activity // inferred from electroni |
| virK | — | — |
| ompC | 16020 // membrane // inferred from electronic annotation /// 16021 // integral to membrane // inferred from electronic annotation /// 19867 // outer membrane // inferred from electronic annotation | 5215 // transporter activity // inferred from electronic annotation /// 15288 // porin activity // inferred from electronic annotation |
| yghT | — | 166 // nucleotide binding // inferred from electronic annotation /// 5524 // ATP binding // inferred from electronic annotation |
| yohG | 16020 // membrane // inferred from electronic annotation /// 19867 // outer membrane // inferred from electronic annotation | 5215 // transporter activity // inferred from electronic annotation /// 8289 // lipid binding // inferred from electronic annotation |
| ebgA | 9341 // beta-galactosidase complex // inferred from electronic annotation | 3824 // catalytic activity // inferred from electronic annotation /// 4553 // hydrolase activity, hydrolyzing O-glycosyl compounds // inferred from electronic annotation /// 4565 // beta-galactosidase activity // inferred from electronic annotation /// 16 |
| yjfF | 16020 // membrane // inferred from electronic annotation | 5215 // transporter activity // inferred from electronic annotation |

TABLE 2-continued

SAM ANALYSIS OF HEALTHY CONTROLS (HC) VERSUS
CROHN'S DISEASE (CD) (see FIG. 3A)

| | | |
|---|---|---|
| 452#13 | — | — |
| yphG | — | 5488 // binding // inferred from electronic annotation |
| ynaJ | 16020 // membrane // inferred from electronic annotation /// 16021 // integral to membrane // inferred from electronic annotation | — |
| sucD | — | 166 // nucleotide binding // inferred from electronic annotation /// 3824 // catalytic activity // inferred from electronic annotation /// 4775 // succinate-CoA ligase (ADP-forming) activity // inferred from electronic annotation /// 5524 // ATP binding / |
| prtC | — | — |
| yhdT | 16020 // membrane // inferred from electronic annotation /// 16021 // integral to membrane // inferred from electronic annotation | — |
| (yhiW) | 5622 // intracellular // inferred from electronic annotation | 3677 // DNA binding // inferred from electronic annotation /// 3700 // transcription factor activity // inferred from electronic annotation /// 43565 // sequence-specific DNA binding // inferred from electronic annotation |
| 610#6.1 | | |

TABLE 3

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| | | 51 Highly immunogenic proteins in UC | | | |
| secF | secF | protein export protein SecF | 6605 // protein targeting // inferred from electronic annotation /// 6810 // transport // inferred from electronic annotation /// 6886 // intracellular protein transport // inferred from electronic annotation /// 15031 // protein transport // inferred from electronic annotation | 9276 // cell wall (sensu Proteobacteria) // inferred from electronic annotation /// 15627 // type II protein secretion system complex // inferred from electronic annotation /// 16020 // membrane // inferred from electronic annotation /// 16021 // integral to membrane // inferred from electronic annotation | 8565 // protein transporter activity // inferred from electronic annotation /// 15450 // protein translocase activity // inferred from electronic annotation |
| 427#1 | yfgF | Hypothetical protein yfgF /// predicted inner membrane protein | | | — |
| yojI | yojI | Hypothetical ABC transporter ATP-binding protein yojI /// fused predicted multidrug transport subunits of ABC superfamily: membrane component/ATP-binding component | 6810 // transport // inferred from electronic annotation /// 15833 // peptide transport // inferred from electronic annotation /// 46677 // response to antibiotic // inferred from electronic annotation | 16020 // membrane // inferred from electronic annotation /// 16021 // integral to membrane // inferred from electronic annotation | 166 // nucleotide binding // inferred from electronic annotation /// 5524 // ATP binding // inferred from electronic annotation /// 15197 // peptide transporter activity // inferred from electronic annotation /// 16887 // ATPase activity // inferred from |
| emrY | emrY | Multidrug resistance protein Y /// predicted multidrug efflux system | 6810 // transport // inferred from electronic annotation /// 6306 // DNA methylation // inferred from electronic annotation | 16020 // membrane // inferred from electronic annotation /// 16021 // integral to membrane // inferred from electronic annotation | 5215 // transporter activity // inferred from electronic annotation /// 3677 // DNA binding // inferred from electronic annotation |
| trkG | trkG | Rac prophage; potassium transporter subunit | 6810 // transport // inferred from electronic annotation | 16020 // membrane // inferred from electronic annotation | 8324 // cation transporter activity // |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| | | | /// 6811 // ion transport // inferred from electronic annotation /// 6812 // cation transport // inferred from electronic annotation /// 6813 // potassium ion transport // inferred from electronic a | | inferred from electronic annotation /// 30955 // potassium ion binding // inferred from electronic annotation |
| yhiN 23-12A0 | yhiN | Hypothetical protein yhiN /// predicted oxidoreductase with FAD/NAD(P)-binding domain | 6118 // electron transport // inferred from electronic annotation | — | 16491 // oxidoreductase activity // inferred from electronic annotation |
| ydaA | ydaA /// uspE | Protein ydaA /// stress-induced protein | 6950 // response to stress // inferred from electronic annotation | — | — |
| nagE | nagE | PTS system, N-acetylglucosamine-specific IIABC component | 6810 // transport // inferred from electronic annotation /// 9401 // phosphoenolpyruvate-dependent sugar phosphotransferase system // inferred from electronic annotation | 16020 // membrane // inferred from electronic annotation /// 16021 // integral to membrane // inferred from electronic annotation /// 19866 // organelle inner membrane // inferred from electronic annotation | 5351 // sugar porter activity // inferred from electronic annotation /// 8982 // protein-N(PI)-phosphohistidine-sugar phosphotransferase activity // inferred from electronic annotation |
| ydhV | ydhV | Hypothetical protein ydhV /// predicted oxidoreductase | 6118 // electron transport // inferred from electronic annotation | — | 16491 // oxidoreductase activity // inferred from electronic annotation /// 16730 // oxidoreductase activity, acting on iron-sulfur proteins as donors // inferred from electronic annotation |
| maoC | maoC | fused aldehyde dehydrogenase/enoyl-CoA hydratase | 8152 // metabolism // inferred from electronic annotation | — | 16491 // oxidoreductase activity // inferred from electronic annotation |
| yaiM | yaiM /// frnB | Hypothetical protein yaiM /// predicted esterase | — | — | 4759 // serine esterase activity // inferred from |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| | | | | | electronic annotation /// 16787 // hydrolase activity // inferred from electronic annotation /// 4091 // carboxylesterase activity // inferred from electronic annotation |
| yeiO | yeiO /// setB | Sugar efflux transporter B /// lactose/glucose efflux system | 6810 // transport // inferred from electronic annotation /// 8643 // carbohydrate transport // inferred from electronic annotation | 16020 // membrane // inferred from electronic annotation /// 16021 // integral to membrane // inferred from electronic annotation | 5215 // transporter activity // inferred from electronic annotation /// 5351 // sugar porter activity // inferred from electronic annotation /// 15542 // sugar efflux transporter activity // inferred from electronic annotation |
| yphD | yphD | predicted sugar transporter subunit: membrane component of ABC superfamily | 6810 // transport // inferred from electronic annotation | 16020 // membrane // inferred from electronic annotation /// 16021 // integral to membrane // inferred from electronic annotation | 5215 // transporter activity // inferred from electronic annotation |
| narI | narI | Respiratory nitrate reductase 1 gamma chain /// nitrate reductase 1, gamma (cytochrome b(NR)) subunit | 6118 // electron transport // inferred from electronic annotation /// 6810 // transport // inferred from electronic annotation /// 42128 // nitrate assimilation // inferred from electronic annotation | 9325 // nitrate reductase complex // inferred from electronic annotation /// 16020 // membrane // inferred from electronic annotation /// 16021 // integral to membrane // inferred from electronic annotation | 5506 // iron ion binding // inferred from electronic annotation /// 8940 // nitrate reductase activity // inferred from electronic annotation /// 16491 // oxidoreductase activity // inferred from electronic annotation /// 46872 // metal ion binding // inf |
| ycbM | ycbM /// ssuC | Putative aliphatic sulfonates transport permease protein ssuC /// alkanesulfonate transporter subunit | 6810 // transport // inferred from electronic annotation | 16020 // membrane // inferred from electronic annotation /// 16021 // integral to | 5215 // transporter activity // inferred from electronic annotation |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| yafJ | yafJ | Hypothetical protein yafJ /// predicted amidotransfease | 8152 // metabolism // inferred from electronic annotation | membrane // inferred from electronic annotation | 16740 // transferase activity // inferred from electronic annotation |
| lueO ybbC (yeeF) | lueO ybbC yeeF | hypothetical protein hypothetical protein Hypothetical transport protein yeeF /// predicted amino-acid transporter | — 6810 // transport // inferred from electronic annotation /// 6865 // amino acid transport // inferred from electronic annotation | — 16020 // membrane // inferred from electronic annotation /// 16021 // integral to membrane // inferred from electronic annotation | — 5279 // amino acid-polyamine transporter activity // inferred from electronic annotation /// 15171 // amino acid transporter activity // inferred from electronic annotation |
| mhpF | mhpF | acetaldehyde dehydrogenase | 6520 // amino acid metabolism // inferred from electronic annotation /// 15976 // carbon utilization // inferred from electronic annotation /// 19439 // aromatic compound catabolism // inferred from electronic annotation | 5737 // cytoplasm // inferred from electronic annotation | 8774 // acetaldehyde dehydrogenase (acetylating) activity // inferred from electronic annotation /// 16491 // oxidoreductase activity // inferred from electronic annotation /// 16620 // oxidoreductase activity, acting on the aldehyde or oxo group of donor |
| rfaB | rfaB | UDP-D-galactose:(glucosyl)lipopolysaccharide-1,6-D-galactosyltransferase | 9058 // biosynthesis // inferred from electronic annotation /// 9103 // lipopolysaccharide biosynthesis // inferred from electronic annotation | — | 16740 // transferase activity // inferred from electronic annotation /// 16757 // transferase activity, transferring glycosyl groups // inferred from electronic annotation |
| yciD | yciD /// ompW | Outer membrane protein W precursor /// outer membrane protein W | — | 16020 // membrane // inferred from electronic annotation /// 19867 // outer membrane // | — |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| dinI | dinI | DNA-damage-inducible protein I /// DNA damage-inducible protein I | 6281 // DNA repair // inferred from electronic annotation /// 6974 // response to DNA damage stimulus // inferred from electronic annotation /// 9432 // SOS response // inferred from electronic annotation | — | inferred from electronic annotation |
| yjgT | yjgT /// idnT | Gnt-II system L-idonate transporter /// L-idonate and D-gluconate transporter | 6810 // transport // inferred from electronic annotation /// 15725 // gluconate transport // inferred from electronic annotation /// 19521 // D-gluconate metabolism // inferred from electronic annotation | 16020 // membrane // inferred from electronic annotation /// 16021 // integral to membrane // inferred from electronic annotation | 5351 // sugar porter activity // inferred from electronic annotation /// 15128 // gluconate transporter activity // inferred from electronic annotation |
| yjiJ | yjiJ | Hypothetical protein yjiJ /// predicted inner membrane protein | — | 16020 // membrane // inferred from electronic annotation /// 16021 // integral to membrane // inferred from electronic annotation | — |
| fsr | fsr | Fosmidomycin resistance protein /// predicted fosmidomycin efflux system | 6810 // transport // inferred from electronic annotation /// 46677 // response to antibiotic // inferred from electronic annotation | 16020 // membrane // inferred from electronic annotation /// 16021 // integral to membrane // inferred from electronic annotation | 5215 // transporter activity // inferred from electronic annotation |
| nac | nac | Nitrogen assimilation Regulatory protein nac /// DNA-binding transcriptional dual regulator of nitrogen assimilation | 6350 // transcription // inferred from electronic annotation /// 6355 // regulation of transcription, DNA-dependent // inferred from electronic annotation /// 42128 // nitrate assimilation // inferred from electronic annotation | — | 3677 // DNA binding // inferred from electronic annotation /// 3700 // transcription factor activity // inferred from electronic annotation |
| msbA | msbA | Probable transport ATP-binding protein | 6810 // transport // inferred | 9276 // cell wall | 166 // nucleotide |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| | | msbA /// fused lipid transporter subunits of ABC superfamily: membrane component/ATP-binding component | from electronic annotation /// 6869 // lipid transport // inferred from electronic annotation | (sensu Proteobacteria) // inferred from electronic annotation /// 16020 // membrane // inferred from electronic annotation /// 16021 // integral to membrane // inferred from electronic annotation | binding // inferred from electronic annotation /// 5524 // ATP binding // inferred from electronic annotation /// 16887 // ATPase activity // inferred from electronic annotation /// 17111 // nucleoside-triphosphatase activity // inferred |
| modC | modC | Molybdenum transport ATP-binding protein modC /// molybdate transporter subunit | 6810 // transport // inferred from electronic annotation /// 15689 // molybdate ion transport // inferred from electronic annotation | 9276 // cell wall (sensu Proteobacteria) // inferred from electronic annotation /// 16020 // membrane // inferred from electronic annotation /// 16021 // integral to membrane // inferred from electronic annotation | 166 // nucleotide binding // inferred from electronic annotation /// 5524 // ATP binding // inferred from electronic annotation /// 15098 // molybdate ion transporter activity // inferred from electronic annotation /// 15412 // molybdate-transporting ATPa |
| kch | kch | Putative potassium channel protein /// voltage-gated potassium channel | 6810 // transport // inferred from electronic annotation /// 6811 // ion transport // inferred from electronic annotation /// 6813 // potassium ion transport // inferred from electronic annotation | 16020 // membrane // inferred from electronic annotation /// 16021 // integral to membrane // inferred from electronic annotation | 5216 // ion channel activity // inferred from electronic annotation |
| prtC | prtC | hypothetical protein | — | — | — |
| yjfH | yjfH /// rlmB | Hypothetical tRNA/rRNA methyltransferase yjfH /// 23S rRNA (Gm2251)-methyltransferase | 6364 // rRNA processing // inferred from electronic annotation /// 6396 // RNA processing // inferred from electronic annotation /// 9451 // RNA modification // inferred from electronic annotation | — | 3723 // RNA binding // inferred from electronic annotation /// 8168 // methyltransferase activity // inferred from electronic annotation /// 8173 // RNA methyltransferase |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| | | | | | activity // inferred from electronic annotation /// 16740 // transferase activity // |
| glnD | glnD | PII uridylyl-transferase | 6807 // nitrogen compound metabolism // inferred from electronic annotation /// 8152 // metabolism // inferred from electronic annotation /// 9399 // nitrogen fixation // inferred from electronic annotation | — | 3824 // catalytic activity // inferred from electronic annotation /// 8773 // [protein-PII] uridylyltransferase activity // inferred from electronic annotation /// 16597 // amino acid binding // inferred from electronic annotation /// 16740 // transferase |
| yhjC | yhjC | Hypothetical transcriptional regulator yhjC /// predicted DNA-binding transcriptional regulator | 6350 // transcription // inferred from electronic annotation /// 6355 // regulation of transcription, DNA-dependent // inferred from electronic annotation | — | 3677 // DNA binding // inferred from electronic annotation /// 3700 // transcription factor activity // inferred from electronic annotation |
| prpE | prpE | predicted propionyl-CoA synthetase with ATPase domain | 8152 // metabolism // inferred from electronic annotation /// 19629 // propionate catabolism, 2-methylcitrate cycle // inferred from electronic annotation | — | 3824 // catalytic activity // inferred from electronic annotation /// 16874 // ligase activity // inferred from electronic annotation /// 50218 // propionate-CoA ligase activity // inferred from electronic annotation |
| 279#6 | ddpC | D-ala-D-ala transporter subunit | 6810 // transport | 16020 // membrane /// 16021 // integral to membrane | 5215 // transporter activity |
| ygiR | ygiR | Hypothetical oxidoreductase ygiR /// predicted NAD(P)-binding dehydrogenase | 6118 // electron transport // inferred from electronic annotation /// 8152 // metabolism // inferred from electronic annotation | 16020 // membrane // inferred from electronic annotation /// 16021 // integral to membrane // inferred from | 16491 // oxidoreductase activity // inferred from electronic annotation |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| ppx | ppx | Exopolyphosphatase | — | 16020 // membrane // inferred from electronic annotation | 287 // magnesium ion binding // inferred from electronic annotation /// 4309 // exopolyphosphatase activity // inferred from electronic annotation /// 16787 // hydrolase activity // inferred from electronic annotation |
| yefI | yefI /// wbbK | lipopolysaccharide biosynthesis protein | 9058 // biosynthesis // inferred from electronic annotation /// 9103 // lipopolysaccharide biosynthesis // inferred from electronic annotation | — | 16740 // transferase activity // inferred, from electronic annotation |
| mesJ | mesJ | Putative cell cycle protein mesJ | 8033 // tRNA processing // inferred from electronic annotation /// 16549 // tRNA editing // inferred from electronic annotation | — | 166 // nucleotide binding // inferred from electronic annotation /// 5524 // ATP binding // inferred from electronic annotation /// 16874 // ligase activity // inferred from electronic annotation /// 16879 // ligase activity, forming carbon-nitrogen bonds |
| secY/prlA | secY /// prlA | preprotein translocase SecY /// protein translocase subunit SecY | 6605 // protein targeting // inferred from electronic annotation /// 6810 // transport // inferred from electronic annotation /// 9306 // protein secretion // inferred from electronic annotation /// 15031 // protein transport // inferred from electronic annotation | 16020 // membrane // inferred from electronic annotation /// 16021 // integral to membrane // inferred from electronic annotation | 15450 // protein translocase activity // inferred from electronic annotation |
| yejA | yejA | Hypothetical protein yejA precursor /// predicted oligopeptide transporter subunit | 6810 // transport // inferred from electronic annotation | — | 5215 // transporter activity // inferred from electronic annotation |
| dgkA | dgkA | Diacylglycerol kinase | 8654 // phospholipid biosynthesis // inferred | 16020 // membrane // inferred from | 4143 // diacylglycerol kinase activity // |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| | | | from electronic annotation | electronic annotation /// 16021 // integral to membrane // inferred from electronic annotation | inferred from electronic annotation /// 16301 // kinase activity // inferred from electronic annotation /// 16740 // transferase activity // inferred from electronic annotation |
| ygcE | ygcE | Hypothetical sugar kinase ygcE | 5975 // carbohydrate metabolism // inferred from electronic annotation | — | 16301 // kinase activity // inferred from electronic annotation |
| focA | focA | F1C major fimbrial subunit precursor | 7155 // cell adhesion // inferred from electronic annotation | 9289 // fimbrium // inferred from electronic annotation | — |
| (rtn) ydbD 211#11 | rtn ydbD | Rtn protein hypothetical protein | — | — | — |
| ygfQ | ygfQ | predicted transporter | 6810 // transport // inferred from electronic annotation | 16020 // membrane // inferred from electronic annotation | 166 // nucleotide binding // inferred from electronic annotation /// 5215 // transporter activity // inferred from electronic annotation /// 5524 // ATP binding // inferred from electronic annotation |
| folK | folK | 2-amino-4-hydroxy-6-hydroxymethyldihydropteridine pyrophosphokinase | 9396 // folic acid and derivative biosynthesis // inferred from electronic annotation | — | 3848 // 2-amino-4-hydroxy-6-hydroxymethyldihydropteridine diphosphokinase activity // inferred from electronic annotation /// 16301 // kinase activity // inferred from electronic annotation /// 16740 // transferase activity // inferred from electronic ann |
| | | 137 Highly immunogenic response proteins in CD | | | |
| frvX | frvX | predicted endo-1,4-beta-glucanase | — | — | 16787 // hydrolase |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| LDR-D 416#1 sugE | sugE | SugE protein | 6810 // transport // inferred from electronic annotation | 16020 // membrane // inferred from electronic annotation /// 16021 // integral to membrane // inferred from electronic annotation | activity // inferred from electronic annotation |
| dinD fecB | dinD fecB | DNA-damage-inducible protein KpLE2 phage-like element; iron-dicitrate transporter subunit | 6810 // transport // inferred from electronic annotation /// 6811 // ion transport // inferred from electronic annotation /// 6826 // iron ion transport // inferred from electronic annotation /// 6827 // high affinity iron ion transport // inferred from electronic annotation | 42597 // periplasmic space // inferred from electronic annotation | 5381 // iron ion transporter activity // inferred from electronic annotation /// 5506 // iron ion binding // inferred from electronic annotation |
| fliA | fliA | flagellar biosynthesis sigma factor FliA /// flagellar biosynthesis sigma factor | 6350 // transcription // inferred from electronic annotation /// 6352 // transcription initiation // inferred from electronic annotation /// 6355 // regulation of transcription, DNA-dependent // inferred from electronic annotation | — | 3677 // DNA binding // inferred from electronic annotation /// 3899 // DNA-directed RNA polymerase activity // inferred from electronic annotation /// 3700 // transcription factor activity // inferred from electronic annotation |
| yjhA | yjhA | Hypothetical protein yjhA precursor /// N-acetylnuraminic acid outer membrane channel protein | 6810 // transport // inferred from electronic annotation /// 6811 // ion transport // inferred from electronic annotation | 16020 // membrane // inferred from electronic annotation /// 16021 // integral to membrane // inferred from electronic annotation | 16740 // transferase ac 5351 // sugar porter activity // inferred from electronic |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| (thiS) | thiS | sulfur carrier protein ThiS | 6790 // sulfur metabolism // inferred from electronic annotation | — | annotation /// 15288 // porin activity // inferred from electronic annotation |
| mcrD | mcrD /// yjiV | hypothetical protein | — | — | — |
| ygbA | ygbA | Hypothetical protein ygbA /// hypothetical protein | — | — | — |
| LDR-ABC | | | | | |
| slyD | slyD | FKBP-type peptidyl-prolyl cis-trans isomerase slyD /// FKBP-type peptidyl prolyl cis-trans isomerase (rotamase) | 6457 // protein folding // inferred from electronic annotation | — | 5515 // protein binding // inferred from physical interaction /// 3755 // peptidyl-prolyl cis-trans isomerase activity // inferred from electronic annotation /// 5507 // copper ion binding // inferred from electronic annotation /// 8270 // zinc ion bindin |
| yliG | yliG | Hypothetical protein yliG /// predicted SAM-dependent methyltransferase | — | — | 3824 // catalytic activity // inferred from electronic annotation /// 5506 // iron ion binding // inferred from electronic annotation /// 46872 // metal ion binding // inferred from electronic annotation /// |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| | | | | | 51536 // iron-sulfur cluster binding // inferre |
| yfiD | yfiD | Protein yfiD /// pyruvate formate lyase subunit | 8152 // metabolism // inferred from electronic annotation | — | 3824 // catalytic activity // inferred from electronic annotation |
| yctF metJ | yctF /// hinT metJ | HIT-like protein yctF /// purine nucleoside phosphoramidase transcriptional repressor protein MetJ | — 6350 // transcription // inferred from electronic annotation /// 6355 // regulation of transcription, DNA-dependent // inferred from electronic annotation /// 6555 // methionine metabolism // inferred from electronic annotation /// 8652 // amino acid bios | — | 3677 // DNA binding // inferred from electronic annotation /// 3700 // transcription factor activity // inferred from electronic annotation /// 16564 // transcriptional repressor activity // inferred from electronic annotation |
| yicC fecR | yicC fecR | Protein yicC KpLE2 phage-like element; transmembrane signal transducer for ferric citrate transport | 6810 // transport // inferred from electronic annotation /// 6811 // ion transport // inferred from electronic annotation /// 6826 // iron ion transport // inferred from electronic annotation /// 50896 // response to stimulus // inferred from electronic a | 42597 // periplasmic space // inferred from electronic annotation | 5506 // iron ion binding // inferred from electronic annotation |
| rpsR | rpsR | 30S ribosomal protein S18 | 6412 // protein biosynthesis // inferred from electronic annotation | 5622 // intracellular // inferred from electronic annotation /// 5840 // ribosome // inferred from electronic annotation /// 30529 // ribonucleoprotein complex // inferred from electronic annotation | 3723 // RNA binding // inferred from electronic annotation /// 3735 // structural constituent of ribosome // inferred from |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| | ycgN | hypothetical protein | | | electronic annotation /// 19843 // rRNA binding // inferred from electronic annotation |
| ycgN 448#2 | noV | pseudo /// anaerobic nitric oxide reductase flavorubredoxin | 6118 // electron transport /// 6810 // transport | — | 5506 // iron ion binding /// 10181 // FMN binding /// 16491 // oxidoreductase activity /// 46872 // metal ion binding |
| rbsB | rbsB | D-ribose-binding periplasmic protein precursor /// D-ribose transporter subunit | 6810 // transport // inferred from electronic annotation /// 6935 // chemotaxis // inferred from electronic annotation | 42597 // periplasmic space // inferred from electronic annotation | 5351 // sugar porter activity // inferred from electronic annotation /// 15407 // monosaccharide-transporting ATPase activity // inferred from electronic annotation /// 16787 // hydrolase activity // inferred from electronic annotation |
| argB | argB | acetylglutamate kinase | 6526 // arginine biosynthesis // inferred from electronic annotation /// 8652 // amino acid biosynthesis // inferred from electronic annotation /// 9085 // lysine biosynthesis // inferred from electronic annotation | 5737 // cytoplasm // inferred from electronic annotation | 166 // nucleotide binding // inferred from electronic annotation /// 3991 // acetylglutamate kinase activity // inferred from |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| | | | | | electronic annotation /// 5524 // ATP binding // inferred from electronic annotation /// 16301 // kinase activity // inferred fro |
| hoxK yfhD | hoxK yfhD | hypothetical protein Hypothetical protein yfhD /// predicted transglycosylase | 6810 // transport // inferred from electronic annotation | 30288 // periplasmic space (sensu Proteobacteria) // inferred from electronic annotation | 5215 // transporter activity // inferred from electronic annotation |
| yjgF fadB | yjgF fadB | Protein yjgF 3-hydroxyacyl-CoA dehydrogenase /// fused 3-hydroxybutyryl-CoA epimerase/delta(3)-cis-delta(2)-trans-enoyl-CoA isomerase/enoyl-CoA hydratase/3-hydroxyacyl-CoA dehydrogenase | 6629 // lipid metabolism // inferred from electronic annotation /// 6631 // fatty acid metabolism // inferred from electronic annotation /// 8152 // metabolism // inferred from electronic annotation /// 9062 // fatty acid catabolism // inferred from elect | 16507 // fatty acid beta-oxidation multienzyme complex // inferred from electronic annotation | 3824 // catalytic activity // inferred from electronic annotation /// 3857 // 3-hydroxyacyl-CoA dehydrogenase activity // inferred from electronic annotation /// 4165 // dodecenoyl-CoA delta-isomerase activity // inferred from electronic annotation /// 43 |
| (phnE) | phnE | membrane channel protein component of Pn transporter | 6810 // transport // inferred from electronic annotation /// 15716 // phosphonate transport // inferred from electronic annotation | 5887 // integral to plasma membrane // inferred from electronic annotation /// 16020 // membrane // inferred from electronic annotation /// 16021 // integral to membrane // inferred from electronic annotation | 5215 // transporter activity // inferred from electronic annotation /// 15604 // phosphonate |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|------|---------|------|-------|-------|-------|
| | | | | | transporter activity // inferred from electronic annotation |
| gabD | gabD | Succinate-semialdehyde dehydrogenase [NADP+] /// succinate-semialdehyde dehydrogenase I, NADP-dependent | 8152 // metabolism // inferred from electronic annotation | — | 9013 // succinate-semialdehyde dehydrogenase [NAD(P)+] activity // inferred from electronic annotation /// 16491 // oxidoreductase activity // inferred from electronic annotation /// 16620 // oxidoreductase activity, acting on the aldehyde or oxo group of |
| rbfA | rbfA | ribosome-binding factor A | 6364 // rRNA processing // inferred from electronic annotation | — | — |
| rpsL | rpsL | 30S ribosomal protein S12 | 6412 // protein biosynthesis // inferred from electronic annotation /// 46677 // response to antibiotic // inferred from electronic annotation | 5622 // intracellular // inferred from electronic annotation /// 5840 // ribosome // inferred from electronic annotation /// 15935 // small ribosomal subunit // inferred from electronic annotation /// 30529 // ribonucleoprotein complex // inferred from electronic annotation | 49 // tRNA binding // inferred from electronic annotation /// 3676 // nucleic acid binding // inferred from electronic annotation /// 3723 // RNA binding // inferred from electronic annotation /// 3735 // structural constituent of ribosome // inferred fro |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| yjbL | yjbL | hypothetical protein | — | — | — |
| nuoE | nuoE | ATP synthase subunit E /// NADH dehydrogenase subunit E | 6120 // mitochondrial electron transport, NADH to ubiquinone // inferred from electronic annotation | — | 5506 // iron ion binding // inferred from electronic annotation /// 8137 // NADH dehydrogenase (ubiquinone) activity // inferred from electronic annotation /// 16491 // oxidoreductase activity // inferred from electronic annotation /// 46872 // metal ion |
| (gntU) | gntU | Low-affinity gluconate transport permease protein, interrupted /// gluconate transporter, low affinity GNT 1 system | 6810 // transport // inferred from electronic annotation /// 15725 // gluconate transport // inferred from electronic annotation /// 19521 // D-gluconate metabolism // inferred from electronic annotation | 16020 // membrane // inferred from electronic annotation /// 16021 // integral to membrane // inferred from electronic annotation | 5351 // sugar porter activity // inferred from electronic annotation /// 15128 // gluconate transporter activity // inferred from electronic annotation |
| rplP | rplP | 50S ribosomal protein L16 | 6412 // protein biosynthesis // inferred from electronic annotation | 5622 // intracellular // inferred from electronic annotation /// 5840 // ribosome // inferred from electronic annotation /// 30529 // ribonucleoprotein complex // inferred from electronic annotation | 49 // tRNA binding // inferred from electronic annotation /// 3723 // RNA binding // inferred from electronic annotation /// 3735 // structural constituent of ribosome // |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| ubiG | ubiG | 3-demethylubiquinone-9 3-methyltransferase | 6744 // ubiquinone biosynthesis // inferred from electronic annotation | — | inferred from electronic annotation /// 19843 // rRNA binding // inferred from elect 5515 // protein binding // inferred from physical interaction /// 8168 // methyltransferase activity // inferred from electronic annotation /// 8425 // 2-polyprenyl-6-methoxy-1,4-benzoquinone methyltransferase activity // inferred from electronic annotati |
| phnG | phnG | PhnG protein /// carbon-phosphonus lyase complex subunit | 15716 // phosphonate transport // inferred from electronic annotation /// 19634 // phosphonate metabolism // inferred from electronic annotation | — | — |
| mviN | mviN | Virulence factor mviN homolog /// predicted inner membrane protein | 9405 // pathogenesis // inferred from electronic annotation | 16020 // membrane // inferred from electronic annotation /// 16021 // integral to membrane // inferred from electronic annotation | — |
| ydfA | ydfA | Hypothetical protein ydfB /// Hypothetical protein ydfA /// Qin prophage; predicted protein | — | — | — |
| rpmJ | rpmJ | 50S ribosomal protein L36 | 6412 // protein biosynthesis // inferred from electronic annotation | 5622 // intracellular // inferred from electronic annotation /// 5840 // ribosome // inferred from electronic annotation /// 30529 // ribonucleoprotein complex // inferred from electronic annotation | 3735 // structural constituent of ribosome // inferred from electronic annotation |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| yihD | yihD | Protein yihD /// hypothetical protein | — | — | — |
| ydfR | ydfR | Hypothetical protein ydfR | — | — | — |
| baiF | baiF | hypothetical protein | — | — | — |
| ygbO | ygbO | tRNA pseudouridine synthase D | 8033 // tRNA processing // inferred from electronic annotation /// 31119 // tRNA pseudouridine synthesis // inferred from electronic annotation | — | 4730 // pseudouridylate synthase activity // inferred from electronic annotation /// 16439 // tRNA-pseudouridine synthase activity // inferred from electronic annotation /// 16853 // isomerase activity // inferred from electronic annotation |
| yfeC | yfeC | Hypothetical protein yfeC /// predicted DNA-binding transcriptional regulator | — | — | — |
| basS | basS | Sensor protein basS/pmrB /// sensory histidine kinase in two-component regulatory system with BasR | 160 // two-component signal transduction system (phosphorelay) // inferred from electronic annotation /// 6468 // protein amino acid phosphorylation // inferred from electronic annotation /// 7165 // signal transduction // inferred from electronic annotation | 16020 // membrane // inferred from electronic annotation /// 16021 // integral to membrane // inferred from electronic annotation | 155 // two-component sensor activity // inferred from electronic annotation /// 4871 // signal transducer activity // inferred from electronic annotation /// 5524 // ATP binding // inferred from electronic annotation /// 16301 // kinase activity // inferr |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| hisS | hisS | histidyl-tRNA synthetase | 6412 // protein biosynthesis // inferred from electronic annotation /// 6418 // tRNA aminoacylation for protein translation // inferred from electronic annotation /// 6427 // histidyl-tRNA aminoacylation // inferred from electronic annotation | 5737 // cytoplasm // inferred from electronic annotation | 166 // nucleotide binding // inferred from electronic annotation /// 4812 // aminoacyl-tRNA ligase activity // inferred from electronic annotation /// 4821 // histidine-tRNA ligase activity // inferred from electronic annotation /// 5524 // ATP binding // |
| rpiB | rpiB | ribose-5-phosphate isomerase B | 5975 // carbohydrate metabolism // inferred from electronic annotation /// 6098 // pentose-phosphate shunt // inferred from electronic annotation | — | 5515 // protein binding // inferred from physical interaction /// 4751 // ribose-5-phosphate isomerase activity // inferred from electronic annotation /// 16853 // isomerase activity // inferred from electronic annotation |
| yhcJ | yhcJ /// nanE | Hypothetical protein yhcJ /// predicted N-acetylmannosamine-6-P epimerase | 5975 // carbohydrate metabolism // inferred from electronic annotation /// 6051 // N-acetylmannosamine metabolism // inferred from electronic annotation | — | 5515 // protein binding // inferred from physical interaction /// 16853 // isomerase |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| | | | | | activity // inferred from electronic annotation // 16857 // racemase and epimerase activity, acting on carbohydrates and derivatives // inferred from electronic annotati |
| atpB | atpB | ATP synthase subunit A /// F0F1 ATP synthase subunit A | 6810 // transport // inferred from electronic annotation /// 6811 // ion transport // inferred from electronic annotation /// 15992 // proton transport // inferred from electronic annotation | 16020 // membrane // inferred from electronic annotation /// 16021 // integral to membrane // inferred from electronic annotation /// 16469 // proton-transporting two-sector ATPase complex // inferred from electronic annotation // 45263 // proton-transpo | 15078 // hydrogen ion transporter activity // inferred from electronic annotation /// 16820 // hydrolase activity, acting on acid anhydrides, catalyzing transmembrane movement of substances // inferred from electronic annotation // 16787 // hydrolase act |
| yijF | yijF | Hypothetical protein yijF precursor /// hypothetical protein | — | — | — |
| clpX | clpX | ATP-dependent protease ATP-binding subunit | 6457 // protein folding // inferred from electronic annotation /// 15031 // protein transport // inferred from electronic annotation /// 19538 // protein metabolism // inferred from electronic annotation /// 6986 // response to unfolded protein // inferre | | 166 // nucleotide binding // inferred from electronic annotation /// 5515 // protein binding // inferred from electronic |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| aspA | aspA | Aspartate ammonia-lyase | 6531 // aspartate metabolism // inferred from electronic annotation | — | annotation // 5524 // ATP binding // inferred from electronic annotation // 8270 // zinc ion binding // inferred from electronic ann 5515 // protein binding // inferred from physical interaction // 3824 // catalytic activity // inferred from electronic annotation // 8797 // aspartate ammonia-lyase activity // inferred from electronic annotation // 16829 // lyase activity // inferred |
| yigK | yigK /// rhtB | Homoserine/homoserine lactone efflux protein /// neutral amino-acid efflux system | 6810 // transport // inferred from electronic annotation // 6865 // amino acid transport // inferred from electronic annotation | 16020 // membrane // inferred from electronic annotation // 16021 // integral to membrane // inferred from electronic annotation | 5293 // lysine permease activity // inferred from electronic annotation |
| yjhO | yjhO /// sgcX | KpLE2 phage-like element; predicted endoglucanase with Zn-dependent exopeptidase domain | — | — | 16787 // hydrolase activity // inferred from electronic annotation |
| cysD | cysD | sulfate adenylyltransferase subunit 2 | 103 // sulfate assimilation // inferred from electronic annotation /// 8152 // metabolism // inferred from electronic annotation // 8652 | — | 4781 // sulfate adenylyltransferase (ATP) activity // |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| | | | // amino acid biosynthesis // inferred from electronic annotation /// 19344 // cysteine biosynthesis // inferred from electronic annotation | | inferred from electronic annotation /// 16740 // transferase activity // inferred from electronic annotation /// 16779 // nucleotidyltransferase activity // inferred from electronic annotation |
| yjbR | yjbR | Protein yjbR /// hypothetical protein | — | — | — |
| yiiF | yiiF | hypothetical protein | | | |
| cysW | cysW | sulfate/thiosulfate transporter subunit | 6810 // transport // inferred from electronic annotation /// 8272 // sulfate transport // inferred from electronic annotation | 9276 // cell wall (sensu Proteobacteria) // inferred from electronic annotation /// 16020 // membrane // inferred from electronic annotation /// 16021 // integral to membrane // inferred from electronic annotation | 5215 // transporter activity // inferred from electronic annotation /// 15116 // sulfate transporter activity // inferred from electronic annotation /// 15563 // uptake permease activity // inferred from electronic annotation |
| 221#15 | | | | | |
| rpsG | rpsG | 30S ribosomal protein S7 | 6412 // protein biosynthesis // inferred from electronic annotation | 5622 // intracellular // inferred from electronic annotation /// 5840 // ribosome // inferred from electronic annotation /// 15935 // small ribosomal subunit // inferred from electronic annotation /// 30529 // ribonucleoprotein complex // inferred from | 49 // tRNA binding // inferred from electronic annotation /// 3723 // RNA binding // inferred from electronic annotation |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| | | | | electronic annotation | 3735 // structural constituent of ribosome // inferred from electronic annotation /// 19843 // rRNA binding // inferred from elect |
| yhfR | yhfR /// frlR | predicted DNA-binding transcriptional regulator | 6350 // transcription // inferred from electronic annotation /// 6355 // regulation of transcription, DNA-dependent // inferred from electronic annotation /// 45449 // regulation of transcription // inferred from electronic annotation | 5622 // intracellular // inferred from electronic annotation | 5515 // protein binding // inferred from physical interaction /// 3677 // DNA binding // inferred from electronic annotation /// 3700 // transcription factor activity // inferred from electronic annotation /// 30528 // transcription regulator activity // |
| fhxA | fhxA | Qin prophage; predicted protein | — | — | — |
| agaZ | agaZ /// kbaZ | Putative tagatose 6-phosphate kinase agaZ /// tagatose 6-phosphate aldolase 1, kbaZ subunit | 19402 // galactitol metabolism // inferred from electronic annotation | | 9024 // tagatose-6-phosphate kinase activity // inferred from electronic annotation /// 16301 // kinase activity // inferred from electronic annotation /// 16740 // |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| | | | | | transferase activity // inferred from electronic annotation |
| (ycfA) | tfaE | e14 prophage; predicted tail fiber assembly protein | — | — | — |
| | yhfV | Phosphotriesterase homology protein | 9056 // catabolism // inferred from electronic annotation | — | 8270 // zinc ion binding // inferred from electronic annotation /// 16788 // hydrolase activity, acting on ester bonds // inferred from electronic annotation |
| yieJ | yieJ /// cbrC | hypothetical protein | — | — | — |
| yjbQ | yjbQ | Hypothetical protein yjbQ /// hypothetical protein | — | — | — |
| ptsN | ptsN | Nitrogen regulatory IIA protein /// sugar-specific enzyme IIA component of PTS | 6810 // transport // inferred from electronic annotation /// 9401 // phosphoenolpyruvate-dependent sugar phosphotransferase system // inferred from electronic annotation | — | 5351 // sugar porter activity // inferred from electronic annotation /// 8982 // protein-N(PI)-phosphohistidine-sugar phosphotransferase activity // inferred from electronic annotation /// 16740 // transferase activity // inferred from electronic annotati |
| ygbD | ygbD | nitric oxide reductase | 6118 // electron transport // inferred from electronic annotation | — | 15036 // disulfide oxidoreductase activity // inferred from |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| | | | | | electronic annotation /// 16491 // oxidoreductase activity // inferred from electronic annotation /// 16731 // oxidoreductase activity, acting on iron-sulfur proteins as donors, NAD or NADP as ac |
| fimB | fimB | Type 1 fimbriae Regulatory protein fimB /// tyrosine recombinase/inversion of on/off regulator of fimA | 6310 // DNA recombination // inferred from electronic annotation /// 6313 // transposition, DNA-mediated // inferred from electronic annotation /// 6350 // transcription // inferred from electronic annotation /// 6355 // regulation of transcription, DNA-d | 9289 // fimbrium // inferred from electronic annotation | 3677 // DNA binding // inferred from electronic annotation |
| lasT | lasT /// yjtD | Hypothetical tRNA/rRNA methyltransferase lasT /// predicted rRNA methyltransferase | 6396 // RNA processing // inferred from electronic annotation | — | 3723 // RNA binding // inferred from electronic annotation /// 8168 // methyltransferase activity // inferred from electronic annotation /// 8173 // RNA methyltransferase activity // inferred from electronic annotation /// 16740 // transferase activity // |
| ivbL | ivbL | IlvBN operon leader peptide /// ilvB operon leader peptide | 8652 // amino acid biosynthesis // inferred from electronic annotation /// 9082 // branched chain family | — | — |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|------|---------|------|-------|-------|-------|
| gst | gst | Glutathione S-transferase /// glutathionine S-transferase | amino acid biosynthesis // inferred from electronic annotation | — | 4364 // glutathione transferase activity // inferred from electronic annotation /// 16740 // transferase activity // inferred from electronic annotation |
| phbA | phbA | hypothetical protein | — | — | — |
| phnM | phnM | PhnM protein | — | — | 16787 // hydrolase activity // inferred from electronic annotation |
| yhgI | yhgI /// gntY | Protein yhgI /// predicted gluconate transport associated protein | — | — | — |
| trmD | trmD | tRNA (guanine-N(1))-methyltransferase | 6400 // tRNA modification // inferred from electronic annotation /// 8033 // tRNA processing // inferred from electronic annotation | — | 3723 // RNA binding // inferred from electronic annotation /// 8168 // methyltransferase activity // inferred from electronic annotation /// 8175 // tRNA methyltransferase activity // inferred from electronic annotation /// 9019 // tRNA (guanine-N1-)-meth |
| grxA | grxA | Glutaredoxin 1 /// glutaredoxin 1, redox coenzyme for ribonucleotide reductase (RNR1a) | 6118 // electron transport // inferred from electronic annotation /// 6810 // transport // inferred from electronic annotation /// 9263 | — | 5515 // protein binding // inferred from |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| | | | // deoxyribonucleotide biosynthesis // inferred from electronic annotation /// 45454 // cell redox homeostasis // infer | | physical interaction /// 9055 // electron carrier activity // inferred from electronic annotation /// 15035 // protein disulfide oxidoreductase activity // inferred from electronic annotation |
| gcpE | gcpE /// ispG | 4-hydroxy-3-methylbut-2-en-1-yl diphosphate synthase /// 4-hydroxy-3-methylbut-2-en-1-yl diphosphate synthase | 8299 // isoprenoid biosynthesis // inferred from electronic annotation /// 16114 // terpenoid biosynthesis // inferred from electronic annotation | — | 5506 // iron ion binding // inferred from electronic annotation /// 16491 // oxidoreductase activity // inferred from electronic annotation /// 16728 // oxidoreductase activity, acting on CH2 groups, disulfide as acceptor // inferred from electronic annot |
| ycdB | ycdB | hypothetical protein | — | — | — |
| yfiC | yfiC | Hypothetical protein yfiC /// predicted S-adenosyl-L-methionine-dependent methyltransferase | — | — | 8168 // methyltransferase activity // inferred from electronic annotation /// 16740 // transferase activity // inferred from |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| (rcsC) | rcsC | Sensor protein rcsC /// hybrid sensory kinase in two-component regulatory system with RcsB and YojN | 160 // two-component signal transduction system (phosphorelay) // inferred from electronic annotation /// 6355 // regulation of transcription, DNA-dependent // inferred from electronic annotation /// 6468 // protein amino acid phosphorylation // inferred from electronic annotation | 16020 // membrane // inferred from electronic annotation /// 16021 // integral to membrane // inferred from electronic annotation /// 30113 // capsule (sensu Bacteria) // inferred from electronic annotation | electronic annotation /// 155 // two-component sensor activity // inferred from electronic annotation /// 156 // two-component response regulator activity // inferred from electronic annotation /// 4871 // signal transducer activity // inferred from electronic annotation /// 5524 |
| yedF | yedF | Hypothetical protein yedF /// hypothetical protein | — | — | — |
| yfjI | yfjI | CP4-57 prophage; predicted protein | — | — | — |
| yhdN | yhdN | Hypothetical protein yhdN /// hypothetical protein | — | — | — |
| phnB | phnB | PhnB protein /// hypothetical protein | — | — | — |
| (yfjV) | yfjV | CP4-57 prophage; predicted protein | 46685 // response to arsenic // inferred from electronic annotation | 16020 // membrane // inferred from electronic annotation /// 16021 // integral to membrane // inferred from electronic annotation | 15105 // arsenite transporter activity // inferred from electronic annotation |
| ydhL | ydhL | Hypothetical protein ydhL precursor | — | — | — |
| yhaN | yhaN | hypothetical protein /// hypothetical protein | — | 16020 // membrane // inferred from electronic annotation /// 16021 // integral to membrane // inferred from electronic annotation | — |
| slyA | slyA | transcriptional regulator SlyA, | 6350 // transcription // inferred from electronic annotation /// 6355 // regulation of transcription, | 5622 // intracellular // inferred from electronic annotation | 3677 // DNA binding // inferred from |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| 411#4 | yfdK | Hypothetical protein yfdK | DNA-dependent // inferred from electronic annotation // 9405 // pathogenesis // inferred from electronic annotation | — | electronic annotation // 3700 // transcription factor activity // inferred from electronic annotation |
| 633#5 | folP | Dihydropteroate synthase /// 7,8-dihydropteroate synthase | 9396 // folic acid and derivative biosynthesis // inferred from electronic annotation // 46656 // folic acid biosynthesis // inferred from electronic annotation // 46677 // response to antibiotic // inferred from electronic annotation | — | 4156 // dihydropteroate synthase activity // inferred from electronic annotation // 16740 // transferase activity // inferred from electronic annotation |
| 336#6 glvB | glvB | arbutin specific enzyme IIB component of PTS | 6810 // transport // inferred from electronic annotation // 9401 // phosphoenolpyruvate-dependent sugar phosphotransferase system // inferred from electronic annotation | 16020 // membrane // inferred from electronic annotation // 16021 // integral to membrane // inferred from electronic annotation | 5351 // sugar porter activity // inferred from electronic annotation // 8982 // protein-N(PI)-phosphohistidine-sugar phosphotransferase activity // inferred from electronic annotation // 16740 // transferase activity // inferred from electronic annotation |
| hflX | hflX | GTP-binding protein hflX /// predicted GTPase | 7264 // small GTPase mediated signal transduction // inferred from | 5622 // intracellular // inferred from electronic | 166 // nucleotide |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| | | | electronic annotation | | binding // inferred from electronic annotation /// 5525 // GTP binding // inferred from electronic annotation /// 8233 // peptidase activity // inferred from electronic annotation |
| hemX | hemX | Putative uroporphyrin-III C-methyltransferase /// predicted uropophyrinogen III methylase | 6779 // porphyrin biosynthesis // inferred from electronic annotation | 16020 // membrane // inferred from electronic annotation /// 16021 // integral to membrane // inferred from electronic annotation | 4851 // uroporphyrin-III C-methyltransferase activity // inferred from electronic annotation /// 8168 // methyltransferase activity // inferred from electronic annotation /// 16740 // transferase activity // inferred from electronic annotation |
| yceD | yceD | Hypothetical protein yceD /// hypothetical protein | — | — | — |
| ptpS | ptpS /// ygcM | Putative 6-pyruvoyl tetrahydrobiopterin synthase /// 6-pyruvoyl tetrahydrobiopterin synthase (PTPS) | 6729 // tetrahydrobiopterin biosynthesis // inferred from electronic annotation | — | 3874 // 6-pyruvoyltetra hydropterin synthase activity // inferred from electronic annotation /// 8270 // zinc ion binding // inferred from electronic |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| | | | | | annotation /// 16829 // lyase activity // inferred from electronic annotation /// 46872 // metal ion bindi |
| ibpB | ibpB | 16 kDa heat shock protein B /// heat shock chaperone | 6457 // protein folding // inferred from electronic annotation /// 6986 // response to unfolded protein // inferred from electronic annotation /// 50821 // protein stabilization // inferred from electronic annotation | — | 5515 // protein binding // inferred from physical interaction /// 51082 // unfolded protein binding // inferred from electronic annotation |
| ecnB | ecnB | Putative toxin of osmotically regulated toxin-antitoxin system associated with programmed cell death /// entericidin B membrane lipoprotein | 9636 // response to toxin // inferred from electronic annotation | 16020 // membrane // inferred from electronic annotation | — |
| aceB | aceB | malate synthase | 6097 // glyoxylate cycle // inferred from electronic annotation /// 6099 // tricarboxylic acid cycle // inferred from electronic annotation | — | 4474 // malate synthase activity // inferred from electronic annotation /// 16829 // lyase activity // inferred from electronic annotation |
| yehR | yehR | Hypothetical lipoprotein yehR precursor /// hypothetical protein | — | 16020 // membrane // inferred from electronic annotation | — |
| hsdM | hsdM | DNA methylase M | 6306 // DNA methylation // inferred from electronic annotation /// 9307 // DNA restriction-modification system // inferred from electronic annotation | — | 5515 // protein binding // inferred from physical interaction /// 3677 // DNA binding // inferred from electronic |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| | | | | | annotation /// 8168 // methyltransferase activity // inferred from electronic annotation /// 8170 // N-methyltransferase activity // inferred |
| yrbB | yrbB | Hypothetical protein yrbB /// hypothetical protein | — | — | — |
| hypC | hypC | Hydrogenase isoenzyme formation protein hypC /// protein required for maturation of hydrogenases 1 and 3 | — | — | 3676 // nucleic acid binding // inferred from electronic annotation |
| vacJ | vacJ | VacJ lipoprotein precursor /// predicted lipoprotein | — | 16020 // membrane // inferred from electronic annotation /// 19867 // outer membrane // inferred from electronic annotation | — |
| 40S#2 ydfD rpsK | ydfD rpsK | Hypothetical protein ydfD 30S ribosomal protein S11 | 6412 // protein biosynthesis // inferred from electronic annotation | 5622 // intracellular // inferred from electronic annotation /// 5840 // ribosome // inferred from electronic annotation /// 30529 // ribonucleoprotein complex // inferred from electronic annotation | 3723 // RNA binding // inferred from electronic annotation /// 3735 // structural constituent of ribosome // inferred from electronic annotation /// 19843 // rRNA binding // inferred from electronic annotation |
| yieF | yieF | Hypothetical protein yieF /// chromate reductase, Class I, flavoprotein | — | — | 16491 // oxidoreductase activity // inferred from |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| sixA | slp | Outer membrane protein slp precursor /// outer membrane lipoprotein | — | 16020 // membrane // inferred from electronic annotation /// 19867 // outer membrane // inferred from electronic annotation | electronic annotation |
| yijD | yijD | Hypothetical protein yijD /// conserved inner membrane protein | — | 16020 // membrane // inferred from electronic annotation /// 16021 // integral to membrane // inferred from electronic annotation | — |
| fliS | fliS | flagellar protein FliS | 9296 // flagellum biogenesis // inferred from electronic annotation | 9288 // flagellum (sensu Bacteria) // inferred from electronic annotation /// 19861 // flagellum // inferred from electronic annotation | — |
| hycA | hycA | Formate hydrogenlyase Regulatory protein hycA /// regulator of the transcriptional regulator FhlA | 6350 // transcription // inferred from electronic annotation /// 6355 // regulation of transcription, DNA-dependent // inferred from electronic annotation | — | 16829 // lyase activity // inferred from electronic annotation |
| wcaA | wcaA | Putative colanic acid biosynthesis glycosyl transferase wcaA /// predicted glycosyl transferase | 9103 // lipopolysaccharide biosynthesis // inferred from electronic annotation | — | 16740 // transferase activity // inferred from electronic annotation |
| yhaC 348#4 | yhaC yoeE | hypothetical protein hypothetical protein | — | — | — |
| yjhF | yjhF | KpLE2 phage-like element; predicted transporter | 6810 // transport // inferred from electronic annotation /// 15725 // gluconate transport // inferred from electronic annotation | 16020 // membrane // inferred from electronic annotation /// 16021 // integral to membrane // inferred from electronic annotation | 15128 // gluconate transporter activity // inferred from electronic annotation |
| recN | recN | DNA repair protein recN /// recombination and repair protein | 6281 // DNA repair // inferred from electronic annotation /// 6310 // DNA recombination // inferred from electronic annotation /// 6974 // response to DNA damage stimulus // inferred from electronic annotation /// 51276 // chromosome organization and biog | 5694 // chromosome // inferred from electronic annotation /// 16020 // membrane // inferred from electronic annotation | 5515 // protein binding // inferred from physical interaction /// 166 // nucleotide binding // inferred from electronic annotation /// |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| lldR | lldR | Putative L-lactate dehydrogenase operon Regulatory protein | 6350 // transcription // inferred from electronic annotation /// 6355 // regulation of transcription, DNA-dependent // inferred from electronic annotation | 5622 // intracellular // inferred from electronic annotation | 5524 // ATP binding // inferred from electronic annotation /// 3677 // DNA binding // inferred from electronic annotation /// 3700 // transcription factor activity // inferred from electronic annotation |
| yihA | yihA | GTP-binding protein | 917 // barrier septum formation // inferred from electronic annotation /// 7049 // cell cycle // inferred from electronic annotation /// 51301 // cell division // inferred from electronic annotation | 5622 // intracellular // inferred from electronic annotation | 166 // nucleotide binding // inferred from electronic annotation /// 5525 // GTP binding // inferred from electronic annotation |
| ydiL | ydiL | Hypothetical protein ydiL // hypothetical protein | — | — | — |
| tdcB | tdcB | threonine dehydratase | 6520 // amino acid metabolism // inferred from electronic annotation /// 8152 // metabolism // inferred from electronic annotation | | 3824 // catalytic activity // inferred from electronic annotation /// 4794 // threonine ammonia-lyase activity // inferred from electronic annotation /// 16829 // lyase activity // inferred from electronic annotation |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| umuD | umuD | UmuD protein /// DNA polymerase V, subunit D | 6280 // mutagenesis // inferred from electronic annotation /// 6281 // DNA repair // inferred from electronic annotation /// 6508 // proteolysis // inferred from electronic annotation /// 6974 // response to DNA damage stimulus // inferred from electronic annotation | — | 3677 // DNA binding // inferred from electronic annotation /// 4252 // serine-type endopeptidase activity // inferred from electronic annotation /// 8233 // peptidase activity // inferred from electronic annotation /// 8236 // serine-type peptidase activi |
| rplQ | rplQ | 50S ribosomal protein L17 | 6412 // protein biosynthesis // inferred from electronic annotation | 5622 // intracellular // inferred from electronic annotation /// 5840 // ribosome // inferred from electronic annotation /// 30529 // ribonucleoprotein complex // inferred from electronic annotation | 3735 // structural constituent of ribosome // inferred from electronic annotation |
| yjbI infC | yjbI infC | hypothetical protein Translation initiation factor IF-3 | 6412 // protein biosynthesis // inferred from electronic annotation /// 6413 // translational initiation // inferred from electronic annotation /// 6417 // regulation of protein biosynthesis // inferred from electronic annotation /// 6445 // regulation of | — | 3743 // translation initiation factor activity // inferred from electronic annotation /// 3723 // RNA binding // inferred from electronic annotation |
| aroF | aroF | 3-deoxy-7-phosphoheptulonate synthase /// 3-deoxy-D-arabino-heptulosonate-7-phosphate synthase, tyrosine-repressible | 8652 // amino acid biosynthesis // inferred from electronic annotation /// 9058 // biosynthesis // inferred from electronic annotation /// 9073 // aromatic amino acid family biosynthesis // inferred from | — | 3849 // 3-deoxy-7-phosphoheptulonate synthase activity // inferred from |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| | | | electronic annotation | | electronic annotation /// 16740 // transferase activity // inferred from electronic annotation /// 16829 // lyase activity // inferred from electronic annotation |
| yjiA | yjiA | Hypothetical protein yjiA /// predicted GTPase | — | — | 166 // nucleotide binding // inferred from electronic annotation /// 5525 // GTP binding // inferred from electronic annotation |
| yohL | yohL | Hypothetical protein yohL /// hypothetical protein | — | — | — |
| ftn | ftn | Ferritin 1 /// ferritin iron storage protein (cytoplasmic) | 6826 // iron ion transport // inferred from electronic annotation /// 6879 // iron ion homeostasis // inferred from electronic annotation | — | 4322 // ferroxidase activity // inferred from electronic annotation /// 5488 // binding // inferred from electronic annotation /// 5506 // iron ion binding // inferred from electronic annotation /// 8199 // ferric iron binding // inferred from electronic |
| cysM | cysM | Cysteine synthase B /// cysteine synthase B (O-acetylserine sulfhydrolase B) | 6535 // cysteine biosynthesis from serine // inferred from electronic annotation /// 8152 // metabolism | — | 3824 // catalytic activity // |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|------|---------|------|-------|-------|-------|
| | | | // inferred from electronic annotation /// 8652 // amino acid biosynthesis // inferred from electronic annotation /// 19344 // cysteine biosynthesis // | | inferred from electronic annotation /// 4124 // cysteine synthase activity // inferred from electronic annotation /// 16740 // transferase activity // inferred from electronic annotation /// 16787 // hydrolase activity // inf |
| aroK | aroK | shikimate kinase I | 8652 // amino acid biosynthesis // inferred from electronic annotation /// 9073 // aromatic amino acid family biosynthesis // inferred from electronic annotation /// 16089 // aromatic amino acid family biosynthesis, shikimate pathway // inferred from electronic annotation | — | 166 // nucleotide binding // inferred from electronic annotation /// 287 // magnesium ion binding // inferred from electronic annotation /// 4765 // shikimate kinase activity // inferred from electronic annotation /// 5524 // ATP binding // inferred from electronic annotation /// 287 // magnesium ion binding // inferred from electronic annotation /// 4634 // phosphopyruvate |
| eno | eno | phosphopyruvate hydratase | 6096 // glycolysis // inferred from electronic annotation | 15 // phosphopyruvate hydratase complex // inferred from electronic annotation | |

TABLE 3-continued

SAM ANALYSIS OF CROHN'S DISEASE (CD) VERSUS ULCERATIVE COLITIS (UC) (see FIG. 3B)

| SPOT | PROTEIN | NAME | GO BP | GO CC | GO MF |
|---|---|---|---|---|---|
| | | | | | hydratase activity // inferred from electronic annotation /// 16829 // lyase activity // inferred from electronic annotation /// 46872 // metal ion binding // |

TABLE 4

SAM ANALYSIS OF HEALTHY CONTROLS (HC) VERSUS ULCERATIVE COLITIS (UC) (see FIG. 3C)

| SPOT | PROTEIN | NAME | GO BP | GO CC | GO MF |
|---|---|---|---|---|---|
| | | | 6 Highly immunogenic proteins in UC | | |
| era | era | GTP-binding protein Era | 50875 // cellular physiological process // inferred from electronic annotation | 5622 // intracellular // inferred from electronic annotation /// 16020 // membrane // inferred from electronic annotation | 166 // nucleotide binding // inferred from electronic annotation /// 3676 // nucleic acid binding // inferred from electronic annotation /// 3723 // RNA binding // inferred from electronic annotation /// 5525 // GTP binding // inferred from electronic annotation |
| purK | purK | phosphoribosyl-aminoimidazole carboxylase | 6164 // purine nucleotide biosynthesis // inferred from electronic annotation /// 6189 // 'denovo' IMP biosynthesis // inferred from electronic annotation | 9320 // phosphoribosylamino-imidazole carboxylase complex // inferred from electronic annotation | 166 // nucleotide binding // inferred from electronic annotation /// 3824 // catalytic activity // inferred from electronic annotation /// 4638 // phosphoribosylaminoimidazole carboxylase activity // inferred from electronic annotation /// 5524 // ATP bin |
| cadA | cadA | Lysine decarboxylase, inducible /// lysine decar-boxylase 1 | 6520 // amino acid metabolism // inferred from electronic annotation | 5737 // cytoplasm // inferred from electronic annotation | 5515 // protein binding // inferred from physical interaction /// 3824 // catalytic activity // inferred from electronic annotation /// 8923 // lysine decarboxylase activity // inferred from electronic annotation /// 16829 // lyase activity // inferred from electronic annotation |
| nrfF | nrfF | Formate-dependent nitrite reductase complex nrfF subunit precursor /// heme lyase (NrfEFG) for insertion of heme into c552, subunit NrfF | — | 42597 // periplasmic space // inferred from electronic annotation | 5506 // iron ion binding // inferred from electronic annotation /// 46872 // metal ion binding // inferred from electronic annotation |
| murA | murA | UDP-N-acetylglucos-amine 1-carboxy-vinyltransferase | 7049 // cell cycle // inferred from electronic annotation /// 8360 // regulation of cell shape // inferred from electronic annotation /// 9252 // peptidoglycan biosynthesis // inferred from electronic annotation /// 19277 // UDP-N-acetylgalactosamine bios | 5618 // cell wall // inferred from electronic annotation | 8760 // UDP-N-acetylglucosamine 1-carboxyvinyltransferase activity // inferred from electronic annotation /// 16740 // transferase activity // inferred from electronic annotation |
| tpiA | tpiA | triosephosphate isomerase | 6094 // gluconeogenesis // inferred from electronic annotation /// 6096 // glycolysis // inferred from electronic annotation /// 6098 // pentose-phosphate shunt // inferred from electronic annotation /// 6633 // fatty acid biosynthesis // inferred from electronic annotation | — | 4807 // triose-phosphate isomerase activity // inferred from electronic annotation /// 16853 // isomerase activity // inferred from electronic annotation |
| | | | 27 Highly immunogenic proteins in HC | | |
| yphA | yphA | Hypothetical protein yphA /// predicted inner membrane protein | — | 16020 // membrane // inferred from electronic annotation /// 16021 // integral to membrane // inferred from electronic annotation | — |
| pssR | pssR /// yifA /// hdfR | transcriptional regulator HdfR /// transcriptional regulator HdfR | 6350 // transcription // inferred from electronic annotation /// 6355 // regulation of transcription, DNA-dependent // inferred from electronic annotation /// 45892 // negative regulation of transcription, DNA-dependent // inferred from electronic annotat | — | 3677 // DNA binding // inferred from electronic annotation /// 3700 // transcription factor activity // inferred from electronic annotation |

TABLE 4-continued

SAM ANALYSIS OF HEALTHY CONTROLS (HC) VERSUS ULCERATIVE COLITIS (UC) (see FIG. 3C)

| SPOT | PROTEIN | NAME | GO BP | GO CC | GO MF |
|---|---|---|---|---|---|
| yhdN | yhdN | Hypothetical protein yhdN /// hypothetical protein | — | — | — |
| rplO | rplO | 50S ribosomal protein L15 | 6412 // protein biosynthesis // inferred from electronic annotation | 5622 // intracellular // inferred from electronic annotation /// 5840 // ribosome // inferred from electronic annotation /// 15934 // large ribosomal subunit // inferred from electronic annotation /// 30529 // ribonucleoprotein complex // inferred from electronic annotation | 3723 // RNA binding // inferred from electronic annotation /// 3735 // structural constituent of ribosome // inferred from electronic annotation /// 19843 // rRNA binding // inferred from electronic annotation |
| 420#7 | ypeA | putative acetyltransferase | — | — | 8080 // N-acetyltransferase activity /// 8415 // acyltransferase activity /// 16740 // transferase activity /// 16747 // transferase activity, transferring groups other than amino-acyl groups |
| yehK | yehK | hypothetical protein | — | — | — |
| yihG | yihG | Hypothetical protein yihG /// predicted endonuclease | 8152 // metabolism // inferred from electronic annotation | 16020 // membrane // inferred from electronic annotation /// 16021 // integral to membrane // inferred from electronic annotation | 8415 // acyltransferase activity // inferred from electronic annotation /// 16740 // transferase activity // inferred from electronic annotation /// 4519 // endonuclease activity // inferred from electronic annotation |
| sucB | sucB | dihydrolipoamide acetyltransferase | 6099 // tricarboxylic acid cycle // inferred from electronic annotation /// 8152 // metabolism // inferred from electronic annotation | 45252 // oxoglutarate dehydrogenase complex // inferred from electronic annotation | 4149 // dihydrolipoyllysine-residue succinyltransferase activity // inferred from electronic annotation /// 5515 // protein binding // inferred from electronic annotation /// 8415 // acyltransferase activity // inferred from electronic annotation /// 1674 |
| yggH | yggH | tRNA (guanine-N(7)-)-methyl-transferase /// tRNA(m7G46)-methyltransferase | 6400 // tRNA modification // inferred from electronic annotation /// 8033 // tRNA processing // inferred from electronic annotation | — | 8168 // methyltransferase activity // inferred from electronic annotation /// 8176 // tRNA (guanine-N7-)-methyltransferase activity // inferred from electronic annotation /// 16740 // transferase activity // inferred from electronic annotation |
| rpsK | rpsK | 30S ribosomal protein S11 | 6412 // protein biosynthesis // inferred from electronic annotation | 5622 // intracellular // inferred from electronic annotation /// 5840 // ribosome // inferred from electronic annotation /// 30529 // ribonucleoprotein complex // inferred from electronic annotation | 3723 // RNA binding // inferred from electronic annotation /// 3735 // structural constituent of ribosome // inferred from electronic annotation /// 19843 // rRNA binding // inferred from electronic annotation |
| fadA | fadA | acetyl-CoA acetyltransferase | 6629 // lipid metabolism // inferred from electronic annotation /// 6631 // fatty acid metabolism // inferred from electronic annotation /// 16042 // lipid catabolism // inferred from electronic annotation | — | 3988 // acetyl-CoA C-acyltransferase activity // inferred from electronic annotation /// 8415 // acyltransferase activity // inferred from electronic annotation /// 16740 // transferase activity // inferred from electronic annotation |
| ydfO | ydfO | Hypothetical protein ydfO /// Qin prophage; predicted protein | — | — | — |
| yjhA | yjhA | Hypothetical protein yjhA | 6810 // transport // inferred from electronic | 16020 // membrane // inferred from electronic | 5351 // sugar porter activity // inferred from electronic |

TABLE 4-continued

SAM ANALYSIS OF HEALTHY CONTROLS (HC) VERSUS ULCERATIVE COLITIS (UC) (see FIG. 3C)

| SPOT | PROTEIN | NAME | GO BP | GO CC | GO MF |
|---|---|---|---|---|---|
| | | precursor /// N-acetylnuraminic acid outer membrane channel protein | annotation /// 6811 // ion transport // inferred from electronic annotation | annotation /// 16021 // integral to membrane // inferred from electronic annotation /// 19867 // outer membrane // inferred from electronic annotation | annotation /// 15288 // porin activity // inferred from electronic annotation |
| yheU | yheU | hypothetical protein | — | — | — |
| rpsL | rpsL | 30S ribosomal protein S12 | 6412 // protein biosynthesis // inferred from electronic annotation /// 46677 // response to antibiotic // inferred from electronic annotation | 5622 // intracellular // inferred from electronic annotation /// 5840 // ribosome // inferred from electronic annotation /// 15935 // small ribosomal subunit // inferred from electronic annotation /// 30529 // ribonucleo-protein complex // inferred from el | 49 // tRNA binding // inferred from electronic annotation /// 3676 // nucleic acid binding // inferred from electronic annotation /// 3723 // RNA binding // inferred from electronic annotation /// 3735 // structural constituent of ribosome // inferred fro |
| yibQ | yibQ | Hypothetical protein yibQ precursor /// predicted polysaccharide deacetylase | — | — | — |
| ycfF | ycfF /// hinT | HIT-like protein ycfF /// purine nucleoside phosphoramidase | — | — | — |
| yzgL | yzgL | hypothetical protein | — | — | — |
| yjfY | yjfY | hypothetical protein | — | — | — |
| 316#4 | rsxA | hypothetical protein | — | — | — |
| yneC | yneC | hypothetical protein | — | — | — |
| yneG | yneG | Hypothetical protein yneG /// hypothetical protein | — | — | — |
| fabH | fabH | 3-oxoacyl-(acyl carrier protein) synthase | 6633 // fatty acid biosynthesis // inferred from electronic annotation /// 8610 // lipid biosynthesis // inferred from electronic annotation | — | 3824 // catalytic activity // inferred from electronic annotation /// 4315 // 3-oxoacyl-[acyl-carrier protein] synthase activity // inferred from electronic annotation /// 8415 // acyltransferase activity // inferred from electronic annotation /// 16740 / |
| menG | menG | ribonuclease activity regulator protein RraA | — | — | — |
| sixA | slp | Outer membrane protein slp precursor /// outer membrane lipoprotein | — | 16020 // membrane // inferred from electronic annotation /// 19867 // outer membrane // inferred from electronic annotation | — |
| yhdM | yhdM /// zntR | zinc-responsive transcriptional regulator | 6350 // transcription // inferred from electronic annotation /// 6355 // regulation of transcription, DNA-dependent // inferred from electronic annotation | 5622 // intracellular // inferred from electronic annotation | 3677 // DNA binding // inferred from electronic annotation /// 3700 // transcription factor activity // inferred from electronic annotation /// 8270 // zinc ion binding // inferred from electronic annotation /// 46872 // metal ion binding // inferred from |
| ptsH | ptsH | Phosphocarrier protein HPr /// phosphohistidino-protein-hexose phosphotransferase | 6810 // transport // inferred from electronic annotation /// 9401 // phosphoenolpyruvate-dependent sugar | — | 5515 // protein binding // inferred from physical interaction /// 5351 // sugar porter activity // inferred from electronic annotation |

TABLE 4-continued

SAM ANALYSIS OF HEALTHY CONTROLS (HC) VERSUS ULCERATIVE COLITIS (UC) (see FIG. 3C)

| SPOT | PROTEIN NAME | GO BP | GO CC | GO MF |
|---|---|---|---|---|
| | | component of PTS system (Hpr) | phosphotransferase system // inferred from electronic annotation | |

As shown in the Venn diagram in FIG. 3D, the immunogenic responses to 417 proteins were found to be different between healthy control and Crohn's Disease or ulcerative colitis. Of these 417 proteins, 169 proteins were identified as highly immunogenic in healthy control, 186 proteins are highly immunogenic in Crohn's Disease and only 19 in ulcerative colitis. 44 proteins were highly immunogenic in both healthy control and inflammatory bowel disease (Crohn's Disease or ulcerative colitis). Among these 44 proteins, six overlap between healthy control and Crohn's Disease and 38 overlap between healthy control and ulcerative colitis. A full list of the immunogenic E. coli proteins in FIG. 3D can be found in Table 5.

TABLE 5

List of differentially immunogenic proteins among Healthy Control (HC), Crohn's Disease (CD) and ulcerative colitis (UC), as illustrated in FIG. 3A

| PROTEIN SPOT | HC | CD | UC |
|---|---|---|---|
| rpsK | | | |
| rpsL | | | |
| sixA | | | |
| ycfF | | | |
| yhdN | | | |
| yjhA | | | |
| era | | | |
| (yeeF) | | | |
| 211#11 | | | |
| 23-12A0 | | | |
| 279#6 | | | |
| 427#1 | | | |
| dgkA | | | |
| dinI | | | |
| emrY | | | |
| focA | | | |
| folK | | | |
| fsr | | | |
| glnD | | | |
| kch | | | |
| maoC | | | |
| msbA | | | |
| nac | | | |
| nagE | | | |
| narI | | | |
| ppx | | | |
| prtC | | | |
| rfaB | | | |
| secF | | | |
| secY/prlA | | | |
| trkG | | | |
| yafJ | | | |
| yaiM | | | |
| ybbC | | | |
| ycbM | | | |

TABLE 5-continued

List of differentially immunogenic proteins among Healthy Control (HC), Crohn's Disease (CD) and ulcerative colitis (UC), as illustrated in FIG. 3A

| | HC | CD | UC |
|---|---|---|---|
| ydaA | | | |
| ydbD | | | |
| ydhV | | | |
| yefI | | | |
| yeiO | | | |
| ygjR | | | |
| yhiN | | | |
| yjgT | | | |
| yojI | | | |
| yphD | | | |
| (yhcP) | | | |
| (yhhT) | | | |
| (yhiW) | | | |
| 16-3B0 | | | |
| 214#3 | | | |
| 233#6 | | | |
| 273#6 | | | |
| 280#1 | | | |
| 316#4 | | | |
| 321#3 | | | |
| 323#1 | | | |
| 331#2 | | | |
| 356#7 | | | |
| 406#7 | | | |
| 409#5 | | | |
| 411#1 | | | |
| 420#7 | | | |
| 452#13 | | | |
| 610#6.1 | | | |
| aceF | | | |
| allP | | | |
| ansP | | | |
| aqpZ | | | |
| atoE | | | |
| brnQ | | | |
| celD | | | |
| cobU | | | |
| codB | | | |
| cybB | | | |
| cydB | | | |
| cydC | | | |
| dgt | | | |
| dbaQ | | | |
| ebgA | | | |
| emrB | | | |
| emrD | | | |

TABLE 5-continued

List of differentially immunogenic proteins among Healthy Control (HC), Crohn's Disease (CD) and ulcerative colitis (UC), as illustrated in FIG. 3A exuR
fabH
fabZ
fadA
fepD
flhD
glnQ
glpF
gppA
greA
hemY
JW0438
JW1949
lipA
lpxC
malX

malZ
menG
mrdB
murG
mutT
narU
nfrB
nrfE
ompC
oppC
oppF
pbuX
pheP

phsE
pnuC
potC
pssR
ptsH
putP
queA
rfaL
rffG
rocE
rblO
sdhD
secB
sfsA
slyX
sucB

sucD
tauB
thiL
trkH
udk
uidB
virK
yaaH
yabK
yadQ
yaeG
yagG
yagM

TABLE 5-continued

List of differentially immunogenic proteins among Healthy Control (HC), Crohn's Disease (CD) and ulcerative colitis (UC), as illustrated in FIG. 3A yaiV
yajR
ybaN
ybdS
ybfB
ybfC
ybgE
ybhA
ybhL
ybhM
ybhN
ybhR
ycaD
yccY

ycdG
yciQ
yciR
yciS
ydcD
yddH
ydeF
ydeZ
ydfO
ydjS
ydjZ
yeaS
yehK
yehY

yejF
yfjY
ygeD
ygtF
yggH
yghK
yghT
ygjQ
yhaH
yhaO
yhbX
yhcO
yhdM
yhdT
yheG

yheU
yhfU
yhhL
yhhS
yhiP
yhiQ
yhjX
yiaL
yiaQ
yibL
yibQ
yicO
yidY
yifE

TABLE 5-continued

List of differentially immunogenic proteins among Healthy Control (HC), Crohn's Disease (CD) and ulcerative colitis (UC), as illustrated in FIG. 3A yigF
yihG
yjeM
yjfF
yjfP
yjfY
yjhB
ymdD
ynaJ
yneC
yneG
ynjC
yoaA yohG
yphA
yphG
yqcE
yzgL
(gntU)
(phnE)
(rcsC)
(thiS)
(ycfA)
(yfjV)
221#15
267#6
304#1
319#17
336#6

348#4
405#2
411#4
416#1
430#8
445#15
448#2
633#5
aceB
agaZ
aidA
argB
argC
aroF aroK
aspA
atpB
baiF
basS
cedA
citB
citG
clpX
cysD
cysJ
cysM
cysW
dgxA
dicC

TABLE 5-continued

List of differentially immunogenic proteins among Healthy Control (HC), Crohn's Disease (CD) and ulcerative colitis (UC), as illustrated in FIG. 3A dinD
ecnB
eno
fadB
fba
fdhE
fecB
fecR
fimB
fimC
fliA
fliS
flxA
folP
frvX ftn
fumb
gabD
galR
gcpE
glvB
grxA
grxC
gst
hemX
hflX
hisS
hofH hoxK
hsdM
hycA
hycF
hypC
ibpB
infC
ivbL
lasT
LDR-ABC
LDR-D
lldR
mcrD
metB
metJ mltB
mviN
narY
nuoE
phbA
phnB
phnG
phnM
ppdB
ptpS
ptsN
purM
radC
rbfA

TABLE 5-continued

List of differentially immunogenic proteins among Healthy Control (HC), Crohn's Disease (CD) and ulcerative colitis (UC), as illustrated in FIG. 3A rbsB
recN
rffD
rpiB
rplP
rplQ
rplT
rpmJ
rpsG
rpsR
selD
slyA
slyD
ssi6 sugE
tdcB
thiF
torA
trmD
ubiG
umuD
vacJ
wcaA
ybbA
ybbQ
ycbF
ycdB
yceD ycgN
ydfA
ydfD
ydfR
ydhL
ydiL
yedF
yehR
yejG
yejO
yfeC
yfhD
yfiC
yfiD yfjI
yfjQ
ygbA
ygbD
ygbO
ygcQ
ygeW
ygfY
yhaA
yhaC
yhaN
yhcI
yhcJ
yhfR
yhfV yhgH
yhgI
yicC
yieF
yieJ
yigK
yihA
yihD
yihK
yiiF
yijD
yijF
yjaI yjbI
yjbL
yjbQ
yjbR
yjcS
yjeB
yjeJ
yjgF
yjhC
yjhE
yjhF
yjhO
yjiA
yliG
ymfE yohL
yphC
yrbB
(rtn)
cadA
lueO
mesJ
mhpF
modC
murA
nrfF
prpE
purK
tpiA
yciD yejA
ygcE
ygfQ
yhjC
yifH
yjiJ Legend
■ Highly immunogenic This demonstrates that ulcerative colitis and healthy control subjects share more common immunogenic profiles than Crohn's Disease and healthy control. In general, these results indicate that much of the global immunogenic profiles of sera samples were systematically correlated with either healthy controls or IBD phenotypes and that sample class can be distinguished based on the sample's immunogenic profile.

Example 3

Protein Functional Enrichment Analysis

Figure 4:
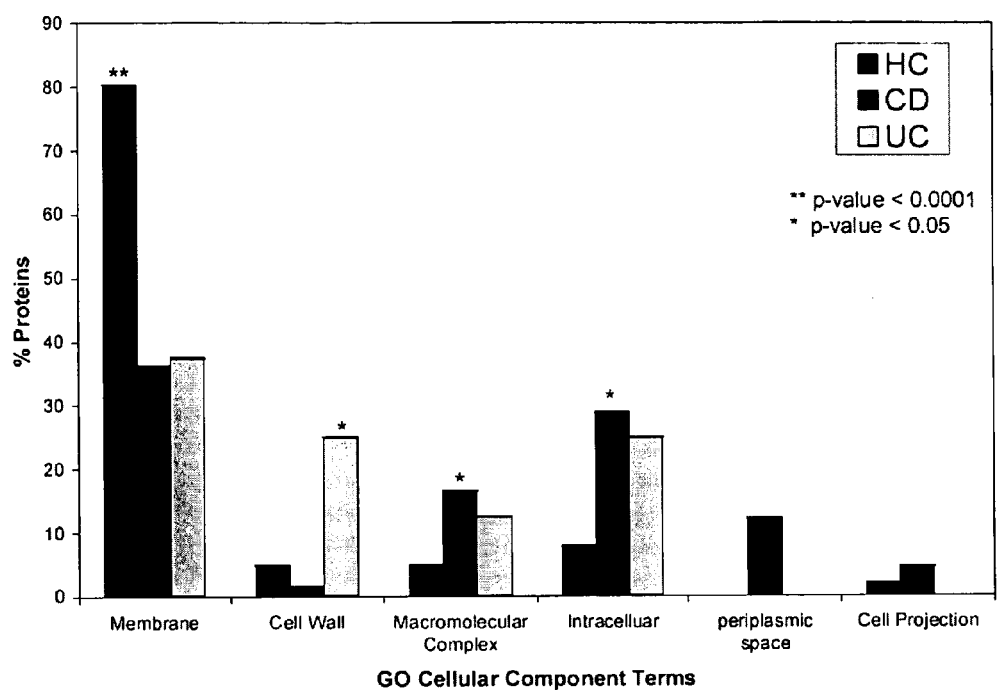
FIG. 4 is a graph showing the distribution of the cellular component terms in the highly immunogenic response proteins of healthy controls (HC), CD and ulcerative colitis. Six Cellular Component terms from the Gene Ontology were examined. Cell projection term contains flagellum and fimbrium proteins. The main messages include: 1) approximately 80% of the highly immunogenic proteins are either membrane proteins in healthy control (p<0.0001), compared to only ~37% of the top immunogenic proteins in Crohn's Disease patients (not statistically significant); 2) conversely, ~30% of top immunogenic proteins in Crohn's Disease patients are intracellular proteins (p<0.05) compared to only ~7% in healthy control (not statistically significant); 3) a significant higher percentage of cell wall proteins (~26%) are immunogenic in ulcerative colitis (p<0.05) compared to those in healthy control and Crohn's Disease (not significant); and 4) a significant percentage of macromolecular complex proteins (~16%; p<0.05) in Crohn's Disease compared to those in healthy control or ulcerative colitis (not statistically significant). No statistically significant enrichment of proteins of periplasmic space and cell projection were found in healthy control, Crohn's Disease and ulcerative colitis.

To delineate the immunogenic signatures of the healthy controls and IBD subtypes the differentially immunogenic proteins were assigned to functional groups based on classification by Gene Ontology. Functional grouping of the 417 proteins were assigned by querying EcoCyc and KEGG databases, as well as cross-checked with Affymetrix *E. coli* Genome Array annotation file. 338 of these 417 proteins were assigned to at least one gene ontology (GO) term, and 78 hypothetical proteins have unknown annotations. The enrichment analysis was focussed on five GO cellular component terms (membrane, cell wall, intracellular, macromolecular complex, periplasmic space and cell projection). To assess whether the selected differentially immunogenic proteins were enriched in one of the GO terms, the hypergeometric statistical test was used to compute the probability of the number of proteins in each cellular component appearing by chance within the proteins highly immunogenic in healthy control (169), Crohn's Disease (185) and ulcerative colitis (18). FIG. 4 summarizes the enrichment analysis of these proteins that are immunogenic in healthy control and Crohn's Disease or ulcerative colitis. Antibodies against membrane proteins are highly enriched in healthy control samples ($p<0.0001$). Interestingly, antibodies against intracelluar and macromolecular complex proteins are highly enriched in Crohn's Disease samples ($p<0.05$), while those against cell wall proteins are highly enriched in ulcerative colitis samples ($p<0.05$). Although 12% proteins that were found to be highly immunogenic in Crohn's Disease samples were located in periplasmic space, their enrichment was not statistically significant ($p=0.064$) for this IBD subtype. Proteins located in cell projection term are not enriched in either healthy controls or IBD subtypes.

Example 4

Machine Learning Analysis

Figure 5D:
FIG. 5D shows representative protein spots that were differentially recognized by sera from Crohn's Disease vs ulcerative colitis, respectively. This figure shows the relative immunogenic reactivity (fluorescent signals) of frvX and yidX by serum antibodies from a CD and ulcerative colitis patient.
Figure 5D:
Figure 5D:
Figure 5D:

Next, optimal classifiers were constructed from the immunogenic response profiles to differentiate healthy control from the IBD subtypes (Crohn's Disease and ulcerative colitis), as well as to differentiate Crohn's Disease from ulcerative colitis. Upon successful construction of these classifiers, the classification rules may result in the discovery of new robust biomarkers. k-TSP, a novel machine learning method was employed to discover simple decision rules classifiers from the immunogenic response profiles. The three top scoring pairs were identified as classifiers to differentiate healthy control samples from Crohn's Disease samples as follows:

1. If a subject sample shows greater immunogenic reactivity to era than to ybaN then the subject is identified as likely having Crohn's Disease, or else as UC.
2. If a subject sample shows greater immunogenic reactivity to yhgN than to focA then the subject is identified as likely having Crohn's Disease or as a healthy control; and
3. If a subject sample shows greater immunogenic reactivity to gabT than ycdG then the subject is identified as likely having Crohn's Disease (see representative examples of actual images of immuno-reactive protein spots in FIG. 2). If all three pairs identify the subject as having Crohn's disease then the sample is classified as a Crohn's Disease sample. FIG. 5A depicts the protein spot ratios for this classifier that separate the data between the two phenotypes where yellow represents a vote for Crohn's Disease and blue represents a vote for healthy control. Using the k-TSP classifier, 36 out of 39 healthy control and 62 out of 64 Crohn's Disease samples are correctly classified, with an estimated ten-fold cross-validation accuracy of 86±4% ($p<0.01$). For distinguishing healthy control from ulcerative colitis samples, the k-TSP algorithm identifies eleven feature pairs (FIG. 5B) with an estimated ten-fold crossvalidation accuracy of 66±5% ($p<0.04$). A single feature pair of k-TSP classifier was identified for differentiating Chrohn's disease from ulcerative colitis: If the sample has greater immunogenic reactivity to frvX than to yidX then the subject is identified as having ulcerative colitis as illustrated in FIG. 5C (see representative examples of actual images of immuno-reactive protein spots in FIG. 5D). This classifier has an estimated ten-fold cross-validation accuracy of 80±2% ($p<0.1$).

The performance of k-TSP was also compared with SVM and kNN, two other commonly used learning algorithms, for each of the classification problems based on five runs of ten-fold crossvalidation. Table 6 displays the results of ten-fold cross-validation for each of the three classifiers.

TABLE 6

Estimated ten-fold cross-validation classification rates of IBD using the three described classification methods.

| Healthy control (HC) (39) vs CD (66) | | | | | |
|---|---|---|---|---|---|
| Method | Accuracy (%) | Sp (HC) (%) | Sn (CD) (%) | PPV (CD) (%) | NPV (HC) (%) |
| k-TSP | 86 ± 4 | 81 ± 5 | 89 ± 3 | 89 | 81 |
| SVM | 70 ± 2 | 66 ± 1 | 73 ± 2 | 79 | 59 |
| kNN | 63 ± 3 | 47 ± 7 | 73 ± 6 | 70 | 50 |

| Healthy control (HC) (39) vs UC (29) | | | | | |
|---|---|---|---|---|---|
| Method | Accuracy (%) | Sp (HC) (%) | Sn (UC) (%) | PPV (UC) (%) | NPV (HC) (%) |
| k-TSP | 66 ± 5 | 69 ± 5 | 61 ± 7 | 59 | 70 |
| SVM | 62 ± 5 | 58 ± 1 | 68 ± 12 | 55 | 71 |
| kNN | 60 ± 6 | 57 ± 2 | 64 ± 12 | 53 | 68 |

| CD (66) vs UC (29) | | | | | |
|---|---|---|---|---|---|
| Method | Accuracy (%) | Sp (CD) (%) | Sn (UC) (%) | PPV (CD) (%) | PPV (UC) (%) |
| k-TSP | 80 ± 2 | 84 ± 1 | 70 ± 6 | 86 | 66 |
| SVM | 78 ± 3 | 82 ± 2 | 69 ± 9 | 86 | 63 |
| kNN | 78 ± 3 | 78 ± 4 | 61 ± 2 | 82 | 55 |

The reported rates are given in percentages and are the mean performance on all five runs of ten-fold cross validation ± the standard deviation. In parenthesis are the numbers of samples in each subtype used for classification. Sp = specificity, Sn = sensitivity, PPV = positive predictive value, NPV = negative predictive value.

Figure 6:
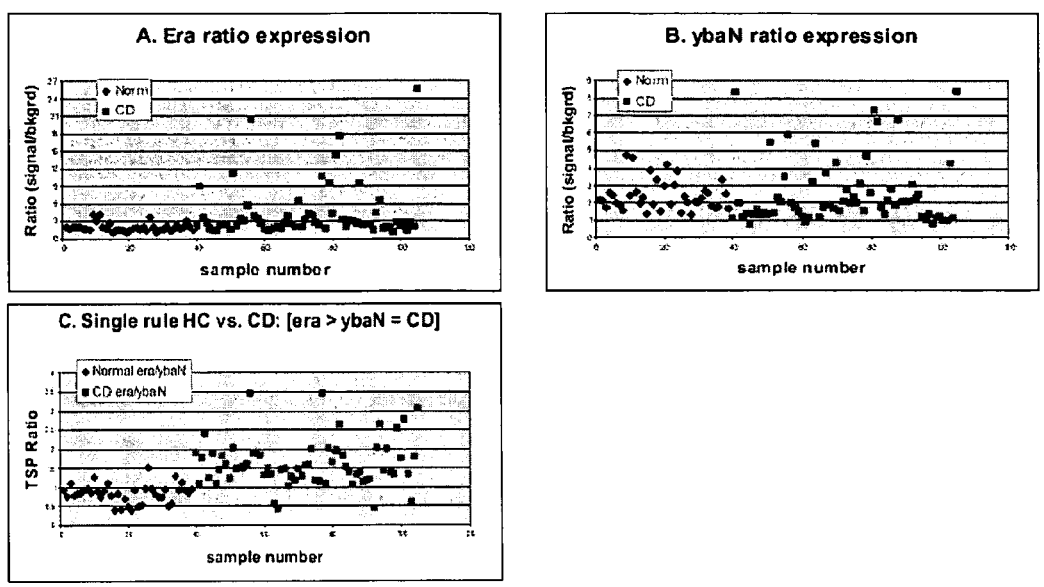
FIGS. 6A-6C are scatter plots showing the immunogenic reactivity (signal) of the samples to era and ybaN individually (FIGS. 6A & B, respectively) and the TSP ratio (era/ybaN)

As demonstrated in Table 6, based on cross-validation, k-TSP performance meets or exceeds the performance of kNN and SVM for these classification problems. Because the cross-validation structure allowed each classifier to test the same subsets of data as described in the methods section, the performance of the three classifiers can be directly compared and tested for statistical significance by a simple student's t-test. The healthy control vs. CD k-TSP classifier outperformed the other methods in total classification performance ($p<0.001$). For the remaining two classification problems, the k-TSP classifiers achieved nominally better, but not statistically significant in classification accuracy when compared to SVM and kNN classifiers. From this study, k-TSP was found to perform much better than SVM and kNN in separating healthy control from Crohn's Disease. In addition, the ordering of the expression values within profiles were utilized in the k-TSP decision rules, therefore, the classifier is invariant to data pre-processing (28). FIGS. 6A and 6B show that on their own, the immunogenic responses to era and ybaN (the top scoring pair in the healthy control vs CD k-TSP classifier) do not allow for class separation of the data; no threshold level would clearly separate healthy control from Crohn's Disease. However, the ratio of the two features (top-scoring pair ratio) results in clear separation in the data lending well to classification (FIG. 6C). Similar results are true when scatter plot analysis was done for the other two TSP pairs from the healthy control vs Crohn's Disease classifier (yhgN vs focA and gabT vs ycdG, respectively). This represents an advantage of k-TSP over other learning methods where interpreting the decision rules are easy and can facilitate follow-up study. It is important to note that SAM identified era as the second best individual marker for up regulation in CD, thus it appears that individual markers will not work well for classification and explains why KNN and SVM fail to match the performance of k-TSP as the relative feature levels within samples appear to be much more robust then the absolute feature levels across samples Example 5

Robustness of the k-TSP Classifiers

To determine that class imbalance did not greatly affect the classification results, an additional analysis was performed where samples were randomly discarded from a class with greater total number of samples in order to equalize the class sizes. 10-fold cross validation was performed as described. The process was then repeated by discarding a different random set of samples.

Table 7 (below) shows the performance of each classifier given class balance in the training set.

in each class. 10-fold cross validation is carried out to yield a classification rate for the permutation set. 100 permutations were performed in order to get a null distribution of expected classification rates by chance. The classification rate from the un-permuted data is then compared to the null distribution to determine significance. Table 7 shows the permutation test results for all the classification problems. For the k-TSP classifiers trained to differentiate between healthy control and Crohn's Disease samples as well as Crohn's Disease and ulcerative colitis samples, no permuted set achieved classification rates equal or superior to the original data out of 100 permutations. Thus, these classifiers were estimated to be significant at the $p<0.01$ level. The k-TSP classifier built to differentiate healthy control and ulcerative colitis had 4/100 permutations achieve rates that matched or exceeded the original classifier, thus this classifier is near the typical significance threshold at $p<0.05$.

Finally, to gauge the robustness of the classification rules discovered by the k-TSP method, the surrogate classifiers created during the ten-fold cross validation procedure were inspected. Every loop of cross validation creates a separate classifier used to predict the left out sample classes, these are called surrogate classifiers. Thus, for each problem of interest that was performed ten fold cross-validation in Table 7, there were 50 classifiers to inspect (10 for each of the 5 runs). The percentage of the time that the rule from the final k-TSP classifier showed up in the 50 surrogate classifiers was an indicator of the robustness of that rule. Table 7 shows that the pairs that show up in the healthy control vs. Crohn's Disease classifier as well as the ulcerative colitis vs. Crohn's Disease classifier are fairly robust while the pairs in the

TABLE 7

Permutation statistics for each pair of biomarkers.

| k-TSP Classifier | 10-fold CV | 10-fold CV Permutation | Estimated p-value | Features in k-TSP classifier | % feature appearance |
|---|---|---|---|---|---|
| HC vs. CD | 86 ± 3 | 50 ± 8 | p < 0.01 | era > ybaN = CD | 90 |
| | | | | yhgN > focA = CD | 84 |
| | | | | gabT > ycdG = CD | 64 |
| HC vs. UC | 66 ± 5 | 51 ± 9 | p < 0.05 | relE > cysE/wcaB = UC | 80 |
| | | | | pyrI > yjgK = UC | 42 |
| | | | | Int > ybiO = UC | 36 |
| | | | | ftsE > pssR = UC | 36 |
| | | | | yhgN > yhfG = UC | 20 |
| | | | | yafN > dsbB = UC | 20 |
| | | | | yihI > yabK = UC | 26 |
| | | | | 421#15 > yhdN = UC | 24 |
| | | | | hisP > rplO = UC | 16 |
| | | | | cml > nuoM = UC | 14 |
| | | | | yieC > nuoI = UC | 12 |
| UC vs. CD | 80 ± 2 | 52 ± 6 | p < 0.01 | yidX > frvX = UC | 88 |

Top scoring pairs used for each classifier and the percentage of surrogate classifiers in which those pairs appear during 10-fold cross validation (mean ± standard deviation, p-value).

These results demonstrate that k-TSP outperforms SVM and kNN in most instances whether or not the class size is balanced, further supporting the data presented in Table 5.

Next, to determine the significance of each classifier, a permutation test was performed by randomly shuffling the class labels while maintaining the same number of samples healthy control vs. ulcerative colitis classifier are not. Along with the permutation testing, this indicates that the healthy control vs. Crohn's Disease and ulcerative colitis vs. Crohn's Disease classifier should perform well in independent testing while the healthy control vs. ulcerative colitis classifier may not.

Example 6

Stratifying Crohn's Disease Subtypes and Risk for Surgery

Certain antibody-based serological biomarkers (such as pANCA and ASCA) have shown promise in risk stratifying patients prior to instituting medical therapy or embarking on surgery. As an example, the presence of pANCA has been associated with the development of acute and chronic pouchitis after colectomy with ileal pouchanal anastamosis. Similarly, the presence of high titers of ASCA has been found to predict the occurrence of pouch complications and a more complicated disease course in Crohn's disease. To evaluate whether the new biomarkers identified can be used to stratify Crohn's Disease and ulcerative colitis subtypes or risk for surgery, the Vienna classification was used to subtype patients with Crohn's Disease into the following behavior subtypes (Table 1): penetrating/fistulizing, stricturing, penetrating/structuring and non-penetrating non-stricturing. Patients with ulcerative colitis were divided into those with left sided disease (inflammation extending no further than the splenic flexure). Pancolitis was considered to be continuous inflammation from the rectum extending beyond the splenic flexure. Due to the small sample sizes for each disease type, k-TSP analysis using the newly identified biomarkers was unable to stratify subtypes of Crohn's Disease or ulcerative colitis, or risk for surgery. When larger sample sizes are available, it is expected that at least those biomarkers listed herein will be useful for identifying subjects in need of surgery. In particular, pairs and sets of biomarkers delineated in Tables 2-5, 7, and FIG. 5 are useful alone or in combination with existing biomarkers to identify subjects that could benefit from surgery.

Example 7

OmpC and fliC, Two of the Known Serological Markers, Performed Poorly

Figure 7:
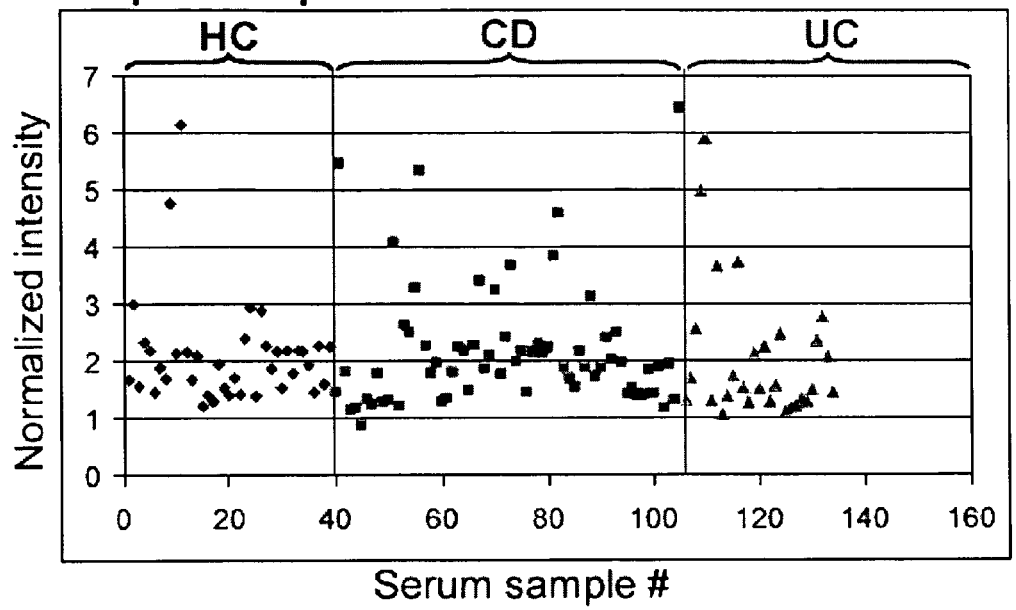
FIG. 7 scatter plots of immunoreactivity of OmpC and fliC, respectively, which were carried out as described in FIG. 6C. The present study found that OmpC and fliC (Cbir), two of the known serological markers, performed poorly in the present study. The scatter plots display the normalized immunogenic signal to each protein for every serum sample. The samples are separated along the x-axis according to class (healthy control, CD, and ulcerative colitis). Both statistical analysis and visual inspection demonstrate that antibodies against neither protein are capable of discriminating among the classes.
Figure 7:
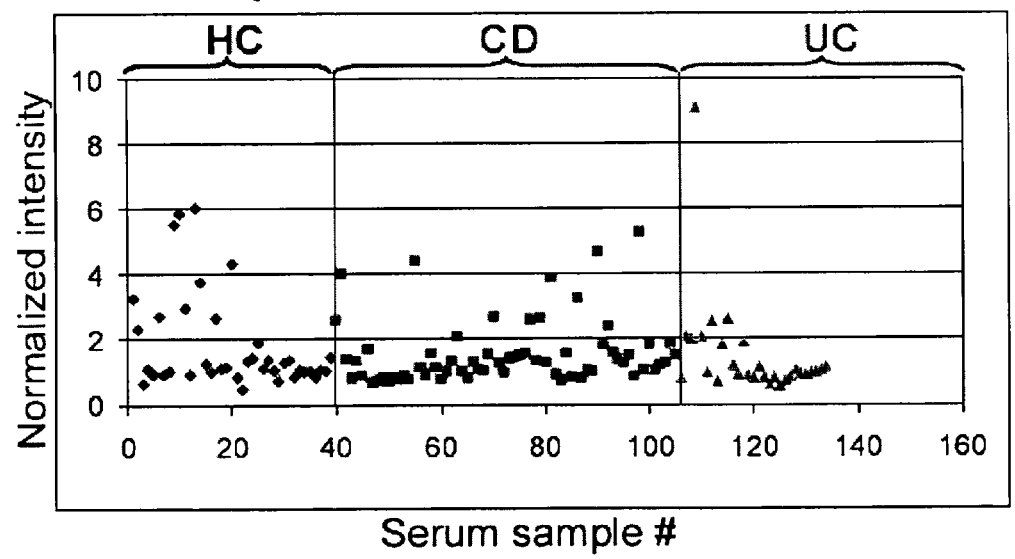

Although anti-OmpC and anti-Cbir (fliC) have been recently considered two new IBD serological biomarkers, these markers were not identified in our screening of the *E. coli* K12 proteome. Scatter plot (FIG. 7) analysis of *E. coli* ompC and fliC demonstrates that neither allows for class separation between control vs Crohn's Disease vs ulcerative colitis; no threshold level would clearly separate the data.

Protein microarrays have been demonstrated to be a powerful tool to identify biomarkers. The results reported herein provide the first study to identify serological biomarkers in human autoimmune diseases using a protein chip of whole prokaryotic proteome. The significance of this study is three-fold: First, it presents here the first proof of principle for the feasibility of application of high density protein microarray/chip technology in the discovery of novel serological IBD biomarkers. This study can serve as an example of similar proteomic approaches for hunting serological biomarkers for other immune-related diseases, such as autoimmune disorders. Second, this is the first examination of human immune responses to the entire proteome of a microbial species under normal or any disease condition. It is surprising to learn that human circulating antibodies can recognize more than 400 *E. coli* proteins (FIG. 3D). Since it has been demonstrated that defective intestinal barrier function plays a central role in the pathogenesis of Crohn's Disease, it is conceivable that in patients with Crohn's Disease commensal bacteria or their products could more readily penetrate intestinal epithelia. Therefore, it is less surprising that 185 of the *E. coli* proteins were recognized by sera from Crohn's Disease patients (FIG. 3D). However, it remains a mystery why there are a large number (185) of immunogenic *E coli* proteins that are specific in healthy controls while only 18 immunogenic proteins are found to be specific to ulcerative colitis. Third, this study identified a set of novel serological biomarkers that have >80% overall accuracy and sensitivity in differentiating CD from healthy control or ulcerative colitis.

An intriguing observation in this study is the difference in the immunogenicity of surface/membrane vs intracellular proteins in healthy control vs CD patients. Approximately 85% of the highly immunogenic proteins were either cell wall proteins or membrane proteins in healthy control, compared to only ~37% of the top immunogenic proteins in Crohn's Disease patients (FIG. 4, FIG. 5 and Tables 2-5, and 7). Conversely, ~30% of top immunogenic proteins in Crohn's Disease patients are intracellular proteins compared to only ~7% in healthy control (FIG. 4, FIG. 5 and Tables 2-5, and 7). Furthermore, there is no overlap among the top immunogenic *E. coli* surface/membrane proteins among the three distinct populations (healthy control, Crohn's Disease and ulcerative colitis, see FIG. 3D). This suggests that the host immunological response to *E. coli* is drastically different between healthy control and CD patients. The mechanism of having these immunogenic differences is not clear at this moment. It is likely that in immunologically healthy hosts where *E. coli* are largely confined to the luminal side of the gut due to intestinal epithelial barrier, surface and membrane proteins of *E. coli* might be the primary antigens that are more accessible to the immune system, compared to intracellular proteins. In this case, immune system has adapted to the presence of luminal *E. coli*. In contrast, in Crohn's Disease patients, a disrupted or compromised intestinal barrier may lead to the bacterium or its products crossing the gut luminal barrier. If the whole *E. coli* invades into the lamina propria, it will mostly likely be lysed by host immune system. Subsequently, *E. coli* components such as intracellular proteins that wpi; d otherwise not be seen by the intestinal immune system in the lamina propria are presented by antigen-presenting cells (such as macrophages or dendritic cells).

This may dramatically alter the previously adapted immune system that is only used to the luminally exposed *E. coli*, resulting in an overwhelming production of antibodies against these intracellular *E. coli* proteins. The consequences of these immune responses include recruitment of various inflammatory immune cells such as neutrophils, dendritic cells, and lymphocytes to lamina propria or between colonic epithelial cells, leading to dysregulated mucosal inflammation. This may also explain why there are only 6 overlapping proteins among 354 top immunogenic proteins recognized by healthy control and Crohn's Disease patients (FIG. 3D).

None of the serum antibody biomarkers that are identified here for discriminating Crohn's Disease from healthy control or ulcerative colitis have been previously described. Although most of the antigens (*E. coli* proteins) responsible for generation of these marker antibodies have not been well characterized, their identity and function can be predicted based on their sequence information. Among the proteins in the k-TSP classifier—era, ybaN, yhgN, focA, gabT and ycdG (FIG. 5A)—for discriminating CD from healthy control, era is a GTP binding protein that involves in the binding of GTP and nucleotide of cell cycle and can be found in intracellular membrane. In this study, an increased immunogenic response to era is associated with Crohn's Disease, identified by both SAM and k-TSP analyses. YbaN is predicted as a conserved inner membrane protein with unknown function. YhgN is predicted as an inner six transmembrane domains protein where the C-terminus is located in the periplasm (36). YcdG (also called rutG) is another predicted transmembrane with eleven helices; the C-terminus of the protein is located on the cytoplasmic side of the inner membrane (36). This protein is predicted to be involved in the pyrimidine utilization in E. coli where it may function as a proton-driven uracil uptake system (37). FocA, an inner membrane protein, is a putative formate transporter that may involve in both formate uptake and efflux. Disruption of the focA gene confers resistance to hypophosphite, a toxic formate analogue (38). GabT, 4-aminobutyrate aminotransferase, is a well characterized protein and acts as the initial enzyme of the 4-aminobutyrate (GABA) degradation pathway in E. coli (39). Among the pair of proteins (frvX and yidX) that were identified to be discriminatory between CD and ulcerative colitis, frvX is a important protein in fructose-specific PEP-dependent sugar phosphotransferase system (40); and yidX is a predicted lipoprotein, the function of which is currently unknown.

Like all previously identified serological (antibody) biomarkers, including p-ANCA, ASCA, anti-OmpC, and anti-I2 and anti-Cbir, the pathological or functional consequences of having these newly identified circulating antibodies is unclear.

The newly identified biomarkers by k-TSP analysis have a particular impressive ~86% accuracy in differentiating CD from healthy control, with a specificity of ~81% and a sensitivity of ~89% (Table 6). In addition, k-TSP analysis yields an accuracy of ~80% in differentiating CD and ulcerative colitis, with a sensitivity of ~84% and specificity of ~70% (Table 6). These demonstrate that the sensitivity and specificity of these novel serological markers are comparable to those of combination of the multiple best-characterized IBD biomarkers (ASCA, pANCA, anti-OmpC, and anti-Cbir) (41, 42). More importantly, an identical performance can be achieved by using only the top 3 pairs of E. coli proteins for discriminating healthy controls vs CD, and one top pair of proteins for differentiating CD vs ulcerative colitis (FIGS. 2 & 5 and Tables 2 &3).

These data provide a critical feasibility for 1) validation study using additional larger cohorts of IBD patients and controls and 2) future development of novel assay kits for diagnosis of CD and ulcerative colitis. However, it is necessary to point out that our current approach screening E. coli protein array is not suitable for identifying serological biomarkers in differentiating ulcerative colitis from healthy control (only ~66% accuracy) (Tables 5 and 6). Importantly, OmpC, an E. coli antigen for one of the widely studied current serological biomarker (anti-OmpC), was not picked up in our screen (FIG. 7A). Similarly, fliC, an E. coli flagellin protein equivalent the Salmonella flagellin (which is the antigen for anti-Cbir, another widely studied antibacterial antibody) did not show up in our analysis (FIG. 7A). These data would suggest that anti-OmpC and at least the antibody against E. coli fliC are not robust serological biomarkers for IBD. In conclusion, we have presented here the first demonstration that using protein array to screen circulating disease-specific antibodies is a robust, effective and high throughput approach for discovery of novel biomarkers of IBD. This approach can be readily applied to screen serological biomarkers of various autoimmune diseases and/or even infectious diseases.

The results reported above were obtained using the following methods and materials.

Patients and Serum Acquisition

Serum was obtained from 134 subjects in accordance with the policy of the Johns Hopkins Hospital Institutional Review Board. Sixty six patients had the diagnosis of Crohn's disease (CD), 29 patients were diagnosed with ulcerative colitis (UC), and 39 subjects were non-IBD healthy controls (HC). The healthy controls and IBD patients were similar in age and sex distribution. The demographic and clinical characteristics of the patients are summarized in Table 1. Clinical information was abstracted from the written and electronic medical records. The diagnosis of CD and ulcerative colitis was established by standard clinical, radiographic, endoscopic and histological criteria. Patients were classified as having CD based on the typical findings of skip lesions, deep linear or serpiginous ulcerations, cobblestoning, multiple noncaseating granulomas, transmural inflammation, small bowel involvement, structuring disease or presence of fistulilizing disease. The diagnosis of ulcerative colitis was considered if the colonic inflammation involved the rectum with or without proximal extension. The inflammation had to be continuous and be limited to the mucosa. There were no patients with proctitis enrolled in this study. The healthy controls consisted of individual undergone colon cancer screening or other non-IBD GI diseases or any other immune diseases. The serum samples were obtained at the time of initial outpatient encounter, at the time of an endoscopy or during hospitalization. The blood was collected into a serum separator tube (Red top tube, BD Vacutainer) and spun down within 60 minutes of collection. Serum was removed, aliquoted, and stored in multiple at −80° C. until assayed.

Fabrication of E. coli Proteome Chips.

To facilitate the analysis of protein function in the bacterial proteomes, we have constructed a protein chip that essentially covers the entire proteome of the E. coli K 12 strain (Chen (2008) Nat. Methods 5, 69-74). Briefly, 4,256 E. coli proteins were first purified using an ORF collection kindly provided by Dr. Mori and colleagues (26). E. coli cells first were grown overnight at 37 C in 2×LB media containing 30 µg/ml chloramphenicol in a 96-well format and allowed to grow for overnight. The overnight cultures were diluted to a final OD600 of ~0.1. After the cells were grown for ~3 hrs at 37 C, and protein expression were induced with 1 mM isopropyl β-thiogalactoside (IPTG) for ~3.5 hrs. The liquid cultures were then harvested by centrifuge of 3500 rpm for 5 min at 4° C. The pellets were stored at −80° C. for future protein purification.

To purify the fusion proteins, the frozen cell pellets were re-suspended in phosphate lysis buffer, containing 300 mM NaCl, 20 mM imidazole, CelLytic B, Lysozyme (1 mg/mL), Benzonase (50 units/ml), proteinase inhibitor cocktail, and PMSF (1 mM). Along with Ni-NTA beads, the mixtures were incubated for 1.5 h at 4° C. After mixing, the resin-protein complexes were washed 3 times with Wash buffer I (50 mM NaH2PO4 with 300 mM NaCl, 10% glycerol, 20 mM imidazole, 0.01% Triton X-100, at pH 8) and 3 times with Wash buffer II (50 mM NaH2PO4 with 150 mM NaCl, 25% glycerol, 20 mM imidazole, 0.01% Triton X-100, at pH 8). Finally, the fusion protein was eluted with elution buffer (50 mM NaH2PO4/150 mM NaC1/25% glycerol/250 mM imidazole/0.01% Triton X-100, pH 7.5). All purified proteins were printed in duplicate onto FullMoon slides using a ChipWriter Pro (Bio-Rad) in a humidity-controlled chamber in a cold room (25).

Screen of E. coli Proteome Chip for Anti-E. coli Antibodies.

The entire screening process, except for the washing steps as specified, was done at room temperature. E. coli protein chips stored at −80 C were thawed at room temperature (22 C) and blocked in Superblock Blocking Buffer (Pierce) for one hour. The patient's serum was diluted (1:1000) with blocking buffer in a total volume of 3 ml. The diluted serum was then applied to the chip entirely covering the surface. After 1 hour incubation with gentle shaking on a rocker, the chip was rinsed once with 4 ml of Tris-buffered saline (TBS) with 0.05% Tween 20 (TBS-T). The chip was then soaked in 4 ml TBS-T, placed in a water bath and washed for 10 min at 50 C with gentle horizontal agitation. This washing step was repeated twice. The chip was then cooled to room temperature. After removal of TBS-T, the chip was incubated for 1 h with the secondary antibody, a Cy3-labeled donkey anti-human IgA, G, and M (Jackson ImmunoLab) diluted at 1:400 in 3 mL Superblock Blocking Buffer. The chip was then washed at 50 C in the same fashion as previously stated. After the final wash, the chip was rinsed in sterile water briefly, and quickly spun at 2000 rpm until dry prior to scanning. The chips were scanned with a GenePix array scanner (GenePix Pro 6.0 or GenePix 4200AL, Molecular Devices, PA) at wavelength of 536 nm. To achieve the best signal-to-noise ratio, many washing conditions with different stringencies had been tested, including increase of salt (0.5 or 1 M NaCl), addition of SDS (0.05 or 0.1%), change of washing temperature (22, 37, 40, or 50 C), and/or various combination of conditions described above. The washing condition described here gave best results among all conditions tested.

Protein Array Data Preprocessing.

Each quantified sample array image was exported from Genepix (Molecular Devices, CA) as a text file for preprocessing. The goal of preprocessing is to yield a feature of interest from each protein spot in the array that minimizes technical variability and maximizes the signal of interest. The ratio of the mean signal over the mean background signal for each protein spot was determined to be the best method of preprocessing. This method has the advantage that all features are normalized to their background signals. Thus, if a protein spot signal is artificially high due to an artifact on the slide the ratio will account for it. Furthermore this preprocessing method also normalizes the features across all arrays, as the ratio is a standardized metric. The ratio represents the fold change of the signal above background and can be interpreted as the degree of host serum reactivity to each spotted protein.

Univariate Significance Testing.

Significance Analysis for Microarrays (SAM) (27) was used to determine proteins to which healthy control, CD, and ulcerative colitis groups of samples show a statistically significant immunogenic response. We used stringent criteria in the SAM analysis and only called a protein as significant with at least 1.5 fold change differences between two phenotypes at 0% False Discovery Rate in 500 permutations.

Supervised Learning Algorithms.

To construct the classifier in this study, we employed three supervised learning methods. The algorithms implemented were k-Nearest Neighbors (kNN) (27), Support Vector Machines (SVM), and the k-Top Scoring Pairs Algorithm (k-TSP) (28). The k-TSP was implemented using a publicly available executable program developed at the Institute for Computational Medicine of Johns Hopkins University (Tan (2005) Bioinformatics. 21, 3896-3904). SVM and kNN were implemented using the R statistical programming language, packages: e1071 and class for SVM and kNN, respectively.

Feature Selection.

For kNN and SVM learning methods, SAM was applied to the training set for feature selection before the classifiers were trained on that data. The features selected in SAM were those that were found to be significant with a false discovery rate of zero. The k-TSP algorithm does not require feature reduction as it intrinsically selects the top scoring features. Parameters such as the number of nearest neighbors for kNN and the number of top scoring pairs for k-TSP were selected based on leave one out cross-validation performance on the training set. A script was written in Matlab to perform the cross-validation scheme and call executables for the learning algorithms.

Statistical Analyses.

We used the open source statistical software R to perform the statistical analyses in this study. P-value<0.05 was regarded as significant.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method for differentiating ulcerative colitis from Crohn's disease or vice versa in a human subject, the method comprising
   (a) obtaining a blood, serum or plasma sample from the human subject,
   (b) contacting the blood, serum or plasma sample of the human subject with an *E. coli* frvX polypeptide, thereby forming a human antibody-frvX polypeptide complex,
   (c) contacting the blood, serum or plasma sample of the human subject with an *E. coli* yidX polypeptide, thereby forming a human antibody-yidX polypeptide complex,
   (d) contacting the human antibody-frvX polypeptide complex and the human antibody-yidX polypeptide complex with a Cy3-labeled donkey anti-human antibody, thereby forming a first complex comprising Cy3-labeled donkey anti-human antibody-human antibody-frvX polypeptide and a second complex comprising Cy3-labeled donkey anti-human antibody-human antibody-yidX polypeptide; and
   (e) detecting the first complex and the second complex, wherein detection of a greater amount of the first complex than the second complex, or detection of an amount of the first complex equal to the second complex, identifies the subject as having ulcerative colitis, wherein detection of a greater amount of the second complex than the first complex identifies the subject as having Crohn's disease,
   thereby differentiating ulcerative colitis from Crohn's disease, or vice versa, in the human subject.

2. The method of claim 1, further comprising administering a therapy selected from the group consisting of an aminosalicylate, an immunomodulator, infliximab, adalimumab, certolizumab and an antibiotic to said subject identified as having ulcerative colitis.

3. The method of claim 1, wherein said *E. coli* frvX polypeptide and said *E. coli* yidX polypeptide are attached to an array microchip comprising at least about 85% of the *E. coli* proteome.

4. The method of claim 1, wherein said *E. coli* frvX polypeptide and said *E. coli* yidX polypeptide are attached to an array microchip comprising a set of biomarkers selected from the group consisting of *E. coli* polypeptides yhcP, yhhT, yhiW, aceF, allP, ansP, aqpZ, atoE, brnQ, celD, cobU, codB, cybB, cydB, cydC, dgt, dnaQ, ebgA, emrB, emrD, exuR, fabH, fabZ, fadA, fepD, flhD, glnQ, glpF, gppA, greA, hemY, JW0438, JW1949, lipA, lpxC, malX, malZ, menG, mrdB, murG, mutT, narU, nfrB, nrfE, ompC, oppC, oppF, pbuX, pheP, phsE, pnuC, potC, pssR, ptsH, putP, queA, rfaL, rffG, rocE, rplO, sdhD, secB, sfsA, slyX, sucB, sucD, tauB, thiL, trkH, udk, uidB, virK, yaaH, yabK, yadQ, yaeG, yagG, yagM, yaiV, yajR, ybaN, ybdS, ybfB, ybfC, ybgE, ybhA, ybhL, ybhM, ybhN, ybhR, ycaD, yccY, ycdG, yciQ, yciR, yciS, ydcD, yddH, ydeF, ydeZ, ydfO, ydjS, ydjZ, yeaS, yehK, yehY, yejF, yfjY, ygeD, ygfF, yggH, yghK, yghT, ygjQ, yhaH, yhaO, yhbX, yhcO, yhdM, yhdT, yheG, yheU, yhfU, yhhL, yhhS, yhiP, yhiQ, yhjX, yiaL, yiaQ, yibL, yibQ, yicO, yidY, yifE, yigF, yihG, yjeM, yjfF, yjfP, yjfY, yjhB, ymdD, ynaJ, yneC, yneG, ynjC, yoaA, yohG, yphA, yphG, yqcE, yzgL, rpsK, rpsL, sixA, ycfF, yhdN, yjhA, gntU, phnE, rcsC, thiS, ycfA, yfjV, aceB, agaZ, aidA, argB, argC, aroF, aroK, aspA, atpB, baiF, basS, cedA, citB, citG, clpX, cysD, cysJ, cysM, cysW, dgxA, dicC, dinD, ecnB, eno, fadB, fba, fdhE, fecB, fecR, fimB, fimC, fliA, fliS, flxA, folP, frvX, ftn, fumB, gabD, galR, gcpE, glvB, grxA, grxC, gst, hemX, hflX, hisS, hofH, hoxK, hsdM, hycA, hycF, hypC, ibpB, infC, ivbL, lasT, LDR-ABC, LDR-D, lldR, mcrD, metB, metJ, mltB, mviN, narY, nuoE, phbA, phnB, phnG, phnM, ppdB, ptpS, ptsN, purM, radC, rbfA, rbsB, recN, rffD, rpiB, rplP, rplQ, rplT, rpmJ, rpsG, rpsR, selD, slyA, slyD, ssi6, sugE, tdcB, thiF, torA, trmD, ubiG, umuD, vacJ, wcaA, ybbA, ybbQ, ycbF, ycdB, yceD, ycgN, ydfA, ydfD, ydfR, ydhL, ydiL, yedF, yehR, yejG, yejO, yfeC, yfhD, yfiC, yfiD, yfjI, yfjQ, ygbA, ygbD, ygbO, ygcQ, ygeW, ygfY, yhaA, yhaC, yhaN, yhcI, yhcJ, yhfR, yhfV, yhgH, yhgI, yicC, yieF, yieJ, yigK, yihA, yihD, yihK, yiiF, yijD, yijF, yjaI, yjbI, yjbL, yjbQ, yjbR, yjcS, yjeB, yjeJ, yjgF, yjhC, yjhE, yjhF, yjhO, yjiA, yliG, ymfE, yohL, yphC, yrbB, rtn, cadA, lueO, mesJ, mhpF, modC, murA, nrfF, prpE, purK, tpiA, yciD, yejA, ygcE, ygfQ, yhjC, yjfH, yjiJ, yeeF, dgkA, dinI, emrY, focA, folK, fsr, glnD, kch, maoC, msbA, nac, nagE, narI, ppx, prtC, rfaB, secF, secY/prlA, trkG, yafJ, yaiM, ybbC, ycbM, ydaA, ydbD, ydhV, yefI, yeiO, ygjR, yhiN, yjgT, yojI, and yphD, or fragments thereof.

5. The method of claim 1, wherein said *E. coli* frvX polypeptide and said *E. coli* yidX polypeptide are attached to an array microchip comprising a set of biomarkers selected from the group consisting of *E. coli* polypeptides rpsK, rpsL, sixA, ycfF, yhdN, yjhA, gntU, phnE, rcsC, thiS, ycfA, yfjV, aceB, agaZ, aidA, argB, argC, aroF, aroK, aspA, atpB, baiF, basS, cedA, citB, citG, clpX, cysD, cysJ, cysM, cysW, dgxA, dicC, dinD, ecnB, eno, fadB, fba, fdhE, fecB, fecR, fimB, fimC, fliA, fliS, flxA, folP, frvX, ftn, fumB, gabD, galR, gcpE, glvB, grxA, grxC, gst, hemX, hflX, hisS, hofH, hoxK, hsdM, hycA, hycF, hypC, ibpB, infC, ivbL, lasT, LDR-ABC, LDR-D, lldR, mcrD, metB, metJ, mltB, mviN, narY, nuoE, phbA, phnB, phnG, phnM, ppdB, ptpS, ptsN, purM, radC, rbfA, rbsB, recN, rffD, rpiB, rplP, rplQ, rplT, rpmJ, rpsG, rpsR, selD, slyA, slyD, ssi6, sugE, tdcB, thiF, torA, trmD, ubiG, umuD, vacJ, wcaA, ybbA, ybbQ, ycbF, ycdB, yceD, ycgN, ydfA, ydfD, ydfR, ydhL, ydiL, yedF, yehR, yejG, yejO, yfeC, yfhD, yfiC, yfiD, yfjI, yfjQ, ygbA, ygbD, ygbO, ygcQ, ygeW, ygfY, yhaA, yhaC, yhaN, yhcI, yhcJ, yhfR, yhfV, yhgH, yhgI, yicC, yieF, yieJ, yigK, yihA, yihD, yihK, yiiF, yijD, yijF, yjaI, yjbI, yjbL, yjbQ, yjbR, yjcS, yjeB, yjeJ, yjgF, yjhC, yjhE, yjhF, yjhO, yjiA, yliG, ymfE, yohL, yphC, and yrbB, or fragments thereof.

6. The method of claim 1, wherein *E. coli* frvX polypeptide and said *E. coli* yidX polypeptide are attached to an array microchip comprising a set of biomarkers selected from the group consisting of *E. coli* polypeptides rpsK, rpsL, sixA, ycfF, yhdN, yjhA, gntU, phnE, rcsC, thiS, ycfA, yfjV, aceB, agaZ, aidA, argB, argC, aroF, aroK, aspA, atpB, baiF, basS, cedA, citB, citG, clpX, cysD, cysJ, cysM, cysW, dgxA, dicC, dinD, ecnB, eno, fadB, fba, fdhE, fecB, fecR, fimB, fimC, fliA, fliS, flxA, folP, frvX, ftn, fumB, gabD, galR, gcpE, glvB, grxA, grxC, gst, hemX, hflX, hisS, hofH, hoxK, hsdM, hycA, hycF, hypC, ibpB, infC, ivbL, lasT, LDR-ABC, LDR-D, lldR, mcrD, metB, metJ, mltB, mviN, narY, nuoE, phbA, phnB, phnG, phnM, ppdB, ptpS, ptsN, purM, radC, rbfA, rbsB, recN, rffD, rpiB, rplP, rplQ, rplT, rpmJ, rpsG, rpsR, selD, slyA, slyD, ssi6, sugE, tdcB, thiF, torA, trmD, ubiG, umuD, vacJ, wcaA, ybbA, ybbQ, ycbF, ycdB, yceD, ycgN, ydfA, ydfD, ydfR, ydhL, ydiL, yedF, yehR, yejG, yejO, yfeC, yfhD, yfiC, yfiD, yfjI, yfjQ, ygbA, ygbD, ygbO, ygcQ, ygeW, ygfY, yhaA, yhaC, yhaN, yhcI, yhcJ, yhfR, yhfV, yhgH, yhgI, yicC, yieF, yieJ, yigK, yihA, yihD, yihK, yiiF, yijD, yijF, yjaI, yjbI, yjbL, yjbQ, yjbR, yjcS, yjeB, yjeJ, yjgF, yjhC, yjhE, yjhF, yjhO, yjiA, yliG, ymfE, yohL, yphC, and yrbB, or fragments thereof.

7. The method of claim 1, wherein said *E. coli* frvX polypeptide and said *E. coli* yidX polypeptide are attached to an array microchip comprising a set of biomarkers selected from the group consisting of *E. coli* polypeptides era, ybaN, yhgN, focA, ga bT and ycdG, or fragments thereof.

8. The method of claim 1, wherein said *E. coli* frvX polypeptide and said *E. coli* yidX polypeptide are attached to an array microchip comprising a set of biomarkers selected from the group consisting of *E. coli* polypeptides rtn, cadA, lueO, mesJ, mhpF, modC, murA, nrfF, prpE, purK, tpiA, yciD, yejA, ygcE, ygfQ, yhjC, yjfH, yjiJ, jeeF, dgkA, dinI, emrY, focA, folK, fsr, glnD, kch, maoC, msbA, nac, nagE, narI, ppx, prtC, rfaB, secF, secY/prlA, trkG, yafJ, yaiM, ybbC, ycbM, ydaA, ydbD, ydhV, yefI, yeiO, ygjR, yhiN, yjgT, yojI, yphD, ychP, yhhT, yhiW, aceF, allP, ansP, aqpZ, atoE, brnQ, celD, cobU, codB, cybB, cydB, cydC, dgt, dnaQ, ebgA, emrB, emrD, exuR, fabH, fabZ, fadA, fepD, flhD, glnQ, glpF, gppA, greA, hemY, JW0438, JW1949, lipA, lpxC, malX, malZ, menG, mrdB, murG, mutT, narU, nfrB, nrfE, ompC, oppC, oppF, pbuX, pheP, phsE, pnuC, potC, pssR, ptsH, putP, queA, rfaL, rffG, rocE, rplO, sdhD, secB, sfsA, slyX, sucB, sucD, tauB, thiL, trkH, udk, uidB, virK, yaaH, yabK, yadQ, yaeG, yagG, yagM, yaiV, yajR, ybaN, ybdS, ybfB, ybfC, ybgE, ybhA, ybhL, ybhM, ybhN, ybhR, ycaD, yccY, ycdG, yciQ, yciR, yciS, ydcD, yddH, ydeF, ydeZ, ydfO, ydjS, ydjZ, yeaS, yehK, yehY, yejF, yfjY, ygeD, ygfF, yggH, yghK, yghT, ygjQ, yhaH, yhaO, yhbX, yhcO, yhdM, yhdT, yheG, yheU, yhfU, yhhL, yhhS, yhiP, yhiQ, yhjX, yiaL, yiaQ, yibL, yibQ, yicO, yidY, yifE, yigF, yihG, yjeM, yjfF, yjfP, yjfY, yjhB, ymdD, ynaJ, yneC, yneG, ynjC, yoaA, yohG, yphA, yphG, yqcE, and yzgL, or fragments thereof.

9. The method of claim 1, wherein said *E. coli* frvX polypeptide and said *E. coli* yidX polypeptide are attached to an array microchip comprising a set of biomarkers selected from the group consisting of rtn, cadA, lueO, mesJ, mhpF, modC, murA, nrfF, prpE, purK, tpiA, yciD, yejA, ygcE, ygfQ, yhjC, yjfH, yjiJ, yeeF, dgkA, dinI, emrY, focA, folK, fsr, glnD, kch, maoC, msbA, nac, nagE, narI, ppx, prtC, rfaB, secF, secY/prlA, trkG, yafJ, yaiM, ybbC, ycbM, ydaA, ydbD, ydhV, yefI, yeiO, ygjR, yhiN, yjgT, yojI, and yphD, or fragments thereof.

10. The method of claim 1, wherein said *E. coli* frvX polypeptide and said *E. coli* yidX polypeptide are attached to an array microchip comprising a set of biomarkers selected from the group consisting of rpsK, rpsL, sixA, ycfF, yhdN, yjhA, gntU, phnE, rcsC, thiS, ycfA, yfjV, aceB, agaZ, aidA, argB, argC, aroF, aroK, aspA, atpB, baiF, basS, cedA, citB, citG, clpX, cysD, cysJ, cysM, cysW, dgxA, dicC, dinD, ecnB, eno, fadB, fba, fdhE, fecB, fecR, fimB, fimC, fliA, fliS, flxA, folP, frvX, ftn, fumB, gabD, galR, gcpE, glvB, grxA, grxC, gst, hemX, hflX, hisS, hofH, hoxK, hsdM, hycA, hycF, hypC, ibpB, infC, ivbL, lasT, LDR-ABC, LDR-D, lldR, mcrD, metB, metJ, mltB, mviN, narY, nuoE, phbA, phnB, phnG, phnM, ppdB, ptpS, ptsN, purM, radC, rbfA, rbsB, recN, rffD, rpiB, rplP, rplQ, rplT, rpmJ, rpsG, rpsR, selD, slyA, slyD, ssi6, sugE, tdcB, thiF, torA, trmD, ubiG, umuD, vacJ, wcaA, ybbA, ybbQ, ycbF, ycdB, yceD, ycgN, ydfA, ydfD, ydfR, ydhL, ydiL, yedF, yehR, yejG, yejO, yfeC, yfhD, yfiC, yfiD, yfjI, yfjQ, ygbA, ygbD, ygbO, ygcQ, ygeW, ygfY, yhaA, yhaC, yhaN, yhcI, yhcJ, yhfR, yhfV, yhgH, yhgI, yicC, yieF, yieJ, yigK, yihA, yihD, yihK, yiiF, yijD, yijF, yjaI, yjbI, yjbL, yjbQ, yjbR, yjcS, yjeB, yjeJ, yjgF, yjhC, yjhE, yjhF, yjhO, yjiA, yliG, ymfE, yohL, yphC, yrbB, rtn, cadA, lueO, mesJ, mhpF, modC, murA, nrfF, prpE, purK, tpiA, yciD, yejA, ygcE, ygfQ, yhjC, yjfH, yjiJ, yeeF, dgkA, dinI, emrY, focA, folK, fsr, glnD, kch, maoC, msbA, nac, nagE, narI, ppx, prtC, rfaB, secF, secY/prlA, trkG, yafJ, yaiM, ybbC, ycbM, ydaA, ydbD, ydhV, yefI, yeiO, ygjR, yhiN, yjgT, yojI, and yphD, or fragments thereof.

11. The method of claim 3, wherein said *E. coli* frvX polypeptide and said *E. coli* yidX polypeptide are attached to an array further comprising one or more biomarkers selected from the group consisting of antibodies that specifically bind chitobioside IgA (ACCA), laminaribioside IgG (ALCA), manobioside IgG (AMCA), Man α-1,3 Man α-1,2 Man (ΣMan3), Man α-1,3 Man α-1,2 Man α-1,2 Man (ΣMan4), antineutrophil cytoplasmic antibody (pANCA), yeast oligomanna antibody (*Saccharomyces cerevisiae*, ASCA), bacterial outer membrane porin C (OmpC), *Pseudomonas fluorescens* bacterial sequence I2, and bacterial flagellin (Cbir).

* * * * *